US008217204B2

(12) United States Patent
Maeda et al.

(10) Patent No.: US 8,217,204 B2
(45) Date of Patent: Jul. 10, 2012

(54) CATALYST FOR ASYMMETRIC HYDROGENATION

(75) Inventors: Hironori Maeda, Hiratsuka (JP); Yoji Hori, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 154 days.

(21) Appl. No.: 12/792,016

(22) Filed: Jun. 2, 2010

(65) Prior Publication Data

US 2010/0324338 A1 Dec. 23, 2010

Related U.S. Application Data

(63) Continuation of application No. 61/308,333, filed on Feb. 26, 2010.

(30) Foreign Application Priority Data

Jun. 3, 2009 (JP) .................. 2009-134161

(51) Int. Cl.
*C07C 45/62* (2006.01)
*C07C 29/17* (2006.01)
*B01J 31/02* (2006.01)

(52) U.S. Cl. ........ 568/433; 468/351; 468/436; 502/166; 502/167

(58) Field of Classification Search .................. 568/433, 568/436, 351; 502/166, 167
See application file for complete search history.

(56) References Cited

U.S. PATENT DOCUMENTS

| 2006/0161024 A1 | 7/2006 | MacMillan et al. |
| 2008/0269528 A1 | 10/2008 | Jakel et al. |

FOREIGN PATENT DOCUMENTS

| JP | 53-14911 A | 2/1979 |
| JP | 54-14911 A | 2/1979 |
| JP | 2008-515843 A | 5/2008 |

OTHER PUBLICATIONS

International Search Report (PCT/ISA/210) dated Sep. 14, 2010, in PCT/JP2010/059387.
Written Opinion (PCT/ISA/237) dated Sep. 14, 2010, in PCT/JP2010/059387.
Farkas, G., et al., "New chiral auxiliaries in enantioselective heterogeneous catalytic hydrogenations: (−) and (+)-dihydro-apovincaminic acid. Comparison with (−)-dihydro-apovincaminic acid ethyl ester. III", Journal of Molecular Catalysis A: Chemical, 1999, pp. 123-127, vol. 138.
Farkas, G., et al., "Enantioselective hydrogenation of isophorone over Pd catalysts in the presence of (−)-dihydroapovincaminic acid ethyl ester: The effect of reduction method of Pd blacks on the enantiomeric excess", Journal of Molecular Catalysis A: Chemical, 2001, pp. 101-107, vol. 170.
Fogassy, G., et al., "Enantioselective hydrogenation of exocyclic α,β-unsaturated ketones Part II. Hydrogenation in the presence of (S)-proline", Journal of Molecular Catalysis A: Chemical, 2002, pp. 101-106, vol. 179.
Sipos, E., et al., "Enantioselective hydrogenation of isophorone with titania supported Pd catalysts modified by (−)-dihydroapovincaminic acid ethyl ester effect of the support and the reduction method", Journal of Molecular Catalysis A: Chemical, 2002, pp. 107-112, vol. 179.
Bhaskar Kanth, J.V., et al., "Convenient Method for the Synthesis of Chiral α,α-Diphenyl-2-pyrrolidinemethanol", Tetrahedron, 1993, pp. 5127-5132, vol. 49, No. 23.
Bailey, D., et al., "A short synthesis of (S)-2-(diphenylmethyl)pyrrolidine, a chiral solvating agent for NMR analysis", Tetrahedron: Asymmetry, 1997, pp. 149-153, vol. 8, No. 1.
Farkas, G., et al., "New chiral auxiliaries in enantioselective heterogeneous catalytic hydrogenations: (−) and (+) -dihydro-apovincaminic acid. Comparison with (−) -dihydro-apovincaminic acid ethyl ester. III", Journal of Molecular Catalysis A: Chemical, 1999, pp. 123-127, vol. 138.
Farkas, G., et al., "Enantioselective hydrogenation of isophorone over Pd catalysts in the presence of (−) -dihydroapovincaminic acid ethyl ester: The effect of reduction method of Pd blacks on the enantiomeric excess", Journal of Molecular Catalysis A: Chemical, 2001, pp. 101-107, vol. 170.
Fogassy, G., et al., "Enantioselective hydrogenation of exocyclic α,β-unsaturated ketones Part II. Hydrogenation in the presence of (S)-proline", Journal of Molecular Catalysis A: Chemical, 2002, pp. 101 106, vol. 179.
Sipos, E., et al., "Enantioselective hydrogenation of isophorone with titania supported Pd catalysts modified by (−) - dihydroapovincaminic acid ethyl ester effect of the support and the reduction method", Journal of Molecular Catalysis A: Chemical, 2002, pp. 107-112, vol. 179.
Fogassy, G., et al., "Enantioselective hydrogenation of exocyclic α,β-unsaturated ketones Part III. Hydrogenation with Pd in the presence of cinchonidine", 2003, pp. 189-194, vol. 192. Ouellet, S., et al., "Enantioselective Organocatalytic Transfer Hydrogenation Reactions using Hantzsh Esters", Accounts of Chemical Research, 2007, pp. 1327-1339, vol. 40, No. 12, American Chemical Society.
Bhaskar Kanth, J.V., et al., "Convenient Method for the Synthesis of Chiral β,β-Diphenyl-2-pyrrolidinemethanol", Tetrahedron, 1993, pp. 5127-5132, vol. 49, No. 23.

*Primary Examiner* — Sikarl Witherspoon
(74) *Attorney, Agent, or Firm* — Sughrue Mion, PLLC

(57) ABSTRACT

This invention aims at providing a catalyst for producing an optically active aldehyde or an optically active ketone, which is an optically active carbonyl compound, by carrying out selective asymmetric hydrogenation of an α,β-unsaturated carbonyl compound, particularly a catalyst which is insoluble in a reaction mixture for obtaining optically active citronellal which is useful as a flavor or fragrance, by carrying out selective asymmetric hydrogenation of citral, geranial or neral; and a method for producing a corresponding optically active carbonyl compound. The invention relates to a catalyst for asymmetric hydrogenation of an α,β-unsaturated carbonyl compound, which comprises a powder of at least one metal selected from metals belonging to Group 8 to Group 10 of the Periodic Table, or a metal-supported substance in which at least one metal selected from metals belonging to Group 8 to Group 10 of the Periodic Table is supported on a support, an optically active cyclic nitrogen-containing compound and an acid.

6 Claims, No Drawings

CATALYST FOR ASYMMETRIC HYDROGENATION

CROSS-REFERENCE TO RELATED APPLICATIONS

This application claims priority from Japanese Patent Application No. 2009-134161 filed on Jun. 3, 2009 and provisional U.S. patent application No. 61/308,333 filed on Feb. 26, 2010, the entire subject matter of which is incorporated herein by reference.

BACKGROUND OF THE INVENTION

1. Field of the Invention

This invention relates to a method for producing an optically active carbonyl compound, namely an optically active aldehyde or an optically active ketone, by conducting selective asymmetric hydrogenation of carbon-carbon double bond of an $\alpha,\beta$-unsaturated carbonyl compound using a catalyst for asymmetric hydrogenation. Particularly, optically active citronellal can be obtained by conducting selective asymmetric hydrogenation of $\alpha,\beta$-unsaturated carbon-carbon double bond of geranial, neral or citral (a mixture of geranial and neral). The optically active citronellal is not only useful by itself as a flavor or fragrance but is also an important raw material of optically active citronellol, optically active isopulegol and optically active menthol.

2. Description of the Related Art

Conventionally, there have been made an attempt for conducting asymmetric hydrogenation of carbon-carbon double bond of $\alpha,\beta$-unsaturated aldehyde using hydrogen gas, and there is known a method for conducting asymmetric hydrogenation of neral and geranial for the purpose of obtaining optically active citronellal which is particularly important as a flavor or fragrance (JP-A-54-14911, JP-T-2008-515843 (the term "JP-T" as used herein means a published Japanese translation of a PCT patent application)). Since these methods are methods for hydrogenating carbon-carbon double bond with hydrogen gas using a small amount of a homogeneous catalyst, auxiliaries are not required so that a large amount of waste is not generated.

There have been reported an asymmetric hydrogenation of carbon-carbon double bond of $\alpha,\beta$-unsaturated ketone using a combination of Pd black, Pd/C or Pd/TiO$_2$ and (−)-dihydroapovincamic acid ethyl ester, proline or cinchonidine (Journal of Molecular Catalysis A: Chemical 1999, 138, 123-127, Journal of Molecular Catalysis A: Chemical 2001, 170, 101-107, Journal of Molecular Catalysis A: Chemical 2002, 179, 101-106, Journal of Molecular Catalysis A: Chemical 2002, 179, 107-112, Journal of Molecular Catalysis A: Chemical 2003, 192, 189-194).

In addition, there has been reported a hydrogen transfer type asymmetric hydrogenation reaction of an $\alpha,\beta$-unsaturated compound using an organic asymmetric catalyst and Hantzsch ester (US 2006/0161024, Acc. Chem. Res., 2007, 40, 1327-1339).

SUMMARY OF THE INVENTION

However, the catalyst used by the methods of JP-A-54-14911 and JP-T-2008-515843 is a homogeneous catalyst which uses expensive rhodium metals and the like, and it is difficult to recover the catalyst because it dissolves in the reaction solution.

In the methods of Journal of Molecular Catalysis A: Chemical 1999, 138, 123-127, Journal of Molecular Catalysis A: Chemical 2001, 170, 101-107, Journal of Molecular Catalysis A: Chemical 2002, 179, 101-106, Journal of Molecular Catalysis A: Chemical 2002, 179, 107-112, and Journal of Molecular Catalysis A: Chemical 2003, 192, 189-194, there are only isophorone and a special exocyclic ketone and the catalyst system of the invention is not used.

The methods of using organic catalyst described in Acc. Chem. Res., 2007, 40, 1327-1339, and US 2006/0161024 are economically disadvantageous as a method for producing an optically active aldehyde or an optically active ketone, because a catalyst quantity of about 20% by mol based on the raw material unsaturated aldehyde or unsaturated ketone is required and the Hantzsch ester as the substrate of hydrogenation is required in an amount of equal to or larger than the raw material unsaturated aldehyde or unsaturated ketone.

Accordingly, concern has been directed toward the development of a method for easily recovering a catalyst by the use of heterogeneous catalyst such as a solid catalyst which does not dissolve in the reaction solution.

In addition, an asymmetric hydrogenation reaction of an $\alpha,\beta$-unsaturated aldehyde using heterogeneous catalyst such as a solid catalyst has not been known.

An object of the invention relates to a method for conducting asymmetric hydrogenation of carbon-carbon double bond of an $\alpha,\beta$-unsaturated carbonyl compound using, as a catalyst for asymmetric hydrogenation, a heterogeneous catalyst which can be easily separated from the reaction solution and thereby obtaining corresponding optically active aldehyde or optically active ketone. Particularly, it relates to a method for obtaining optically active citronellal by hydrogenating citral, geranial or neral by asymmetric hydrogenation reaction.

The inventors have conducted intensive studies with the aim of solving the above-mentioned problems and found as a result that a corresponding optically active aldehyde or optically active ketone can be obtained by conducting asymmetric hydrogenation of an $\alpha,\beta$-unsaturated carbonyl compound using a specified metal powder or metal-supported substance, an optically active cyclic nitrogen-containing compound and an acid, thereby resulting in the accomplishment of the invention. In addition, after completion of the reaction, the optically active nitrogen-containing compound and metal powder or metal-supported substance can be easily recovered from the reaction system and reused again as the catalyst for asymmetric hydrogenation.

That is, the invention includes the following respective inventions.

[1] A catalyst for asymmetric hydrogenation of an $\alpha,\beta$-unsaturated carbonyl compound, which comprises:
a powder of at least one metal selected from metals belonging to Group 8 to Group 10 of the Periodic Table, or a metal-supported substance in which at least one metal selected from metals belonging to Group 8 to Group 10 of the Periodic Table is supported on a support; an optically active cyclic nitrogen-containing compound; and an acid.

[2] The catalyst for asymmetric hydrogenation according to [1], wherein the optically active cyclic nitrogen-containing compound is a compound represented by the following general formula (1):

[Chem. 1]

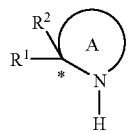

(1)

wherein ring A is a three- to seven-membered ring which may have a substituent, comprises at least one kind of atom selected from the group consisting of a carbon atom, a nitrogen atom, a sulfur atom, an oxygen atom and a phosphorous atom, and may be a fused ring structure; $R^1$ and $R^2$ each independently represent an hydrogen atom, an alkyl group which may have a substituent, a cycloalkyl group which may have a substituent, an alkenyl group which may have a substituent, an aryl group which may have a substituent, an aralkyl group which may have a substituent, an alkoxy group which may have a substituent, a carboxyl group which may have a substituent, alkoxycarbonyl group which may have a substituent, an amido group which may have a substituent, a siloxy group which may have a substituent, an aromatic heterocyclic group which may have a substituent or an aliphatic heterocyclic group which may have a substituent, wherein $R^1$ and $R^2$ do not represent a same substituent, and either $R^1$ or $R^2$ may be bonded to the ring A to further form a ring; and * represents an asymmetric carbon atom.

[3] The catalyst for asymmetric hydrogenation according to [1] or [2], wherein the metal is selected from the group consisting of nickel, ruthenium, rhodium, iridium, palladium and platinum.

[4] A method for manufacturing an optically active carbonyl compound represented by the following general formula (3):

[Chem. 3]

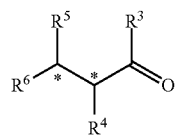

(3)

wherein $R^3$, $R^4$, $R^5$ and $R^6$ are the same as defined in the following formula (2), and two * mean that at least one * represents an asymmetric carbon atom, wherein the method comprises conducting asymmetric hydrogenation of an α, β-unsaturated carbonyl compound represented by the following general formula (2) by using the catalyst for asymmetric hydrogenation according to any one of [1] to [3]:

[Chem. 2]

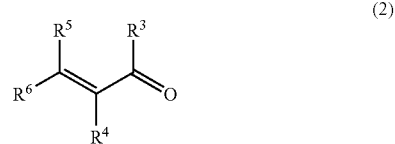

(2)

wherein $R^3$, $R^4$, $R^5$ and $R^6$ each independently represent an hydrogen atom, an alkyl group which may have a substituent, a cycloalkyl group which may have a substituent, an alkenyl group which may have a substituent, an aryl group which may have a substituent, or an aralkyl group which may have a substituent, and a ring may be formed by $R^3$ and $R^4$, $R^3$ and $R^5$, $R^3$ and $R^6$, $R^4$ and $R^6$, or $R^5$ and $R^6$; and when a ring is not formed by $R^3$ and $R^4$, or $R^3$ and $R^5$, and $R^4$ does not represent a hydrogen atom, $R^5$ and $R^6$ may be the same or different from each other; and when a ring is not formed by $R^3$ and $R^4$, or $R^3$ and $R^5$, and $R^4$ represents a hydrogen atom, $R^5$ and $R^6$ do not represent a hydrogen atom and are different from each other.

[5] The method according to claim [4], wherein the α,β-unsaturated carbonyl compound is geranial, neral or citral.

[6] The method according to claim [4], wherein the α,β-unsaturated carbonyl compound is ketones having a five- to sixteen-membered ring.

As described in the foregoing, as the catalyst of the asymmetric hydrogenation reaction, the invention uses an optically active cyclic nitrogen-containing compound and an acid as additives which contribute to the enantio-selectivity, together with a metal powder or metal-supported substance.

The asymmetric hydrogenation catalyst of the invention does not require a reaction step for preparing a catalyst like the conventional asymmetric hydrogenation catalyst. In the invention, asymmetric hydrogenation is carried out by simply mixing a raw material compound, an optically active cyclic nitrogen-containing compound, a metal powder or metal-supported substance and an acid. Thus, the operation is convenient and the metal powder or metal-supported substance and optically active cyclic nitrogen-containing compound can be recovered and reused, which is industrially advantageous.

In addition, in case of using, as a substance, each of a Z-configuration or E-configuration compound regarding the α-position and β-position double bond of the α,β-unsaturated carbonyl compound, when using the catalyst of the invention, the configuration of the formed optically active carbonyl compound depends on the configuration of the optically active cyclic nitrogen-containing compound to be used. Thus, according to the invention, even when a mixture of the Z-configuration compound and E-configuration compound is used as the substrate, an optically active carbonyl compound having the same configuration can be produced.

DETAILED DESCRIPTION OF THE INVENTION

The following describes the invention in detail.
<Substrate>

According to the invention, an α,β-unsaturated carbonyl compound is used as the substrate, and an optically active aldehyde or an optically active ketone, which is an optically active carbonyl compound, is produced by subjecting this to asymmetric hydrogenation using the catalyst of the invention.

As the α,β-unsaturated carbonyl compound to be used as the substrate, a compound represented by the following general formula (2) can, for example, be mentioned, though not particularly limited thereto. In this connection, in the case of the presence of Z-configuration and E-configuration regarding the α-position and β-position double bond of the α,β-unsaturated carbonyl compound, all of them are included therein.

[Chem. 4]

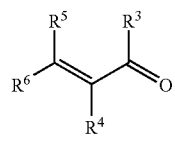

General formula (2)

(In the formula (2), $R^3$, $R^4$, $R^5$ and $R^6$ each independently represent a hydrogen atom, an alkyl group which may have a substituent group, a cycloalkyl group which may have a substituent group, an alkenyl group which may have a substituent group, an aryl group which may have a substituent group or an aralkyl group which may have a substituent group. In addition, $R^3$ and $R^4$, $R^3$ and $R^5$, $R^3$ and $R^6$, $R^4$ and $R^6$ or $R^5$ and $R^6$ may form a ring. However, in case that a ring is not formed by $R^3$ and $R^4$ or $R^3$ and $R^5$, when $R^4$ does not represent a hydrogen atom, $R^5$ and $R^6$ may be same or different from each other and when $R^4$ represents a hydrogen atom, $R^5$ and $R^6$ are other than hydrogen atom and different from each other.)

An optically active aldehyde or an optically active ketone, which is an optically active carbonyl compound represented by the following formula (3), is produced by subjecting a compound represented by the aforementioned formula (2), namely an α,β-unsaturated aldehyde or an α,β-unsaturated ketone, to asymmetric hydrogenation using the catalyst of the invention.

[Chem. 5]

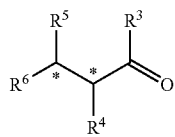

(In the formula (3), $R^3$, $R^4$, $R^5$ and $R^6$ are the same as the definition of the formula (2). Two * mean that at least one * represents an asymmetric carbon atom.)

Regarding the α,β-unsaturated carbonyl compound represented by the general formula (2) and the optically active carbonyl compound represented by the general formula (3), the groups represented by $R^3$, $R^4$, $R^5$ and $R^6$, namely the alkyl group, cycloalkyl group, alkenyl group, aryl group and aralkyl group, are described. Each of these groups may have a substituent group.

As the alkyl group, a straight chain or branched chain alkyl group, for example, having from 1 to 30 carbon atoms, preferably from 1 to 10 carbon atoms, can be mentioned, and illustratively, there may be mentioned methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group and the like.

In addition, these alkyl groups may have a substituent group, and as said substituent group of alkyl groups, for example, there may be mentioned an alkenyl group, an alkynyl group, an aryl group, an aliphatic heterocyclic group, an aromatic heterocyclic group, an alkoxy group, an alkylenedioxy group, an aryloxy group, an aralkyloxy group, a heteroaryloxy group, a substituted amino group, nitro group, nitrile group, a halogen atom, an alkyl halide group and the like.

As the alkenyl group as a substituent group of alkyl group, there may be mentioned a straight chain or branched chain alkenyl group having, for example, from 2 to 20 carbon atoms, preferably from 2 to 10 carbon atoms, more preferably from 2 to 6 carbon atoms, and illustratively, vinyl group, propenyl group, 1-butenyl group, pentenyl group, hexenyl group and the like can be mentioned.

As the alkynyl group which substitutes on alkyl group, there may be mentioned a straight chain or branched chain alkynyl group having, for example, from 2 to 15 carbon atoms, preferably from 2 to 10 carbon atoms, more preferably from 2 to 6 carbon atoms, and illustratively, ethynyl group, 1-propynyl group, 2-propynyl group, 1-butynyl group, 3-butynyl group, pentinyl group, hexynyl group and the like can be mentioned.

As the aryl group as a substituent group of alkyl group, an aryl group having, for example, from 6 to 14 carbon atoms can be mentioned, and illustratively, phenyl group, naphthyl group, anthryl group, phenanthryl group, biphenyl group, tolyl group, xylyl group, mesityl group, methoxyphenyl group, dimethoxyphenyl group, fluorophenyl group and the like can be mentioned.

As the aliphatic heterocyclic group as a substituent group of alkyl group, there may be mentioned a group which has, for example, from 2 to 14 carbon atoms and contains, as heterogeneous atoms, at least one, preferably from 1 to 3 hetero atoms such as nitrogen atom, oxygen atom and sulfur atom. Preferably, a 5- or 6-membered monocyclic aliphatic heterocyclic group and a polycyclic or condensed ring aliphatic heterocyclic group can be mentioned. As illustrative examples of the aliphatic heterocyclic group, for example, 2-oxo-1-pyrrolidinyl group, piperidino group, piperazinyl group, morpholino group, tetrahydrofuryl group, tetrahydropyranyl group, tetrahydrothienyl group and the like can be mentioned.

As the aromatic heterocyclic group as a substituent group of alkyl group, there may be mentioned a group which has, for example, from 2 to 15 carbon atoms and contains, heterogeneous atoms, at least one, preferably from 1 to 3 hetero atoms such as nitrogen atom, oxygen atom and sulfur atom. Preferably, a 5- or 6-membered monocyclic aromatic heterocyclic group and a polycyclic or condensed ring aromatic heterocyclic group can be mentioned. As illustrative examples of the aromatic heterocyclic group, for example, there may be mentioned furyl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as a substituent group of alkyl group, a straight chain or branched chain alkoxy group having, for example, from 1 to 6 carbon atoms can be mentioned, and illustratively, methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group and the like can be mentioned.

As the alkylenedioxy group as a substituent group of alkyl group, an alkylenedioxy group having, for example, from 1 to 3 carbon atoms can be mentioned, illustratively, methylenedioxy group, ethylenedioxy group, propylenedioxy group, isopropylidenedioxy group and the like can be mentioned.

As the aryloxy group as a substituent group of alkyl group, an aryloxy group having, for example, from 6 to 14 carbon atoms can be mentioned, and illustratively, phenoxy group, naphthyloxy group, anthryloxy group and the like can be mentioned.

As the aralkyloxy group as a substituent group of alkyl group, for example, an aralkyloxy group having from 7 to 12 carbon atom can be mentioned, and illustratively, there may be mentioned benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

As the heteroaryloxy group as a substituent group of alkyl group, there may be mentioned a heteroaryloxy group which has, for example, from 2 to 14 carbon atoms and contains, as heterogeneous atoms, at least one, preferably from 1 to 3 hetero atoms such as nitrogen atom, oxygen atom and sulfur atom, and illustratively, 2-pyridyloxy group, 2-pyrazyloxy group, 2-pyrimidyloxy group, 2-quinolyloxy group and the like can be mentioned.

As the substituted amino group as a substituent group of alkyl group, for example, there may be mentioned mono- or di-alkylamino groups such as N-methylamino group, N,N-dimethylamino group, N,N-diethylamino group, N,N-diisopropylamino group and N-cyclohexylamino group; mono- or di-acylamino group such as N-phenylamino group, N,N-diphenylamino group, N-naphthylamino group and N-naphthyl-N-phenylamino group; mono- or di-aralkylamino group such as N-benzylamino group and N,N-dibenzylamino group.

As the halogen atom substituting the alkyl group, for example, fluorine atom, chlorine atom, bromine atom, iodine atom and the like can be mentioned.

As the alkyl halide group substituting the alkyl group, a perhalogenoalkyl group is desirable, and for example, trifluoromethyl group, pentafluoroethyl group, heptafluoropropyl group, undecafluoropentyl group, heptadecafluorooctyl group, undecafluorocyclohexyl group, dichloromethyl group and the like can be mentioned.

As the cycloalkyl group, for example, cyclopropyl group, cyclobutyl group, cyclopentyl group, cyclohexyl group and the like can be mentioned.

These cycloalkyl groups may have a substituent group, and as said substituent group, the substituent groups described in the aforementioned description on the substituent group of alkyl group can be mentioned.

As the alkenyl group, a straight or branched chain or cyclic alkenyl group having, for example, from 2 to 20 carbon atoms, preferably from 2 to 10 carbon atoms, can be mentioned. As illustrative alkenyl groups, for example, vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like can be mentioned.

These alkenyl groups may have a substituent group, and as said substituent group, the groups described in the aforementioned description on the substituent group of alkyl group can be mentioned.

As the aryl group, an aryl group having, for example, from 6 to 14 carbon atoms can be mentioned, and illustratively, phenyl group, naphthyl group, anthryl group, phenanthryl group, biphenyl group and the like can be mentioned.

These aryl groups may have a substituent group, and as said substituent group, the groups described in the description on the substituent group of alkyl group can be mentioned.

As the aralkyl group, an aralkyl group having, for example, from 7 to 12 carbon atoms is desirable, and illustratively, benzyl group, 2-phenylethyl group, 1-phenylpropyl group, 3-naphthylpropyl group and the like can be mentioned.

These aralkyl groups may have a substituent group, and as said substituent group, the groups described in the description on the substituent group of alkyl group can be mentioned.

Regarding the ring formed by $R^3$ and $R^4$, $R^3$ and $R^5$, $R^3$ and $R^6$, $R^4$ and $R^6$ or $R^5$ and $R^6$ in the α,β-unsaturated carbonyl compound represented by the general formula (2) and the optically active carbonyl compound represented by the general formula (3), for example, there may be mentioned cyclopentane ring, cyclohexane ring, indane ring, tetralin ring, cyclopentene ring, cyclohexene ring, cycloheptene ring, indene ring, dihydronaphthalene ring, octahydronaphthalene ring, decahydronaphthalene ring and the like. These rings may be substituted with the aforementioned alkyl group or the acyl group described in the following.

As the acyl group, for example, acetyl group, propanoyl group, butanoyl group, octanoyl group, benzoyl group, toluoyl group, xyloyl group, naphthoyl group, phenanthroyl group, anthroyl group and the like can be mentioned.

As illustrative examples of the α,β-unsaturated aldehyde to be used as the substrate in the invention, for example, the following compounds can be mentioned. In this connection, in the case of the presence of Z-configuration and E-configuration regarding the α-position and β-position double bond of the α,β-unsaturated aldehyde, all of them are included therein. The wavy line in the following compounds represents Z-configuration and E-configuration or a mixture thereof.

In the following compounds, Me represents methyl group, and Bn represents benzyl group.

[Chem. 6}

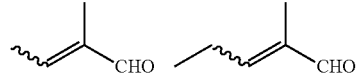

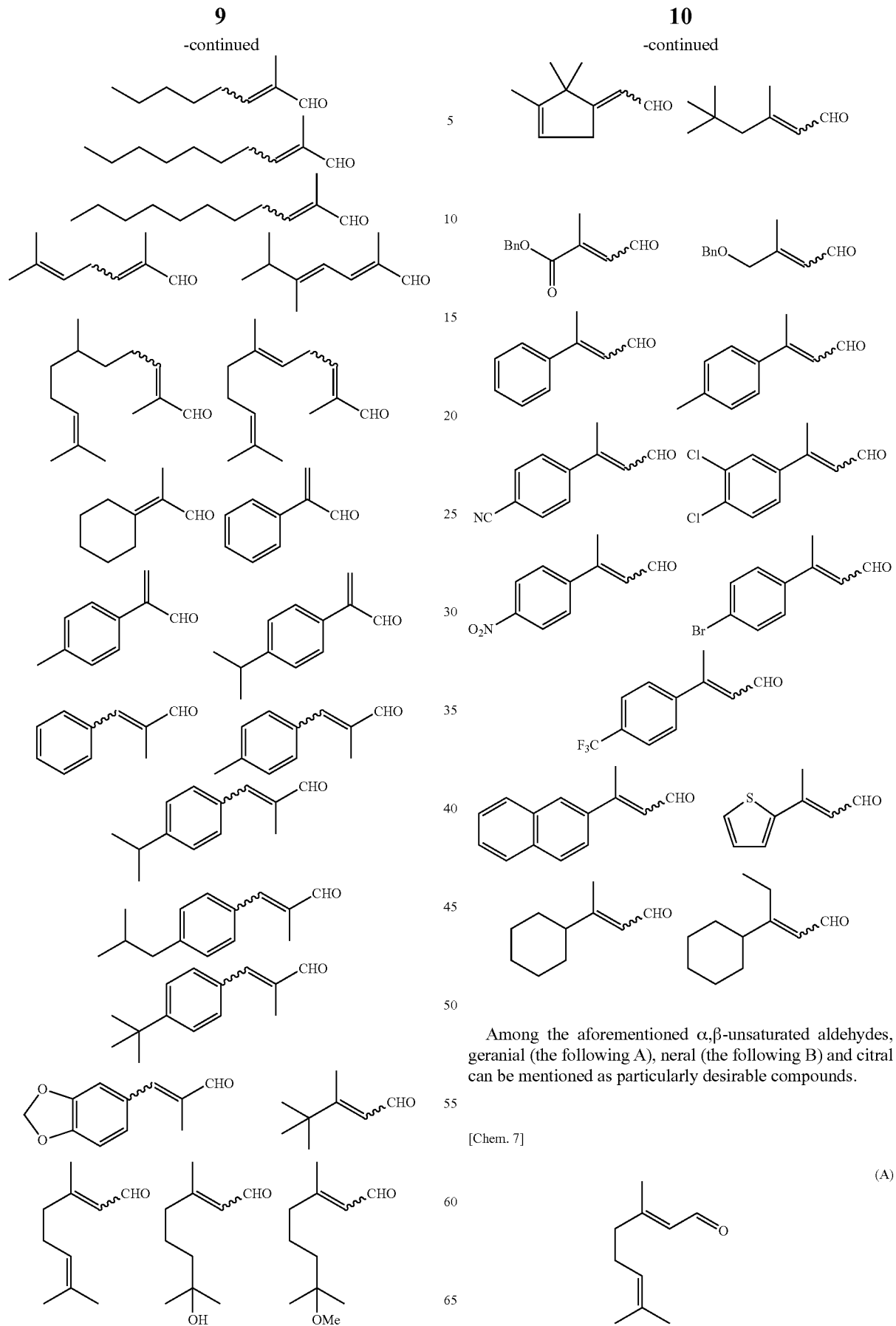
Among the aforementioned α,β-unsaturated aldehydes, geranial (the following A), neral (the following B) and citral can be mentioned as particularly desirable compounds.
[Chem. 7]

(B)

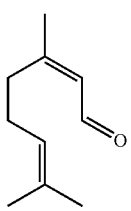

As the α,β-unsaturated ketone to be used as the substrate in the invention, 5- to 16-membered ketones are desirable.

As illustrative examples of the α,β-unsaturated ketone, the following compounds can, for example, be mentioned. In this connection, in the case of the presence of Z-configuration and E-configuration regarding the α-position and β-position double bond of the α,β-unsaturated ketone, all of them are included therein. The wavy line in the following compounds represents Z-configuration and E-configuration or a mixture thereof.

In the following compounds, Me represents methyl group, and Ph represents phenyl group, Et represents ethyl group, Bu represents butyl group, Pr represents propyl group and Bn represents benzyl group.

[Chem. 8]

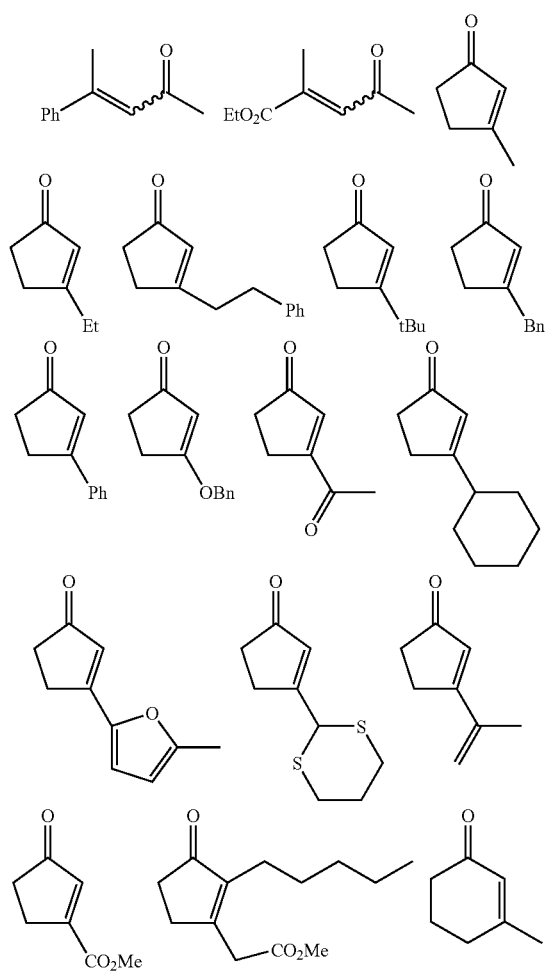

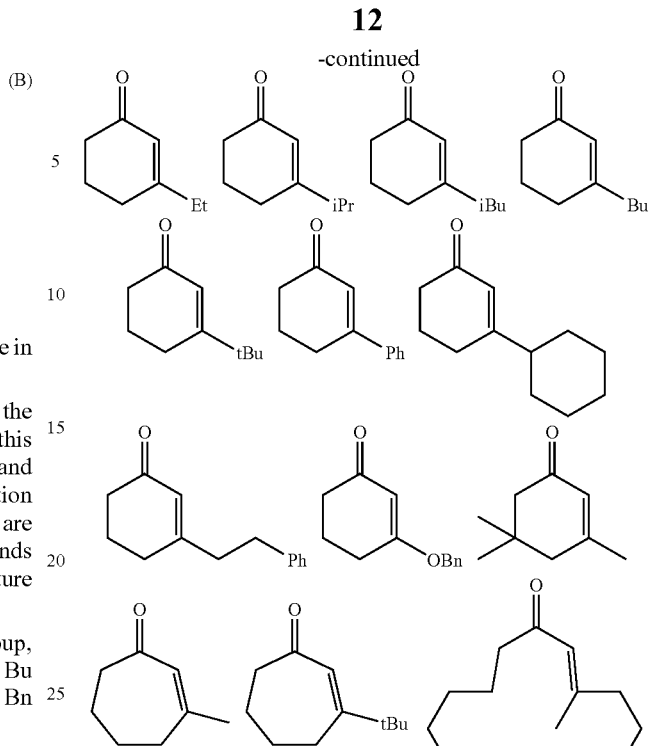

<Catalyst>

Next, the catalyst of the invention is described.

The catalyst of the invention is a catalyst for asymmetric hydrogenation of an α,β-unsaturated carbonyl compound, which comprises a powder of at least one metal selected from metals belonging to Group 8 to Group 10 of the Periodic Table, or a metal-supported substance in which at least one metal selected from metals belonging to Group 8 to Group 10 of the Periodic Table is supported on a support, an optically active cyclic nitrogen-containing compound and an acid.

The following describes the powder of at least one metal selected from metals belonging to Group 8 to Group 10 of the Periodic Table and the metal-supported substance in which at least one metal selected from metals belonging to Group 8 to Group 10 of the Periodic Table is supported on a support.

As the metals belonging to Group 8 to Group 10 of the Periodic Table, Ni (nickel), Ru (ruthenium), Rh (rhodium), Ir (iridium), Pd (palladium)) and Pt (platinum) are desirable, of which particularly desirable metal is Pd.

As the metal powder, Pd black, Pt black and the like can, for example, be mentioned.

As the metal-supported substance, those in which the above-mentioned metals are supported on a support are used, and those in which these metals are supported on supports such as carbon, silica, alumina, silica-alumina, zeolite, a metal oxide, a metal halide, a metal sulfide, a metal sulfonate, a metal nitrate, a metal carbonate or a metal phosphate are suitably used. Among these, a substance in which palladium or platinum is supported on a support is desirable.

As illustrative metal-supported substance, Raney nickel, Ru/C, Rh/C, Pd/C, Ir/C, Pt/C, Pd/Al$_2$O$_3$, Pd/SiO$_2$, Pd/TiO$_2$, Pd/ZrO$_2$, Pd/CeO$_2$, Pd/ZnO, Pd/CdO, Pd/TiO$_2$, Pd/SnO$_2$, Pd/PbO, Pd/As$_2$O$_3$, Pd/Bi$_2$O$_3$, Pd/Sb$_2$O$_5$, Pd/V$_2$O$_5$, Pd/Nb$_2$O$_5$, Pd/Cr$_2$O$_3$, Pd/MoO$_3$, Pd/WO$_3$, Pd/BeO, Pd/MgO, Pd/CaO, Pd/SrO, Pd/BaO, Pd/Y$_2$O$_3$, Pd/La$_2$O$_3$, Pd/Na$_2$O, Pd/K$_2$O, Pd/CdS, Pd/ZnS, Pd/MgSO$_4$, Pd/CaSO$_4$, Pd/SrSO$_4$, Pd/BaSO$_4$, Pd/CuSO$_4$, Pd/ZnSO$_4$, Pd/CdSO$_4$, Pd/Al$_2$(SO$_4$)$_3$, Pd/FeSO$_4$, Pd/Fe$_2$(SO$_4$)$_3$, Pd/CoSO$_4$, Pd/NiSO$_4$, Pd/Cr$_2$(SO$_4$)$_3$, Pd/KHSO$_4$, Pd/K$_2$SO$_4$, Pd/(NH$_4$)$_2$SO$_4$, Pd/Zn(NO$_3$)$_2$, Pd/Ca(NO$_3$)$_2$, Pd/Bi(NO$_3$)$_3$, Pd/Fe(NO$_3$)$_3$, Pd/Na$_2$CO$_3$, Pd/K$_2$CO$_3$, Pd/KHCO$_3$, Pd/KNaCO$_3$, Pd/CaCO$_3$, Pd/SrCO$_3$, Pd/BaCO$_3$, Pd/(NH$_4$)$_2$CO$_3$, Pd/Na$_2$WO$_4$.2H$_2$O, Pd/KCN, Pd/BPO$_4$, Pd/AlPO$_4$, Pd/CrPO$_4$, Pd/FePO$_4$, Pd/Cu$_3$(PO$_4$)$_2$, Pd/Zn$_3$(PO$_4$)$_2$, Pd/Mg$_3$(PO$_4$)$_2$, Pd/Ti$_3$(PO$_4$)$_4$, Pd/Zr$_3$(PO$_4$)$_4$, Pd/Ni$_3$(PO$_4$)$_2$, Pd/AgCl, Pd/CuCl, Pd/CaCl$_2$, Pd/AlCl$_3$, Pd/TiCl$_3$, Pd/SnCl$_2$, Pd/CaF$_2$, Pd/BaF$_2$, Pd/AgClO$_4$, Pd/Mg(ClO$_4$)$_2$, Pd/Zeolite, Pd/SiO$_2$—Al$_2$O$_3$, Pd/SiO$_2$—TiO$_3$, Pd/SiO$_2$—ZRO$_2$, Pd/SiO$_2$—BeO, Pd/SiO$_2$—MgO, Pd/SiO$_2$—CaO, Pd/SiO$_2$—SrO, Pd/SiO$_2$—BaO, Pd/SiO$_2$—ZnO, Pd/SiO$_2$—TiO$_2$, Pd/SiO$_2$—ZrO$_2$, Pd/SiO$_2$—Ga$_2$O$_3$, Pd/SiO$_2$—Y$_2$O$_3$, Pd/SiO$_2$—La$_2$O$_3$, Pd/SiO$_2$—MoO$_3$, Pd/SiO$_2$—WO$_3$, Pd/SiO$_2$—V$_2$O$_5$, Pd/SiO$_2$—ThO$_2$, Pd/Al$_2$O$_3$—MgO, Pd/Al$_2$O$_3$—ZnO, Pd/Al$_2$O$_3$—CdO, Pd/Al$_2$O$_3$—B$_2$O$_3$, Pd/Al$_2$O$_3$—ThO$_2$, Pd/Al$_2$O$_3$—TiO$_2$, Pd/Al$_2$O$_3$—ZrO$_2$, Pd/Al$_2$O$_3$—V$_2$O$_5$, Pd/Al$_2$O$_3$—MoO$_3$, Pd/Al$_2$O$_3$—WO$_3$, Pd/Al$_2$O$_3$—Cr$_2$O$_3$, Pd/Al$_2$O$_3$—Mn$_2$O$_3$, Pd/Al$_2$O$_3$—Fe$_2$O$_3$, Pd/Al$_2$O$_3$—Co$_3$O$_4$, Pd/Al$_2$O$_3$—Nio, Pd/TiO$_2$—CuO, Pd/TiO$_2$—MgO, Pd/TiO$_2$—ZnO, Pd/TiO$_2$—CdO, Pd/TiO$_2$—ZrO$_2$, Pd/TiO$_2$—SnO$_2$, Pd/TiO$_2$—Bi$_2$O$_3$, Pd/TiO$_2$—Sb$_2$O$_5$, Pd/TiO$_2$—V$_2$O$_5$, Pd/TiO$_2$—Cr$_2$O$_3$, Pd/TiO$_2$—MoO$_3$, Pd/TiO$_2$—WO$_3$, Pd/TiO$_2$—Mn$_2$O$_3$, Pd/TiO$_2$—Fe$_2$O$_3$, Pd/TiO$_2$—Co$_3$O$_4$, Pd/TiO$_2$—NiO, Pd/ZrO$_2$—CdO, Pd/ZnO—MgO, Pd/ZnO—Fe$_2$O$_3$, Pd/MoO$_3$—CoO—Al$_2$O$_3$, Pd/MoO$_3$—NiO—Al$_2$O$_3$, Pd/TiO$_2$—SiO$_2$—MgO, Pd/MoO$_3$—Al$_2$O$_3$—MgO, Pd/Heteropoly acids, Pt/SiO$_2$, Pt/Al$_2$O$_3$, Pt/Zeolite, Rh/Al$_2$O$_3$ and the like can be mentioned.

Next, the optically active cyclic nitrogen-containing compound to be used as a catalyst component of the invention is described.

As the optically active cyclic nitrogen-containing compound, for example, an optically active cyclic nitrogen-containing compound represented by the general formula (1) can be mentioned.

[Chem. 9]

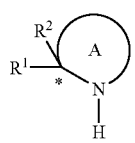

(1)

(In the formula (1), ring A is a 3- to 7-membered ring, may have a substituent group, contains at least one atom selected from the group consisting of carbon, nitrogen, sulfur, oxygen and phosphorus, is preferably constituted from said atoms and may form a fused ring structure; $R^1$ and $R^2$ each independently represent a hydrogen atom, an alkyl group which may have a substituent group, a cycloalkyl group which may have a substituent group, an alkenyl group which may have a substituent group, an aryl group which may have a substituent group, an aralkyl group which may have a substituent group, an alkoxy group which may have a substituent group, a carboxyl group which may have a substituent group, an alkoxycarbonyl group which may have a substituent group, an amido group which may have a substituent group, a siloxy group which may have a substituent group, an aromatic heterocyclic group which may have a substituent group or an aliphatic heterocyclic group which may have a substituent group, wherein $R^1$ and $R^2$ do not represent a same substituent group, and either $R^1$ or $R^2$ may be bonded to the ring A to further form a ring; and * represents an asymmetric carbon atom.)

As basic skeleton of the ring A, for example, aziridine skeleton, azetidine skeleton, pyrrolidine skeleton, pyrroline skeleton, pyrazolidine skeleton, imidazolidine skeleton, imidazolidinone skeleton, pyrazoline skeleton, thiazolidine skeleton, piperidine skeleton, piperazine skeleton, morpholine skeleton, thiomorpholine skeleton and the like can be mentioned. A substituent group may be present in these basic skeletons.

As basic skeleton in the case that the ring A is a fused ring structure by benzene ring or the like, for example, indoline skeleton, dihydroquinoxaline skeleton, tetrahydroisoquinoline skeleton, dihydroquinoxalinone skeleton and the like can be mentioned. A substituent group may be present in these basic skeletons.

As the substituent group, a hydroxyl group, an oxo group, a halogen atom, an alkyl group, an alkoxy group, an amino group, an alkoxycarbonyl group, an acyl group, an aryl group, an aralkyl group, an aromatic heterocyclic group and an aliphatic heterocyclic group can be mentioned. As the alkyl group, alkoxy group, alkoxycarbonyl group, aryl group, aralkyl group, aromatic heterocyclic group and aliphatic heterocyclic group, the groups which are enumerated in the description of $R^1$ and $R^2$ can be mentioned. As the halogen atom, fluorine atom, chlorine atom, bromine atom, iodine atom and the like can, for example, be mentioned. As the acyl group, for example, acetyl group, propanoyl group, butanoyl group, octanoyl group, benzoyl group, toluoyl group, xyloyl group, naphthoyl group, phenanthroyl group, anthroyl group and the like can be mentioned.

As the ring A and fused ring A, among these, pyrrolidine skeleton which may have a substituent group, imidazolidinone skeleton which may have a substituent group and dihydroquinoxalinone skeletons which may have a substituent group are desirable.

As suitable examples of the substituent group of ring A and fused ring A, an alkyl group which may have a substituent group, an aralkyl group which may have a substituent group and an aromatic heterocyclic group which may have a substituent group can be mentioned.

Next, the alkyl group, cycloalkyl group, alkenyl group, aryl group, aralkyl group, alkoxy group, carboxyl group, alkoxycarbonyl group, amido group, siloxy group, aromatic heterocyclic group and aliphatic heterocyclic group, as the groups represented by $R^1$ and $R^2$, are described. Each of these groups may have a substituent group.

As the alkyl group, a straight chain or branched chain alkyl group having, for example, from 1 to 30 carbon atoms, preferably from 1 to 10 carbon atoms, can be mentioned, and illustratively, there may be mentioned methyl group, ethyl group, n-propyl group, isopropyl group, n-butyl group, 2-butyl group, isobutyl group, tert-butyl group, n-pentyl group, 2-pentyl group, 3-pentyl group, tert-pentyl group, 2-methylbutyl group, 3-methylbutyl group, 2,2-dimethylpropyl group, 1,2-dimethylpropyl group, n-hexyl group, 2-hexyl group, 3-hexyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group, heneicosyl group, docosyl group and the like.

In addition, these alkyl groups may have a substituent group, and as said substituent group of alkyl groups, for example, there may be mentioned an alkenyl group, an alkynyl group, an aryl group, an aliphatic heterocyclic group, an aromatic heterocyclic group, an alkoxy group, a trialkylsiloxy group, an alkylenedioxy group, an aryloxy group, an aralkyloxy group, a heteroaryloxy group, a substituted amino group, an alkyl halide group, a cycloalkyl group, a hydroxyl group, a halogen atom and the like.

As the alkenyl group as a substituent group of alkyl group, there may be mentioned a straight chain or branched chain alkenyl group having, for example, from 2 to 20 carbon atoms, preferably from 2 to 10 carbon atoms, more preferably from 2 to 6 carbon atoms, and illustratively, vinyl group, propenyl group, 1-butenyl group, pentenyl group, hexenyl group and the like can be mentioned.

As the alkynyl group which substitutes on alkyl group, there may be mentioned a straight chain or branched chain alkynyl group having, for example, from 2 to 15 carbon atoms, preferably from 2 to 10 carbon atoms, more preferably from 2 to 6 carbon atoms, and illustratively, ethynyl group, 1-propynyl group, 2-propynyl group, 1-butynyl group, 3-butynyl group, pentinyl group, hexynyl group and the like can be mentioned.

As the aryl group as a substituent group of alkyl group, an aryl group having, for example, from 6 to 20 carbon atoms can be mentioned, and illustratively, phenyl group, tolyl group, isopropylphenyl group, xylyl group, t-butylphenyl group, cyclohexyl group, 1-methylcyclohexyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9', 10'-heptadecafluorodecyl)phenyl group, fluorophenyl group and the like can be mentioned.

As the aliphatic heterocyclic group as a substituent group of alkyl group, there may be mentioned a group which has, for example, from 2 to 14 carbon atoms and contains, as heterogeneous atoms, at least one, preferably from 1 to 3 hetero atoms such as nitrogen atom, oxygen atom and sulfur atom. Preferably, a 5- or 6-membered monocyclic aliphatic heterocyclic group and a polycyclic or condensed ring aliphatic heterocyclic group can be mentioned. As illustrative examples of the aliphatic heterocyclic group, for example, 2-oxo-1-pyrrolidinyl group, piperidino group, piperazinyl group, morpholino group, tetrahydrofuryl group, tetrahydropyranyl group, tetrahydrothienyl group and the like can be mentioned.

As the aromatic heterocyclic group as a substituent group of alkyl group, there may be mentioned a group which has, for example, from 2 to 15 carbon atoms and contains, as heterogeneous atoms, at least one, preferably from 1 to 3 hetero atoms such as nitrogen atom, oxygen atom and sulfur atom. Preferably, a 5- or 6-membered monocyclic aromatic heterocyclic group and a polycyclic or condensed ring aromatic heterocyclic group can be mentioned. As illustrative examples of the aromatic heterocyclic group, for example, there may be mentioned furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

As the alkoxy group as a substituent group of alkyl group, a straight chain or branched chain alkoxy group having, for example, from 1 to 8 carbon atoms can be mentioned, and illustratively, methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group and the like can be mentioned.

As the trialkylsiloxy group as a substituent group of alkyl group, for example, trimethylsiloxy group, triethylsiloxy group, dimethyl-tert-butylsiloxy group and the like can be mentioned.

As the alkylenedioxy group as a substituent group of alkyl group, an alkylenedioxy group having, for example, from 1 to 3 carbon atoms can be mentioned, illustratively, methylenedioxy group, ethylenedioxy group, propylenedioxy group, isopropylidenedioxy group and the like can be mentioned.

As the aryloxy group as a substituent group of alkyl group, an aryloxy group having, for example, from 6 to 15 carbon atoms can be mentioned, and illustratively, phenoxy group, naphthyloxy group, anthryloxy group, tolyloxy group, xylyloxy group, 4-phenylphenoxy group, 3,5-diphenylphenoxy group, 4-mesitylphenoxy group, 3,5-bis(trifluoromethyl)phenoxy group and the like can be mentioned.

As the aralkyloxy group as a substituent group of alkyl group, for example, an aralkyloxy group having from 7 to 12 carbon atom can be mentioned, and illustratively, there may be mentioned benzyloxy group, 2-phenylethoxy group, 1-phenylpropoxy group, 2-phenylpropoxy group, 3-phenylpropoxy group, 1-phenylbutoxy group, 2-phenylbutoxy group, 3-phenylbutoxy group, 4-phenylbutoxy group, 1-phenylpentyloxy group, 2-phenylpentyloxy group, 3-phenylpentyloxy group, 4-phenylpentyloxy group, 5-phenylpentyloxy group, 1-phenylhexyloxy group, 2-phenylhexyloxy group, 3-phenylhexyloxy group, 4-phenylhexyloxy group, 5-phenylhexyloxy group, 6-phenylhexyloxy group and the like.

As the heteroaryloxy group as a substituent group of alkyl group, there may be mentioned a heteroaryloxy group which has, for example, from 2 to 14 carbon atoms and contains, as heterogeneous atoms, at least one, preferably from 1 to 3 hetero atoms such as nitrogen atom, oxygen atom and sulfur atom, and illustratively, 2-pyridyloxy group, 2-pyrazyloxy group, 2-pyrimidyloxy group, 2-quinolyloxy group and the like can be mentioned.

As the substituted amino group as a substituent group of alkyl group, for example, there may be mentioned mono- or di-alkylamino groups such as N-methylamino group, N,N-dimethylamino group, N,N-diethylamino group, N,N-diisopropylamino group, N-cyclohexylamino group, pyrrolidyl group, piperidyl group and morpholyl group; mono- or di-arylamino group such as N-phenylamino group, N,N-diphenylamino group, N-naphthylamino group and N-naphthyl-N- phenylamino group; mono- or di-aralkylamino group such as N-benzylamino group and N,N-dibenzylamino group; and the like.

As the alkyl halide substituting the alkyl group, a perhalogenoalkyl group is desirable, and for example, trifluoromethyl group, pentafluoroethyl group, heptafluoropropyl group, undecafluoropentyl group, heptadecafluorooctyl group, undecafluorocyclohexyl group, dichloromethyl group and the like can be mentioned.

As the cycloalkyl group substituting the alkyl group, for example, cyclopropyl group, cyclobutyl group, cyclopentyl group, cyclohexyl group and the like can be mentioned.

As the halogen atom substituting the alkyl group, for example, fluorine atom, chlorine atom, bromine atom, iodine atom and the like can be mentioned.

As the cycloalkyl group, for example, cyclopropyl group, cyclobutyl group, cyclopentyl group, cyclohexyl group and the like can be mentioned.

These cycloalkyl groups may have a substituent group, and as said substituent group, the substituent groups described in the aforementioned description on the substituent group of alkyl group can be mentioned.

As the alkenyl group, a straight or branched chain or cyclic alkenyl group having, for example, from 2 to 20 carbon atoms, preferably from 2 to 10 carbon atoms, can be mentioned. As illustrative alkenyl groups, for example, vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-cyclopentenyl group, 3-cyclopentenyl group, 1-hexenyl group, 2-hexenyl group, 3-hexenyl group, 4-hexenyl group, 5-hexenyl group, 4-methyl-3-pentenyl group, 4,8-dimethyl-3,7-nonadienyl group, 1-cyclohexenyl group, 3-cyclohexenyl group and the like can be mentioned.

These alkenyl groups may have a substituent group, and as said substituent group, the groups described in the aforementioned description on the substituent group of alkyl group can be mentioned.

As the aryl group, an aryl group having, for example, from 6 to 20 carbon atoms can be mentioned, and illustratively, phenyl group, tolyl group, isopropylphenyl group, xylyl group, t-butylphenyl group, cyclohexyl group, 1-methylcyclohexyl group, adamantylphenyl group, trifluoromethylphenyl group, naphthyl group, anthryl group, phenanthryl group, biphenyl group, 4-(2'-p-tolylpropyl)phenyl group, mesityl group, methoxyphenyl group, dimethoxyphenyl group, 4-(3',4',5',6',7',8',9',10'-heptadecafluorodecyl)phenyl group, fluorophenyl group and the like can be mentioned.

These aryl groups may have a substituent group, and as said substituent group, the groups described in the description on the substituent group of alkyl group can be mentioned.

As the aralkyl group, an aralkyl group having, for example, from 7 to 45 carbon atoms is desirable, and illustratively, there may be mentioned benzyl group, tolylmethyl group, xylylmethyl group, mesitylmethyl group, 4-phenylphenylmethyl group, 3-phenylphenylmethyl group, 2-phenylphenylmethyl group, 4-mesitylphenylmethyl group, 1-naphthylmethyl group, 2-naphthylmethyl group, 9-anthrylmethyl group, 9-phenanthrylmethyl group, 3,5-diphenylphenylmethyl group, 2-phenylethyl group, 1-phenylpropyl group, 3-naphthylpropyl group, diphenylmethyl group, ditolylmethyl group, dixylylmethyl group, dimesitylmethyl group, di(4-phenylphenyl)methyl group, di(3-phenylphenyl)methyl group, di(2-phenylphenyl)methyl group, di(4-mesitylphenyl)methyl group, di-1-naphthylmethyl group, di-2-naphthylmethyl group, di-9-anthrylmethyl group, di-9-phenanthrylmethyl group, bis(3,5-diphenylphenyl)methyl group, triphenylmethyl group, tritolylmethyl group, trixylylmethyl group, trimesitylmethyl group, tri(4-phenylphenyl)methyl group, tri(3-phenylphenyl)methyl group, tri(2-phenylphenyl)methyl group, tri(4-mesitylphenyl)methyl group, tri-1-naphthyl methyl group, tri-2-naphthylmethyl group, tri-9-anthrylmethyl group, tri-9-phenanthrylmethyl group, tris(3,5-diphenylphenyl)methyl group, trimethylsiloxyphenylmethyl group, trimethylsiloxydiphenyl methyl group, trimethylsiloxyditolyl methyl group, trimethyl siloxydi(4-t-butylphenyl)methyl group, trimethylsiloxydixylylmethyl group, trimethylsiloxydi(2-phenylphenyl)methyl group, trimethylsiloxydi(3-phenylphenyl)methyl group, trimethylsiloxydi(4-phenylphenyl)methyl group, trimethylsiloxybis(3,5-diphenylphenyl)methyl group, trimethylsiloxydi(4-mesitylphenyl)methyl group, trimethylsiloxybis(3,5-ditrifluoromethylphenyl)methyl group and the like.

These aralkyl groups may have a substituent group, and as said substituent group, the groups described in the description on the substituent group of alkyl group can be mentioned.

As the alkoxy group, an alkoxy group having, for example, from 1 to 30 carbon atoms is desirable, and illustratively, methoxy group, ethoxy group, n-propoxy group, isopropoxy group, n-butoxy group, 2-butoxy group, isobutoxy group, tert-butoxy group, n-pentyloxy group, 2-methylbutoxy group, 3-methylbutoxy group, 2,2-dimethylpropoxy group, n-hexyloxy group, 2-methylpentyloxy group, 3-methylpentyloxy group, 4-methylpentyloxy group, 5-methylpentyloxy group, cyclopentyloxy group, cyclohexyloxy group, dicyclopentylmethoxy group, dicyclohexylmethoxy group, tricyclopentyl methoxy group, tricyclohexylmethoxy group, phenylmethoxy group, diphenylmethoxy group, triphenylmethoxy group and the like can be mentioned.

These alkoxy groups may have a substituent group, and as said substituent group, the groups described in the description on the substituent group of alkyl group can be mentioned.

As the carboxyl group, a carboxyl group having, for example, from 1 to 30 carbon atoms is desirable, and illustratively, acetoxy group, n-propanoyloxy group, isopropanoyloxy group, n-butanoyloxy group, 2-butanoyloxy group, isobutanoyloxy group, tert-butanoyloxy group, n-pentanoyloxy group, 2-methylbutanoyloxy group, 3-methylbutanoyloxy group, 2,2-dimethylpropanoyloxy group, n-hexanoyloxy group, 2-methylpentanoyloxy group, 3-methylpentanoyloxy group, 4-methylpentanoyloxy group, 5-methylpentanoyloxy group, cyclopentanoyloxy group, cyclohexanoyloxy group, dicyclopentylacetoxy group, dicyclohexylacetoxy group, tricyclopentylacetoxy group, tricyclohexylacetoxy group, phenylacetoxy group, diphenylacetoxy group, triphenylacetoxy group, benzoyloxy group, naphthoyloxy group and the like can be mentioned.

These carboxyl groups may have a substituent group, and as said substituent group, the groups described in the description on the substituent group of alkyl group can be mentioned.

As the alkoxycarbonyl group, an alkoxycarbonyl group having, for example, from 1 to 30 carbon atoms is desirable, and illustratively, methoxycarbonyl group, ethoxycarbonyl group, n-propoxycarbonyl group, isopropoxycarbonyl group, n-butoxycarbonyl group, 2-butoxycarbonyl group, isobutoxycarbonyl group, tert-butoxycarbonyl group, n-pentyloxycarbonyl group, 2-methylbutoxycarbonyl group, 3-methylbutoxycarbonyl group, 2,2-dimethylpropoxycarbonyl group, n-hexyloxycarbonyl group, 2-methylpentyloxycarbonyl group, 3-methylpentyloxycarbonyl group, 4-methylpentyloxycarbonyl group, 5-methylpentyloxycarbonyl group, cyclopentyloxycarbonyl group, cyclohexyloxycarbonyl group, dicyclopentylmethoxycarbonyl group, dicyclohexylmethoxycarbonyl group, tricyclopentylmethoxycarbonyl group, tricyclohexylmethoxycarbonyl group, phenylmethoxycarbonyl group, diphenylmethoxycarbonyl group, triphenylmethoxycarbonyl group and the like can be mentioned.

These alkoxycarbonyl groups may have a substituent group, and as said substituent group, the groups described in the description on the substituent group of alkyl group can be mentioned.

As the amido group, an amido group having, for example, from 1 to 30 carbon atoms is desirable, and illustratively, acetamido group, n-propionamido group, isopropionamido group, n-butanamido group, 2-butanamido group, isobutanamido group, tert-butanamido group, n-pentanamido group, 2-methylbutanamido group, 3-methylbutanamido group, 2,2-dimethyl propionamido group, n-hexanamido group, 2-methylpentanamido group, 3-methylpentanamido group, 4-methylpentanamido group, 5-methylpentanamido group, cyclopentanamido group, cyclohexanamido group, dicyclopentylacetamido group, dicyclohexylacetamido group, tricyclopentylacetamido group, tricyclohexylacetamido group, phenylacetamido group, diphenylacetamido group, triphenylacetamido group, benzamido group, naphthalenamido group and the like can be mentioned.

These amido groups may have a substituent group, and as said substituent group, the groups described in the description on the substituent group of alkyl group can be mentioned.

As the siloxy group, trimethylsiloxy group, triethylsiloxy group, dimethyl-tert-butylsiloxy group and the like can be mentioned.

These siloxy groups may have a substituent group, and as said substituent group, the groups described in the description on the substituent group of alkyl group can be mentioned.

As the aromatic heterocyclic group, there may be mentioned a group which has, for example, from 2 to 15 carbon atoms and contains, as heterogeneous atoms, at least one, preferably from 1 to 3 hetero atoms such as nitrogen atom, oxygen atom and sulfur atom. Preferably, a 5- or 6-membered monocyclic aromatic heterocyclic group and a polycyclic or condensed ring aromatic heterocyclic group can be mentioned. As illustrative examples of the aromatic heterocyclic group, for example, there may be mentioned furyl group, methylfuryl group, thienyl group, pyridyl group, pyrimidinyl group, pyrazinyl group, pyridazinyl group, pyrazolinyl group, imidazolyl group, oxazolinyl group, thiazolinyl group, benzofuryl group, benzothienyl group, quinolyl group, isoquinolyl group, quinoxalinyl group, phtharazinyl group, quinazolinyl group, naphthylidinyl group, cinnolinyl group, benzimidazolyl group, benzoxazolyl group, benzothiazolyl group and the like.

These aromatic heterocyclic groups may have a substituent group, and as said substituent group, the groups described in the description on the substituent group of alkyl group can be mentioned.

As the aliphatic heterocyclic group, there may be mentioned a group which has, for example, from 2 to 14 carbon atoms and contains, as heterogeneous atoms, at least one, preferably from 1 to 3 hetero atoms such as nitrogen atom, oxygen atom and sulfur atom. Preferably, a 5- or 6-membered monocyclic aliphatic heterocyclic group and a polycyclic or condensed ring aliphatic heterocyclic group can be mentioned. As illustrative examples of the aliphatic heterocyclic group, for example, 2-oxo-1-pyrrolidinyl group, piperidino group, piperazinyl group, morpholino group, tetrahydrofuryl group, tetrahydropyranyl group, tetrahydrothienyl group and the like can be mentioned.

These aliphatic heterocyclic groups may have a substituent group, and as said substituent group, the groups described in the description on the substituent group of alkyl group can be mentioned.

As preferred examples of the groups represented by $R^1$ and $R^2$, hydrogen, an alkyl group which may have a substituent group and an aralkyl group which may have a substituent group can be mentioned.

In this connection, amino acids do not meet the optically active cyclic nitrogen-containing compound of the invention.

As illustrative optically active cyclic nitrogen-containing compounds, the following compounds can, for example, be mentioned.

In the following compounds, Me represents methyl group, and Ph represents phenyl group, Bu represents butyl group, Bn represents benzyl group, Et represents ethyl group, TMS represents trimethylsilyl group and polymer represents a polymer chain.

[Chem. 10]

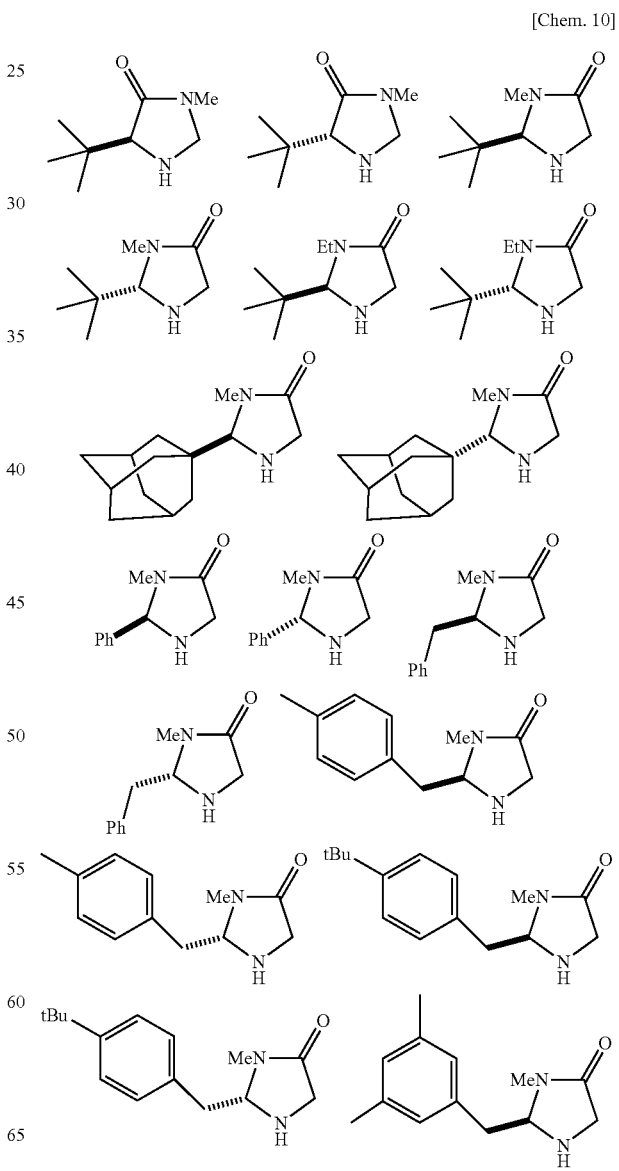

-continued
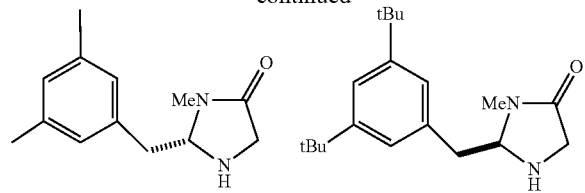
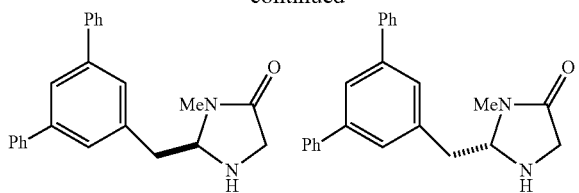
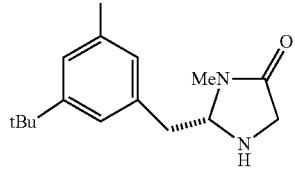
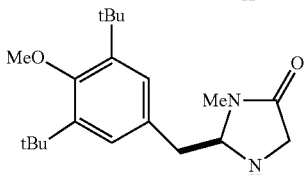
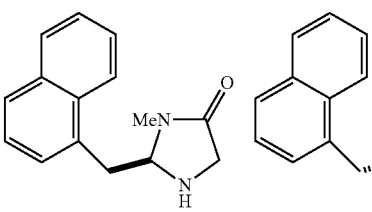
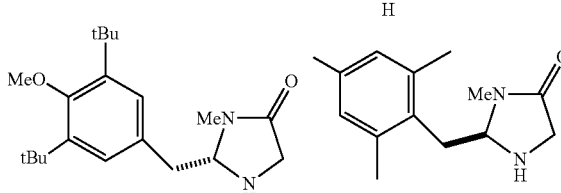
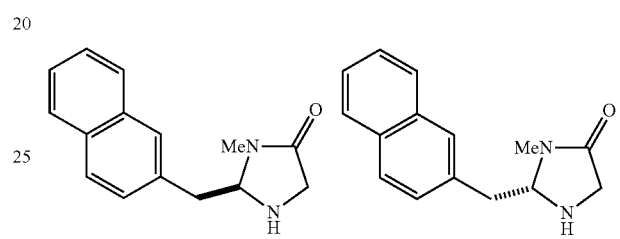
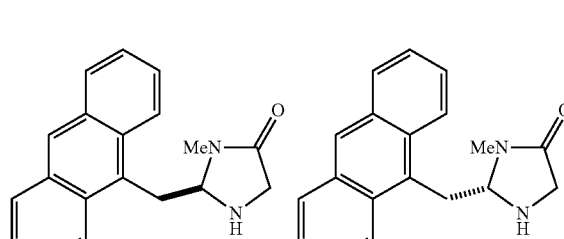
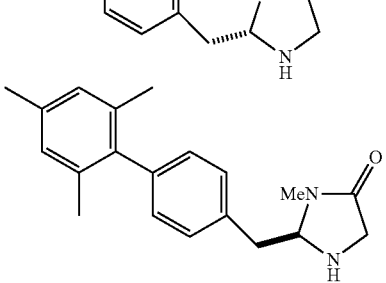
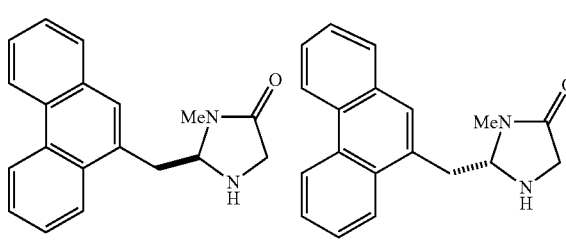
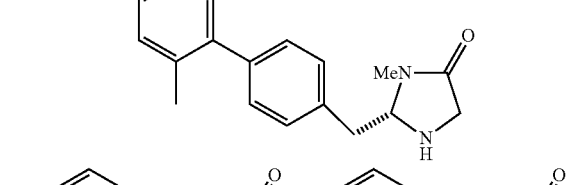
[Chem. 11]
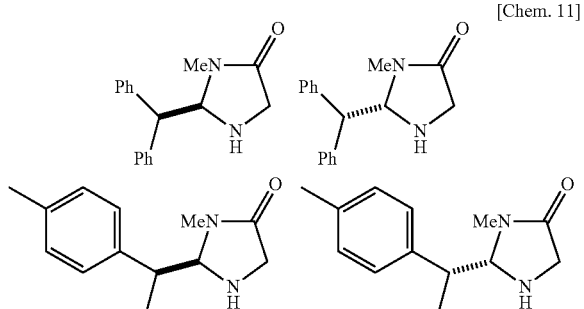
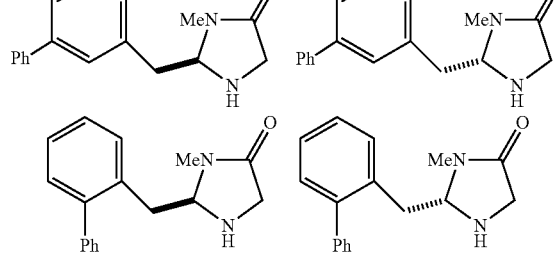

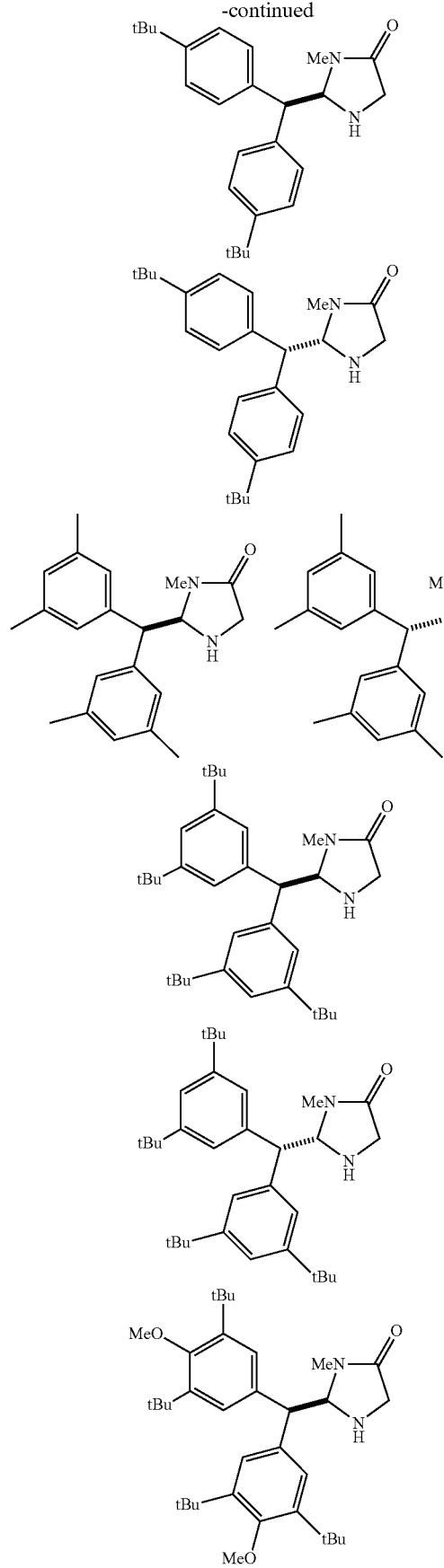
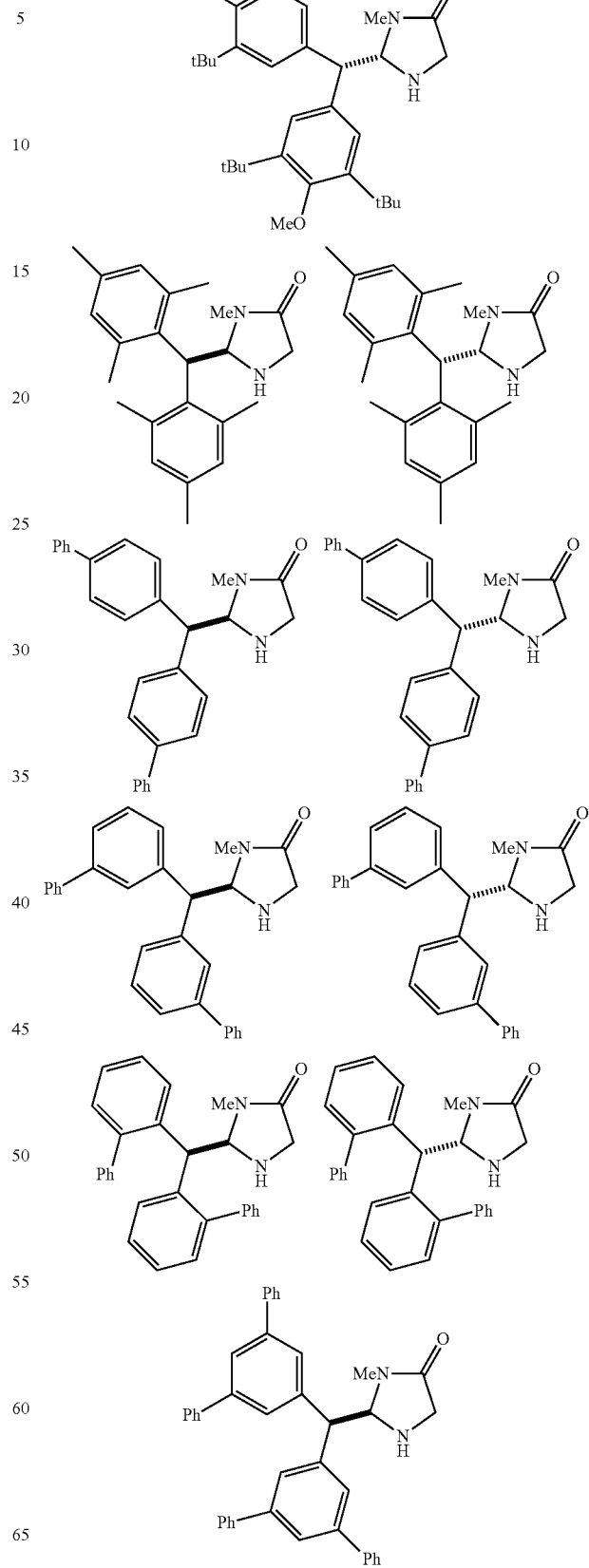

-continued
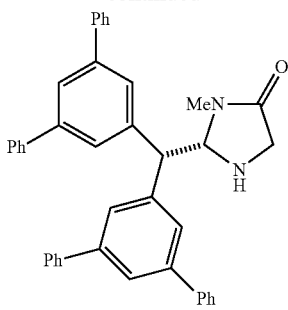
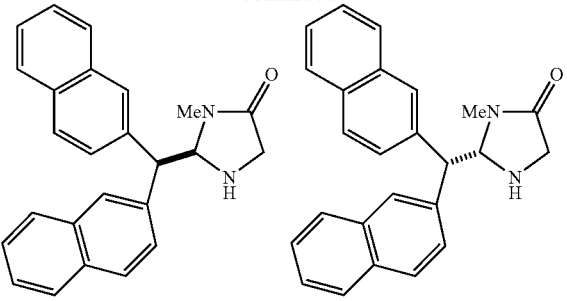
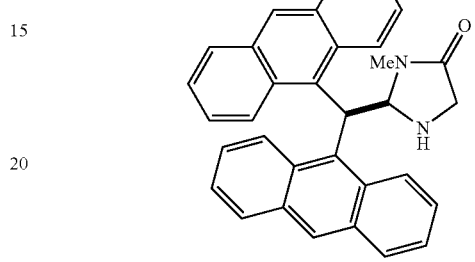
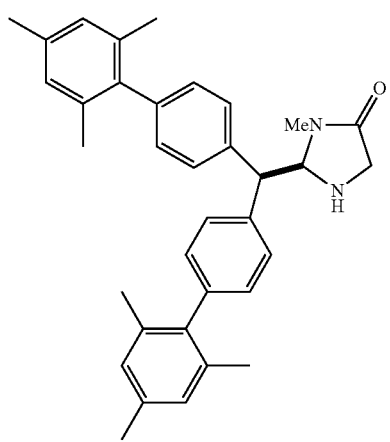
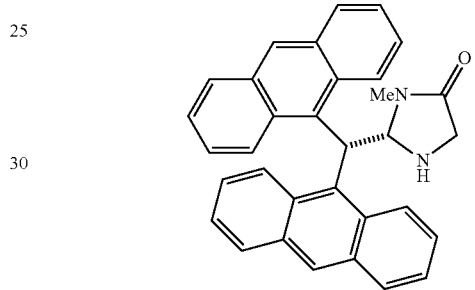
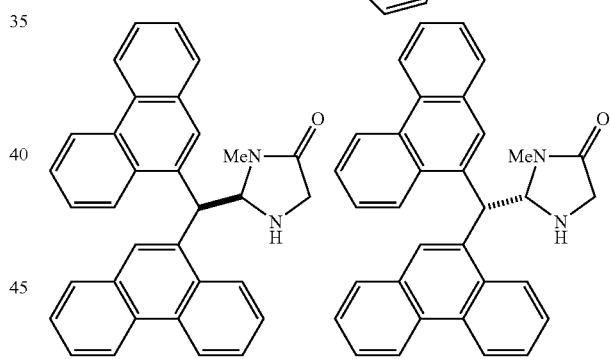
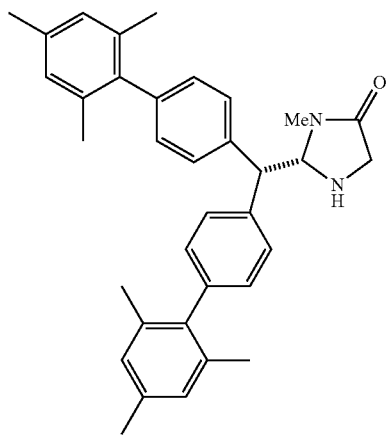
[Chem. 13]
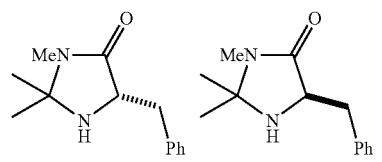
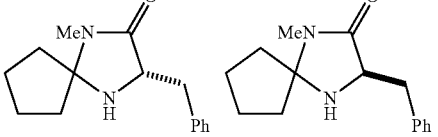
[Chem. 12]
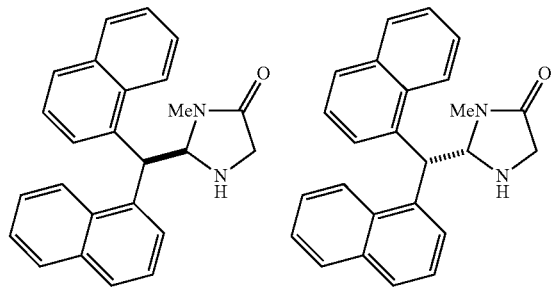
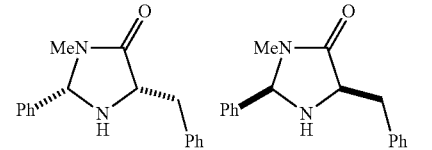

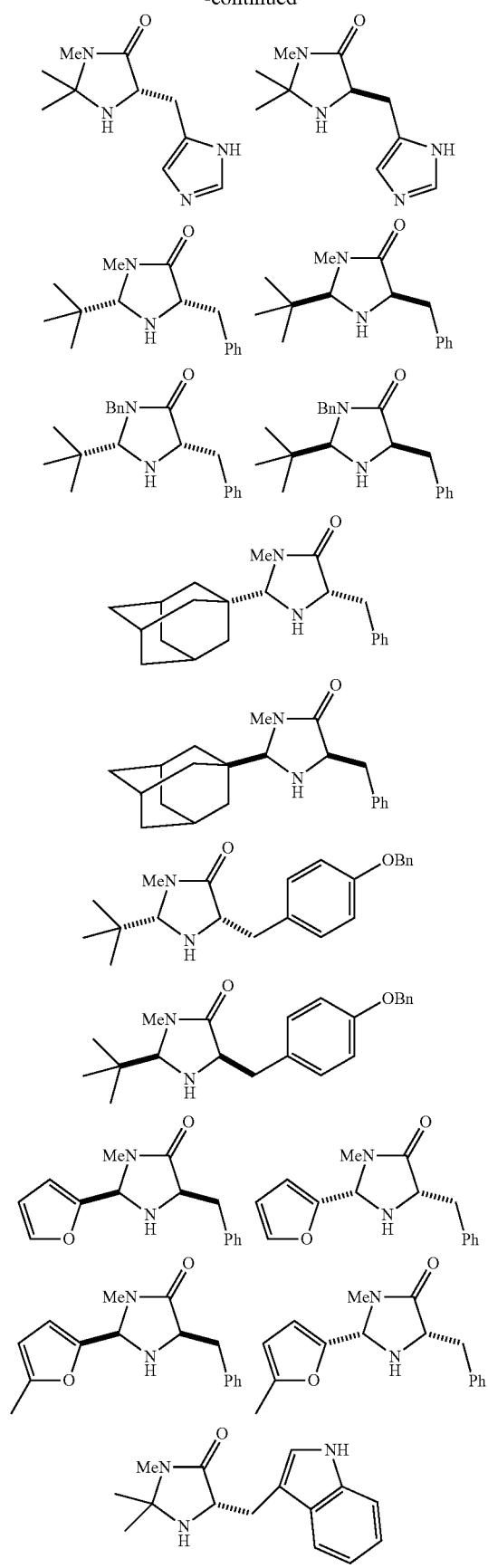
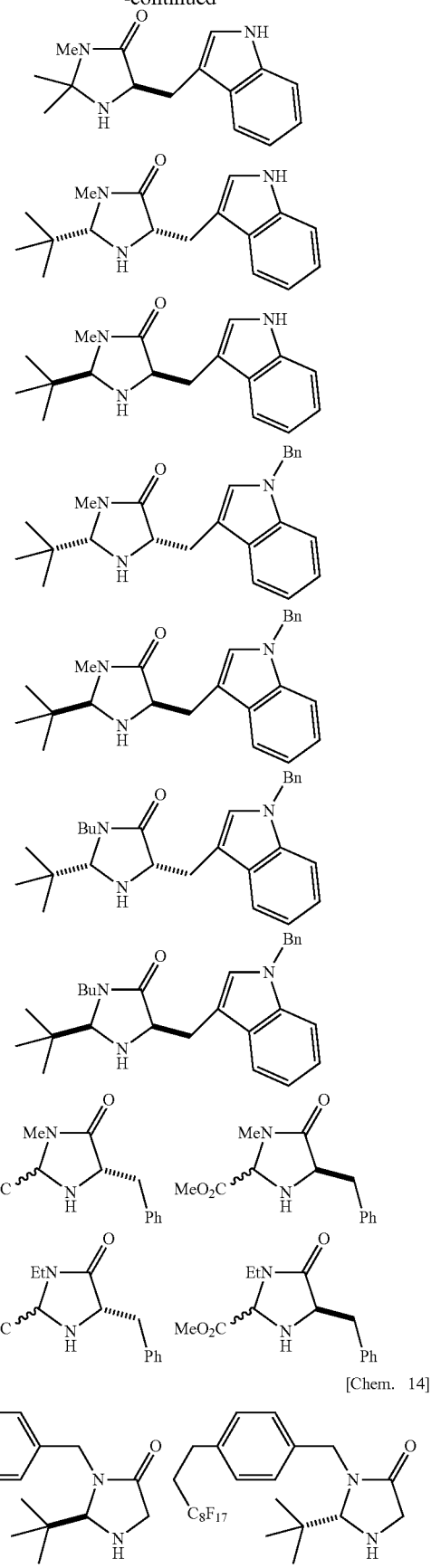
[Chem. 14]

29
-continued
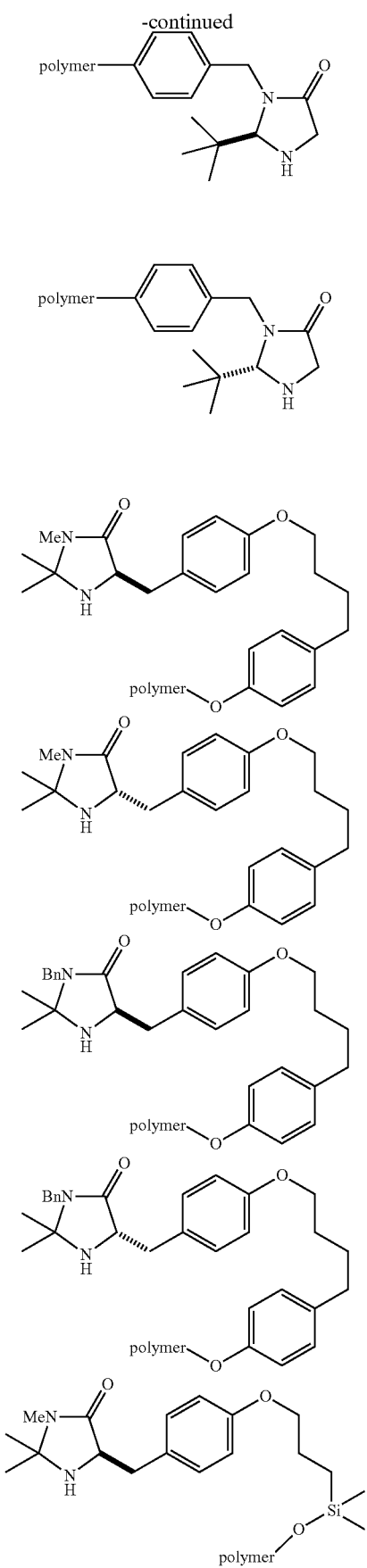
30
-continued
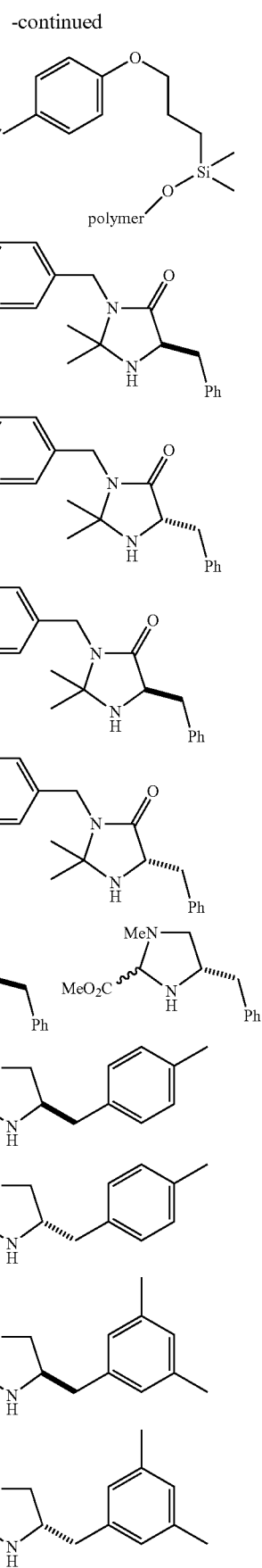

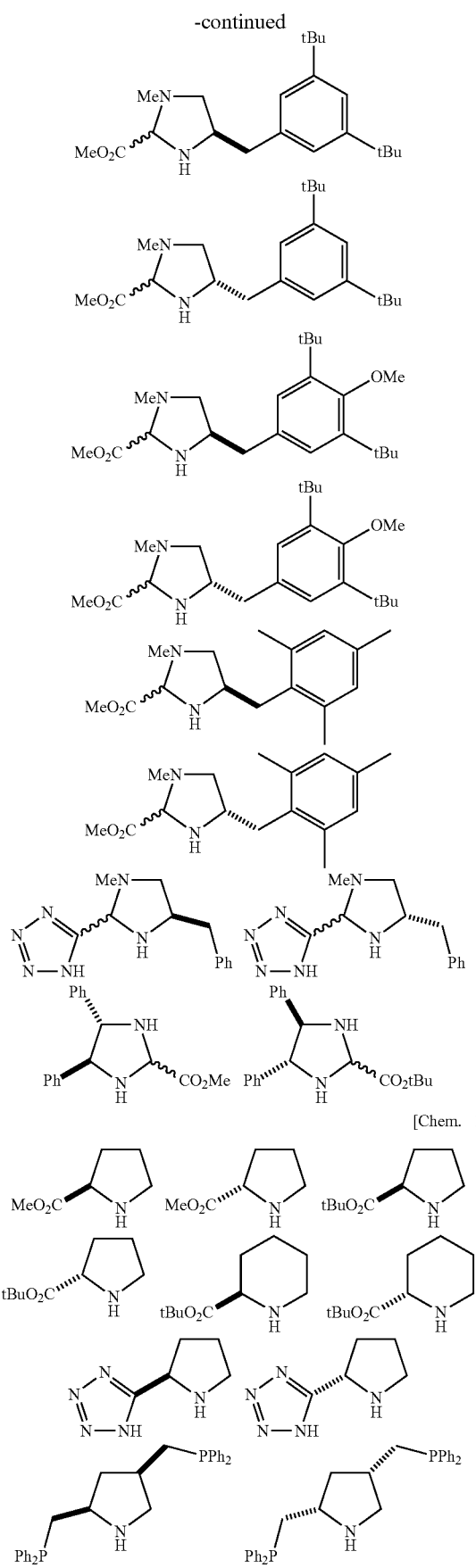
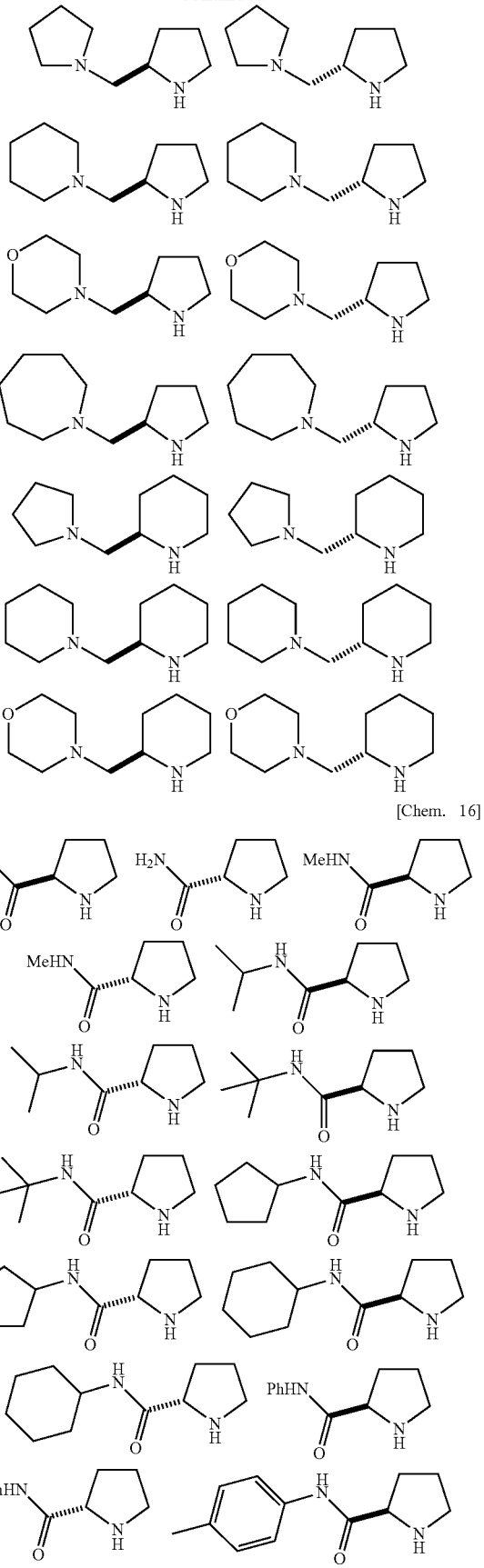

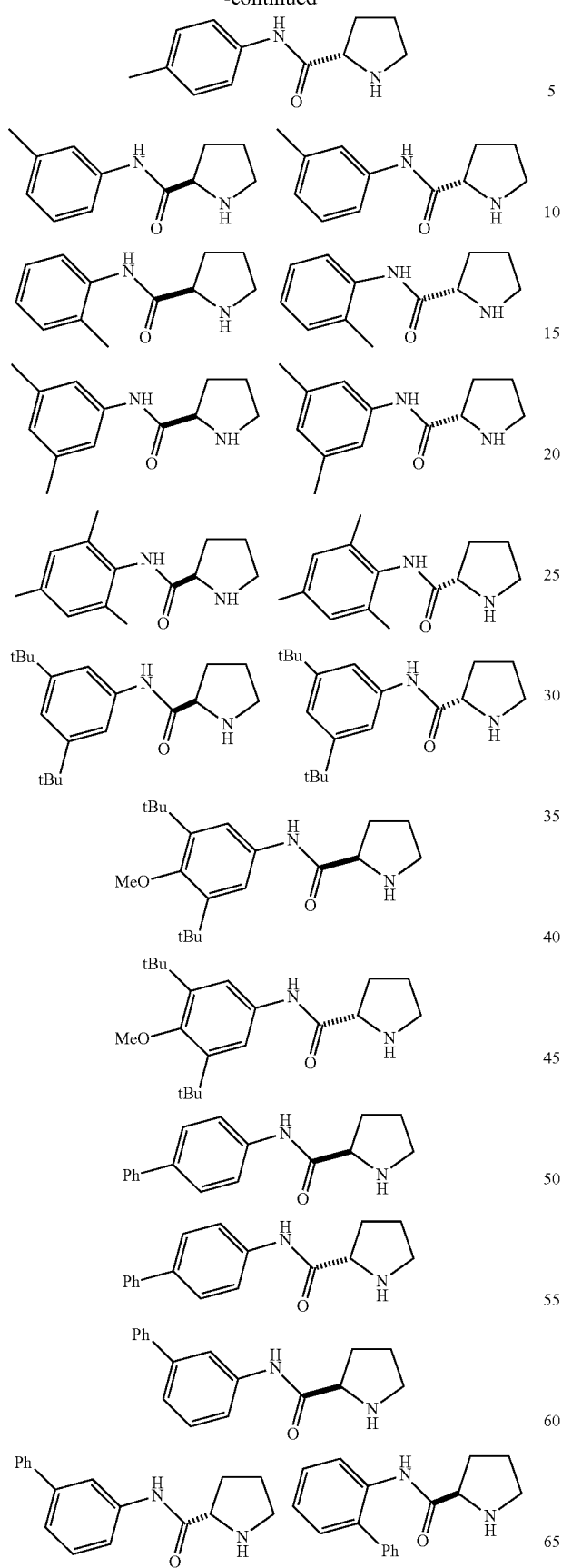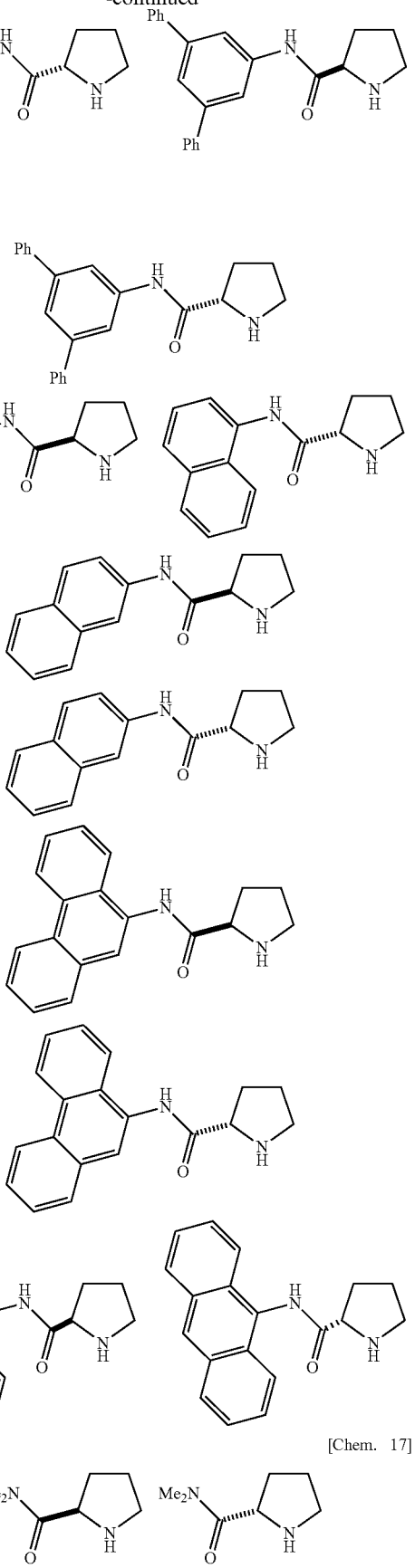

-continued
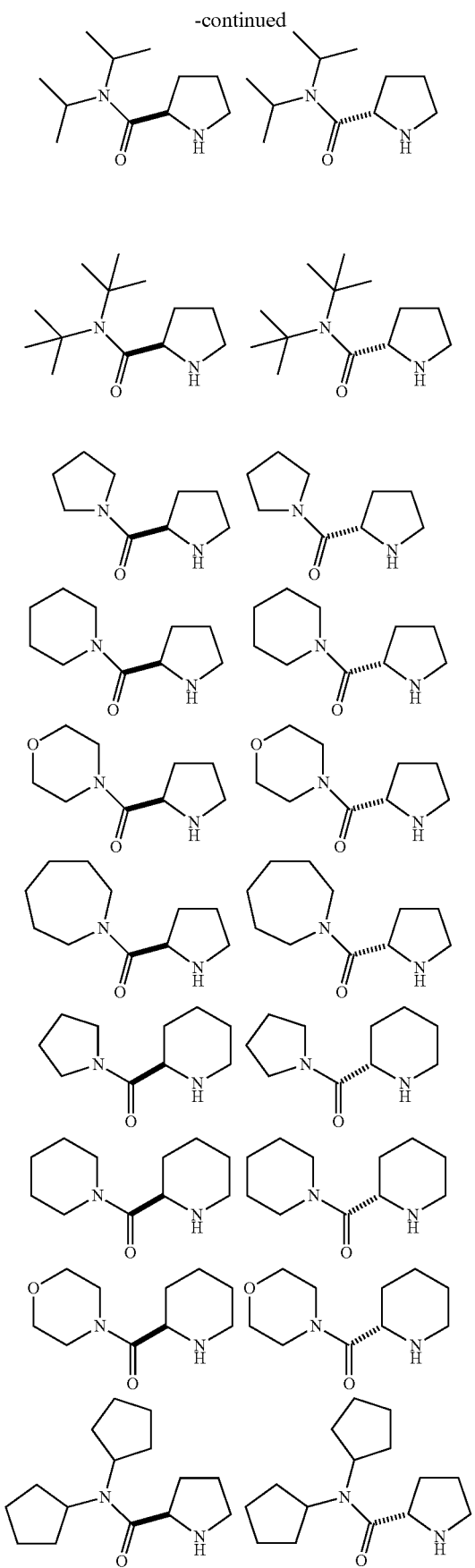
-continued
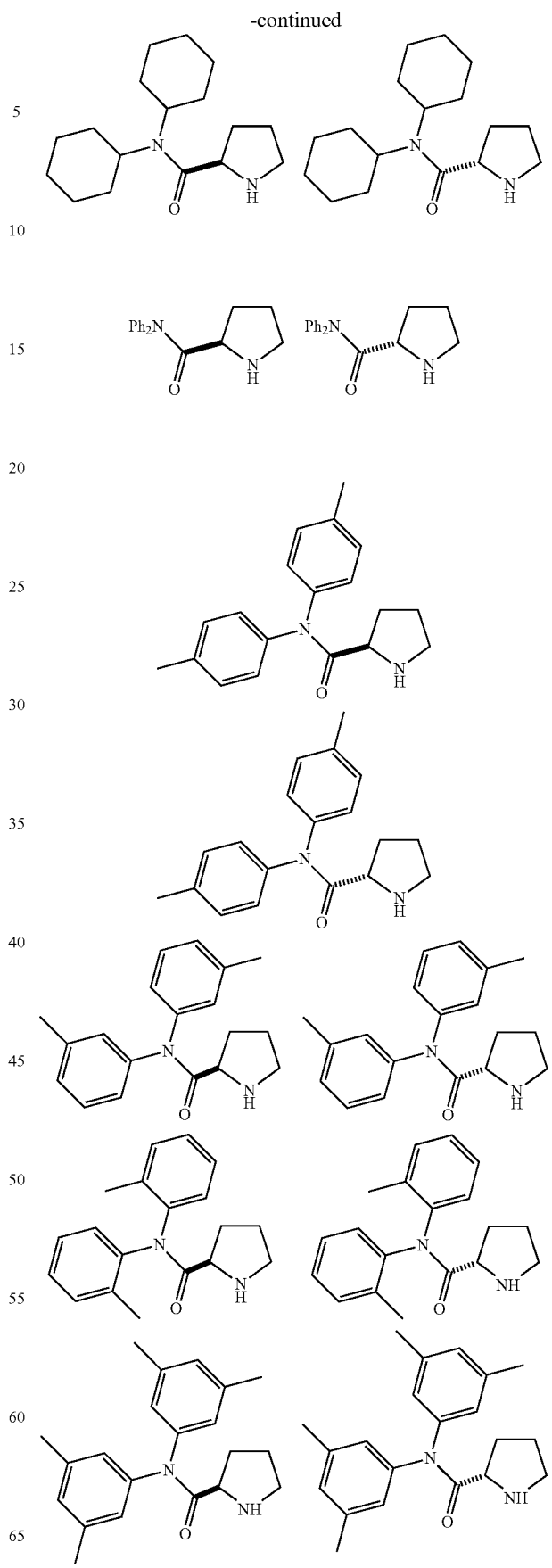

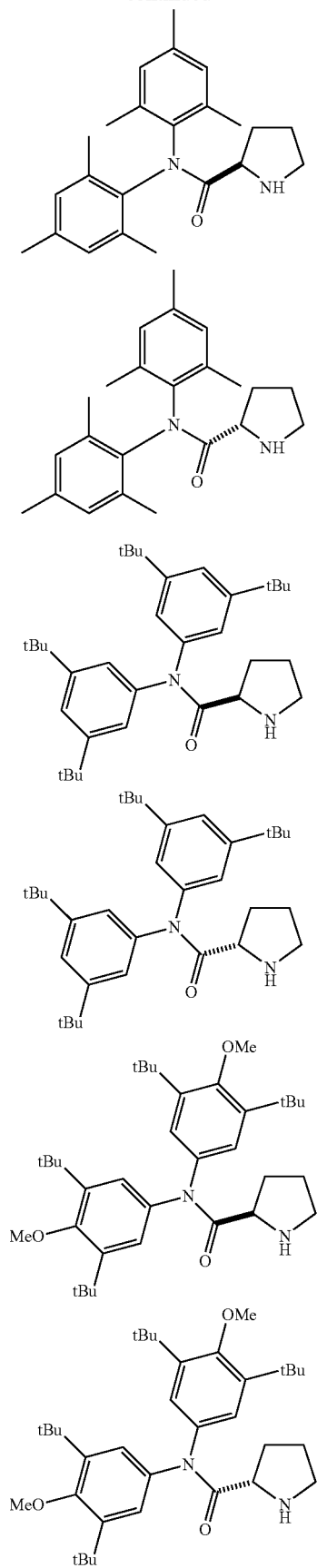
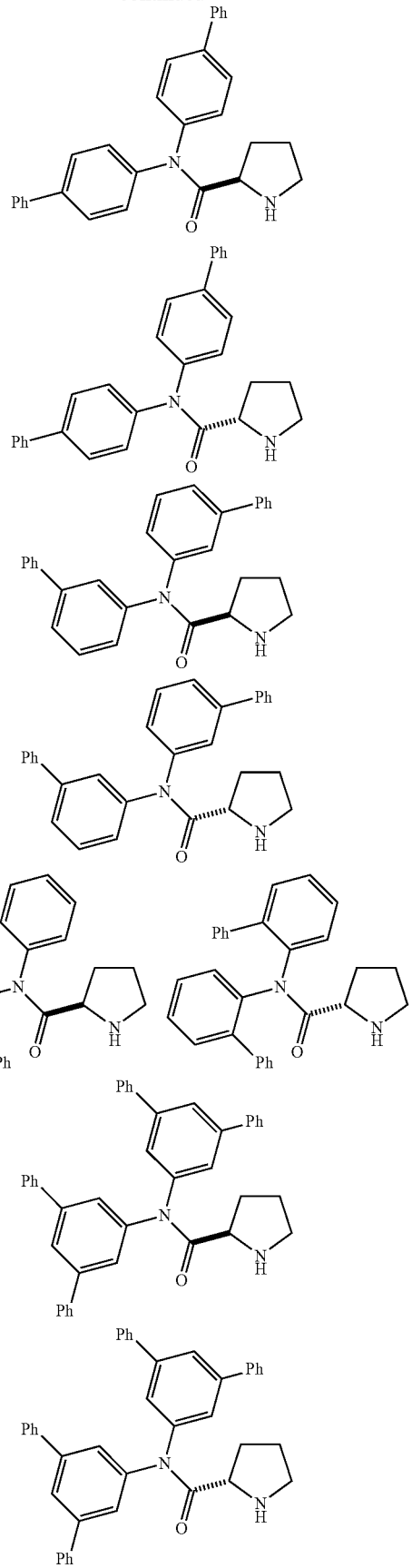

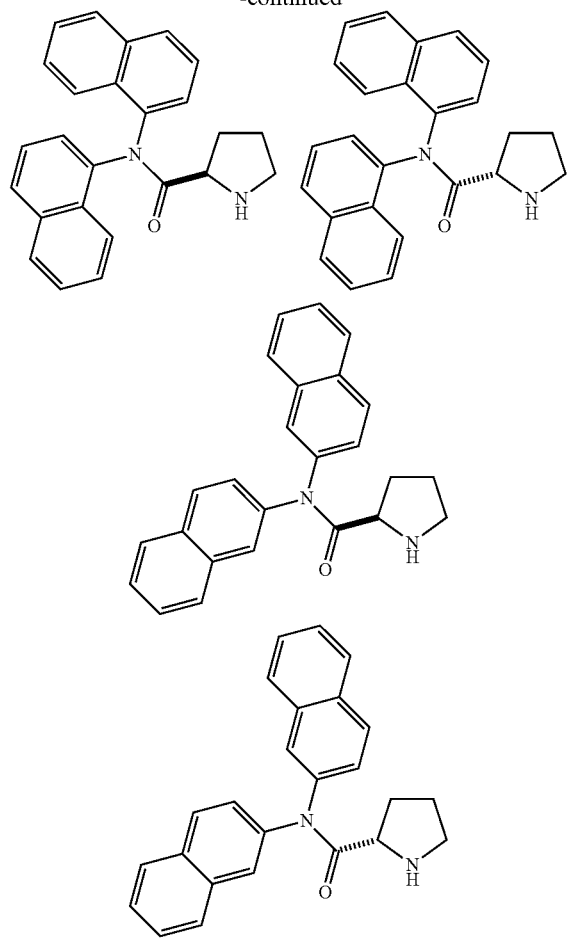
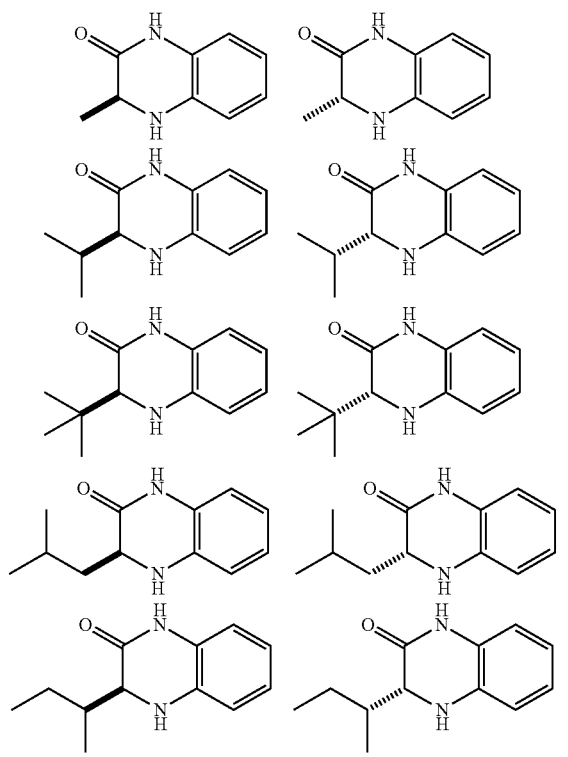
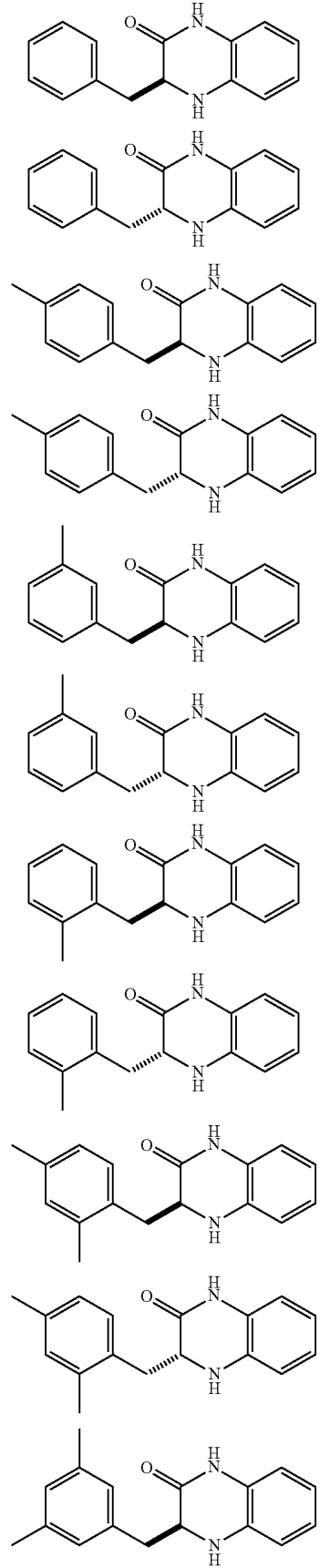

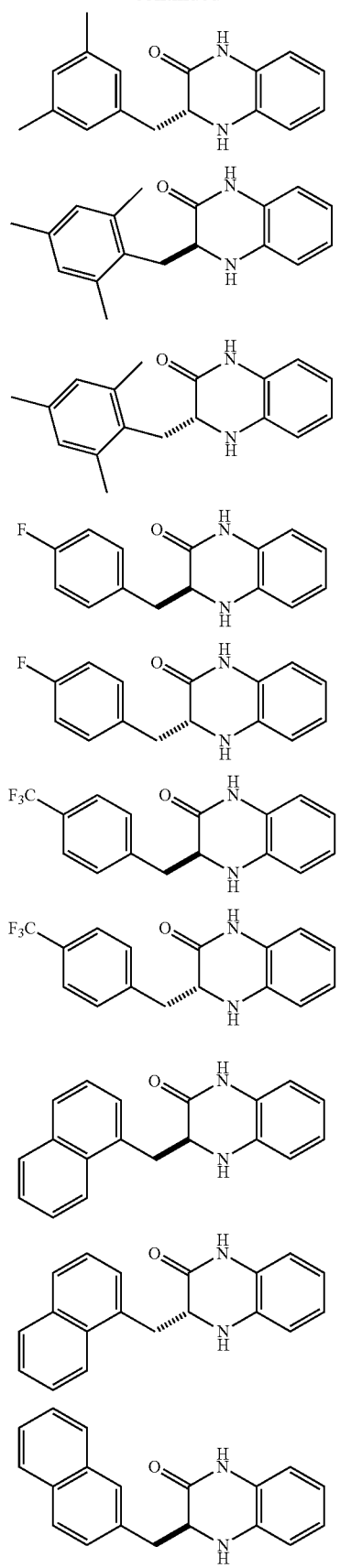
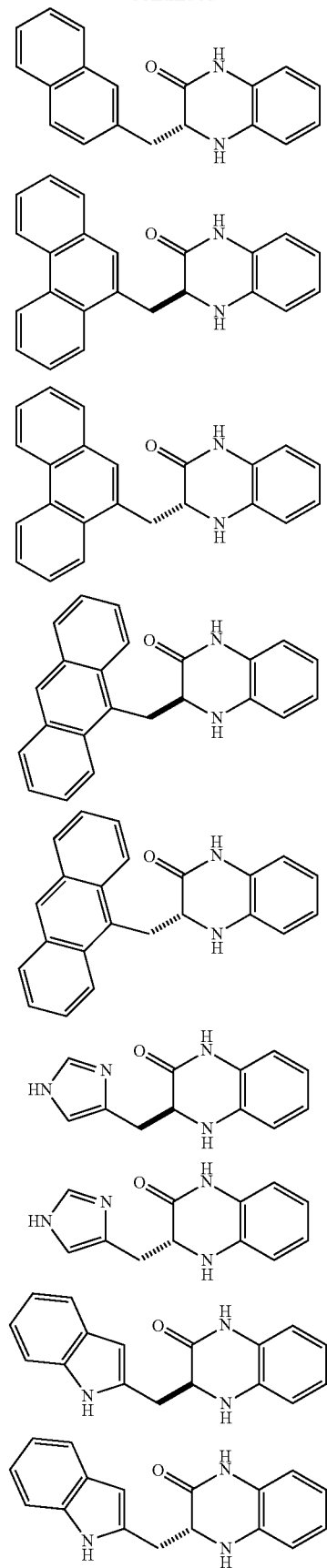
[Chem. 20]

[Chem. 21]
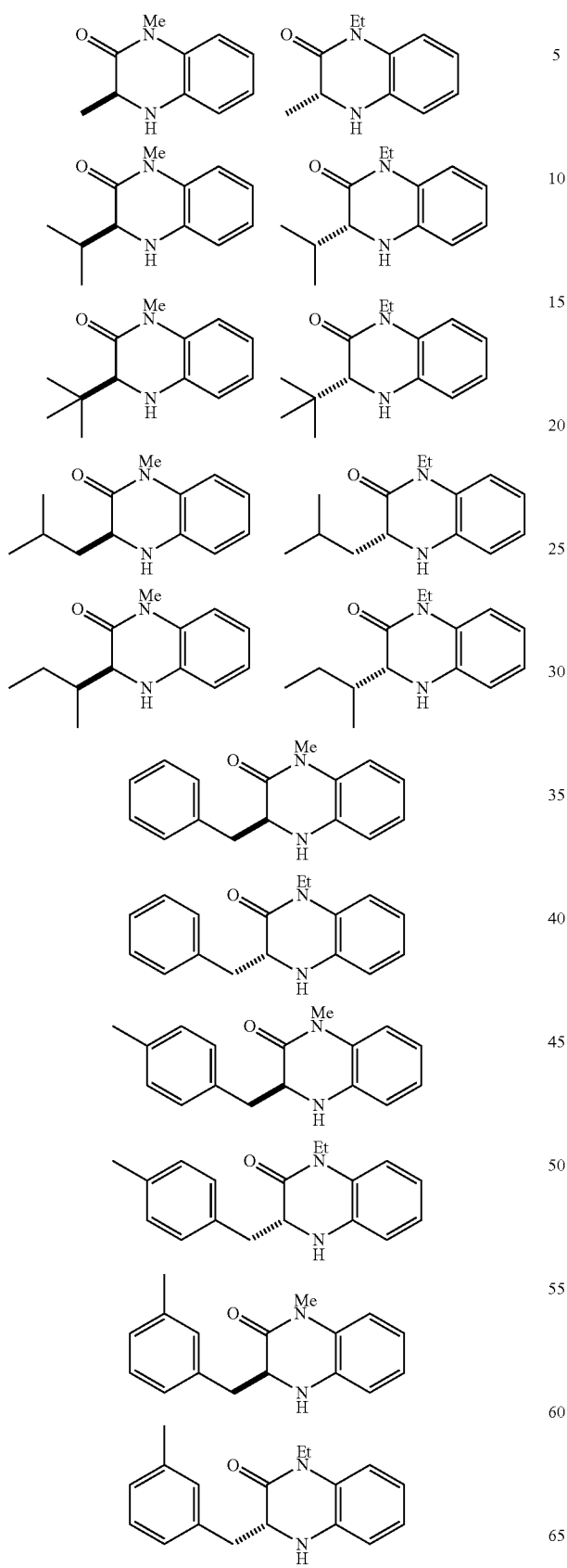
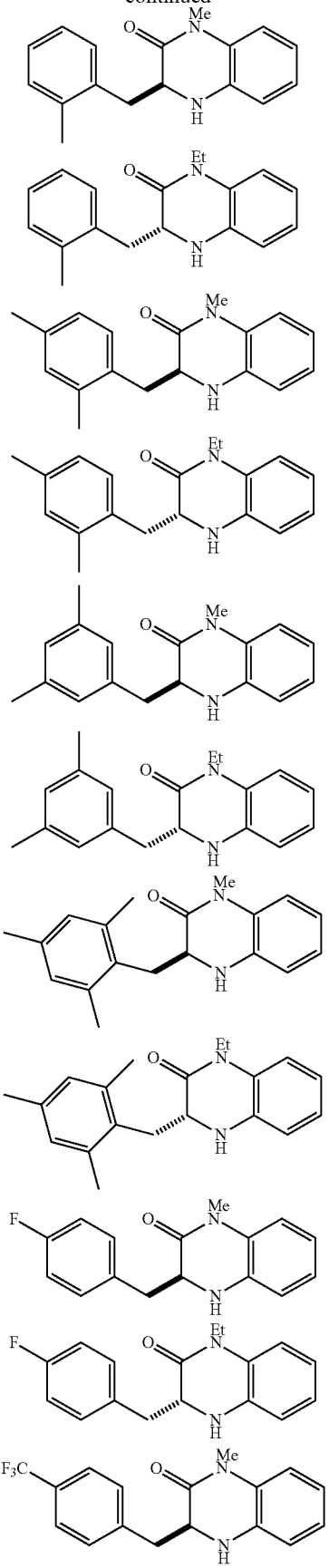

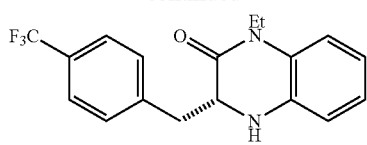
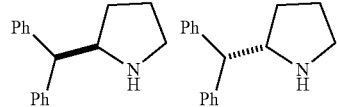
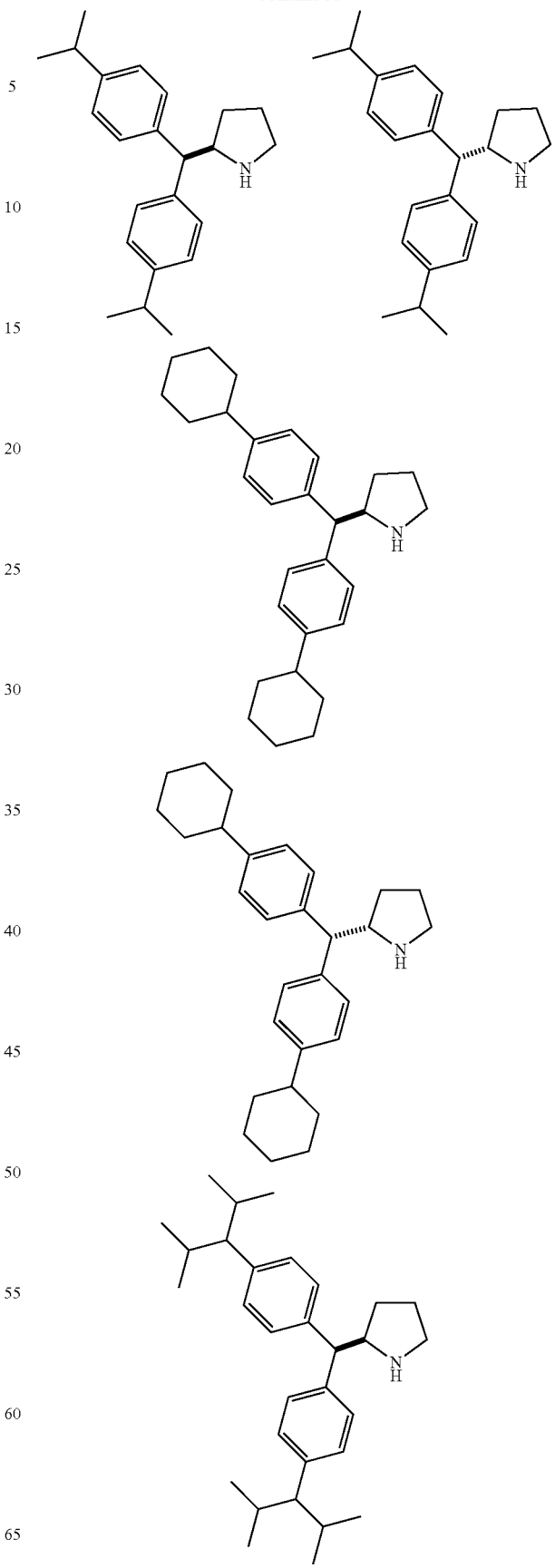

47
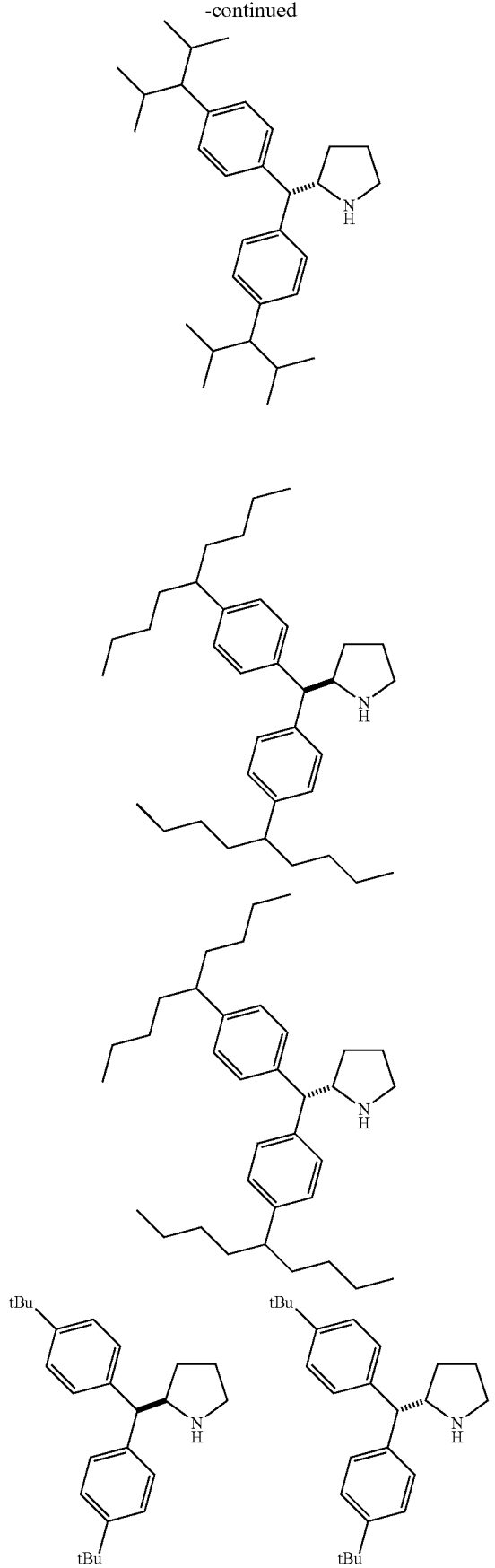
48
-continued
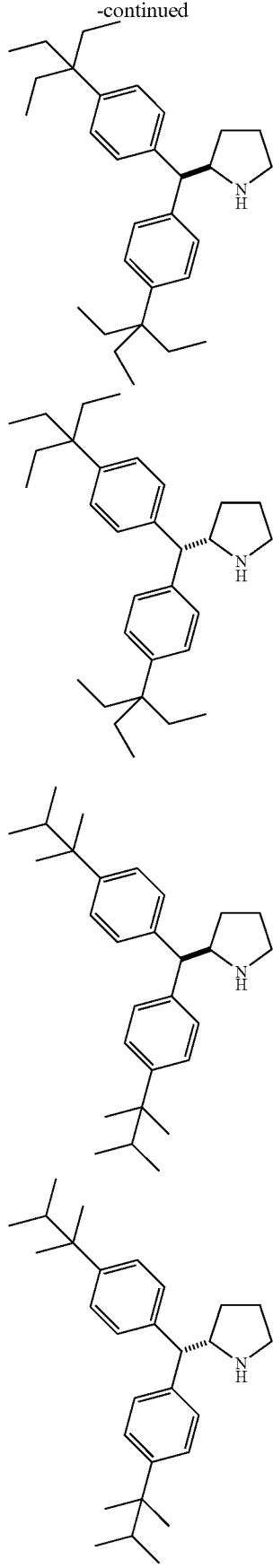
[Chem. 23]

-continued
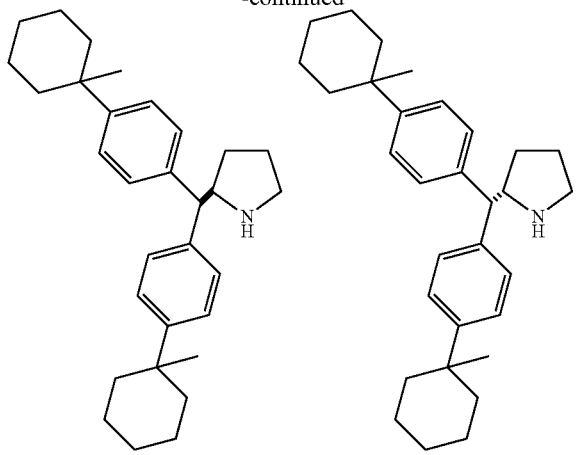
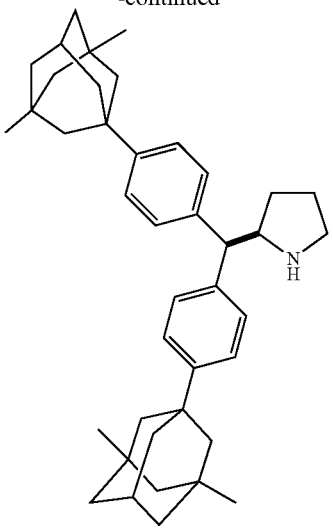
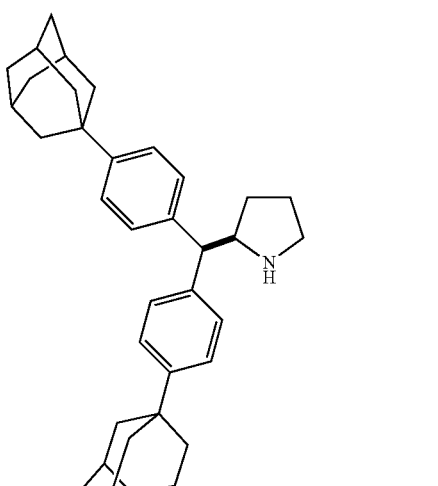
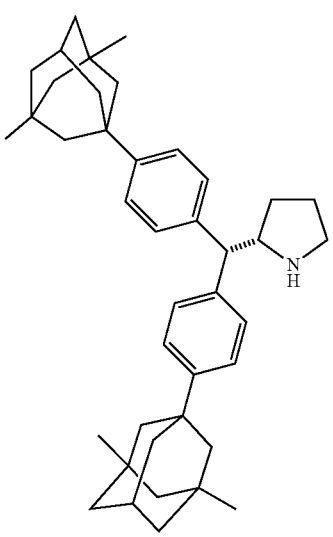
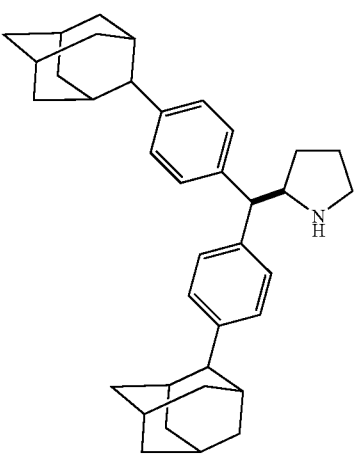

51
-continued
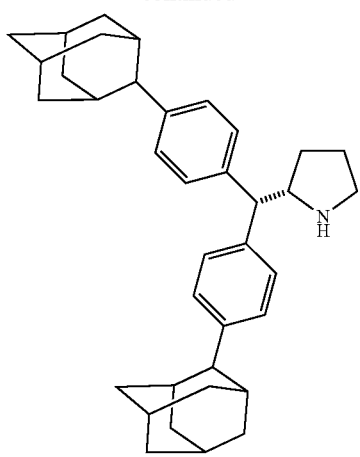
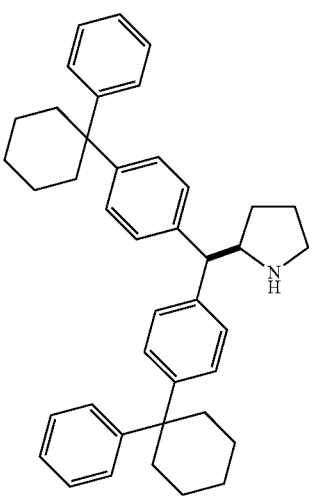
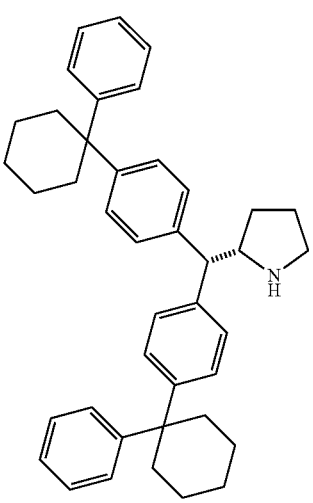
52
-continued
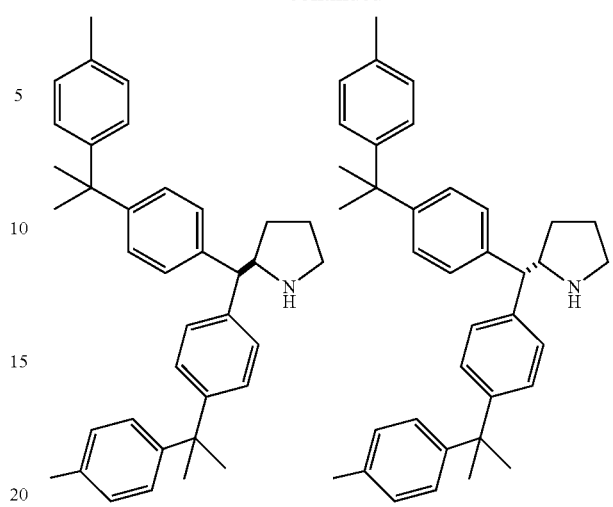
[Chem. 24]
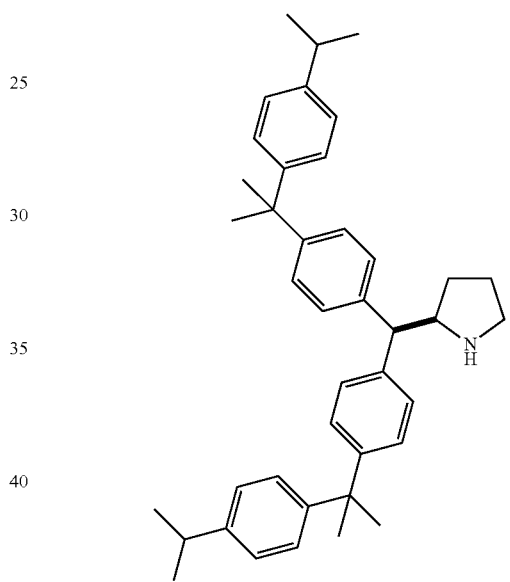
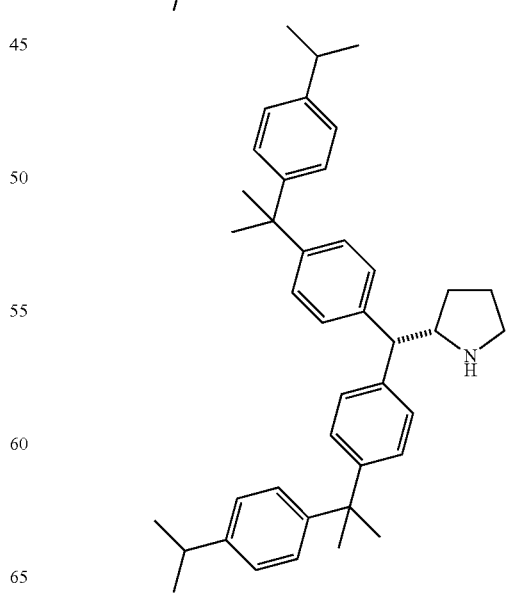

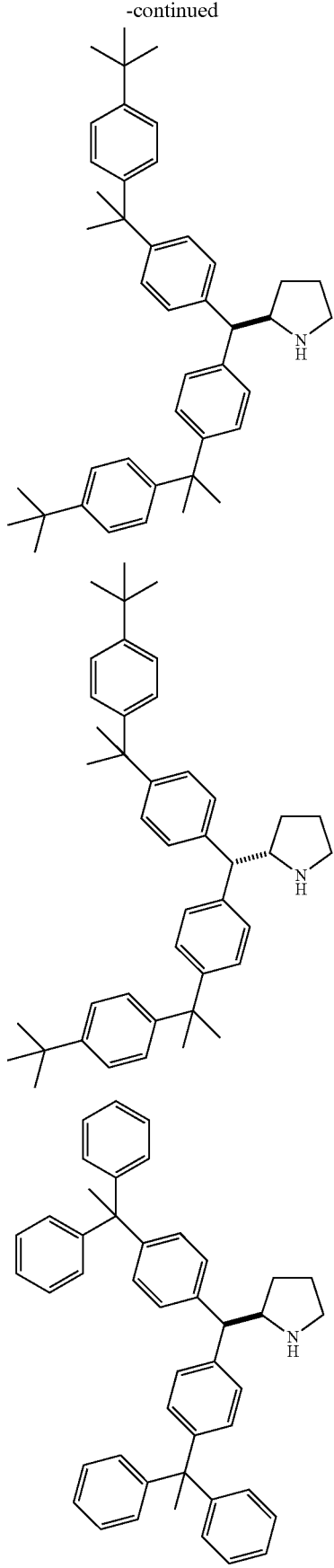
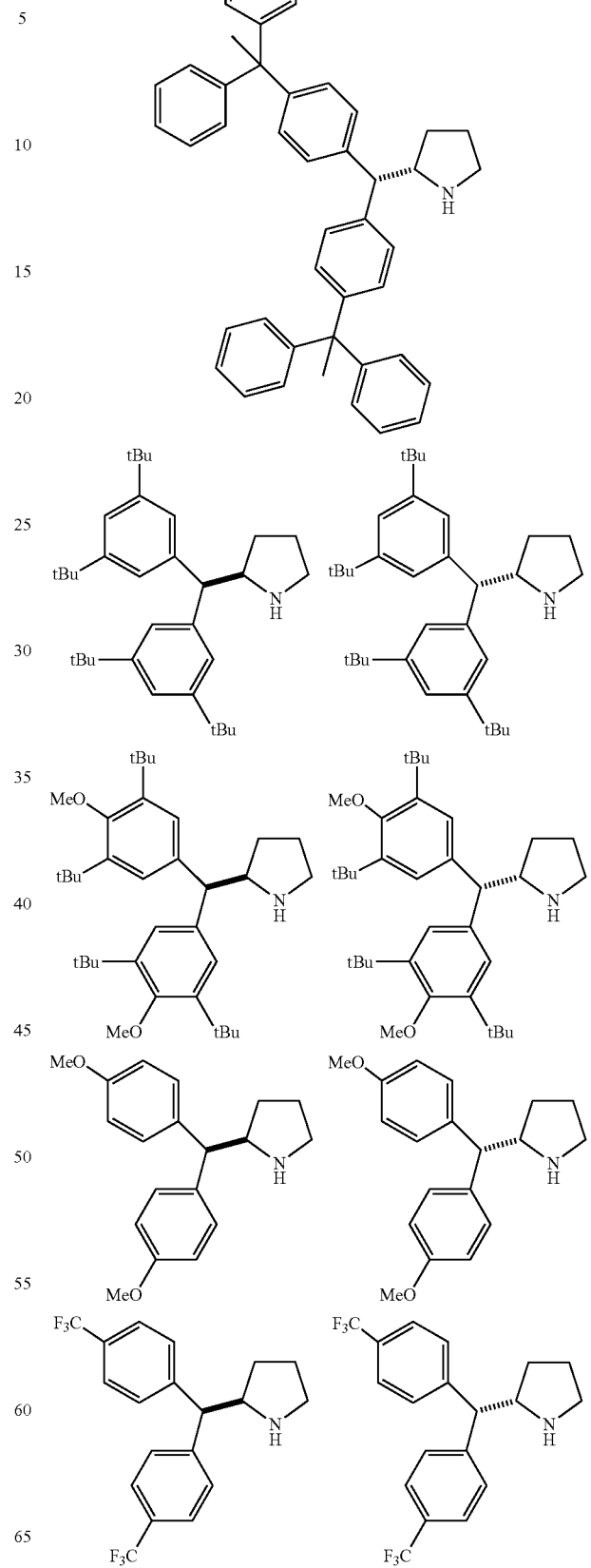

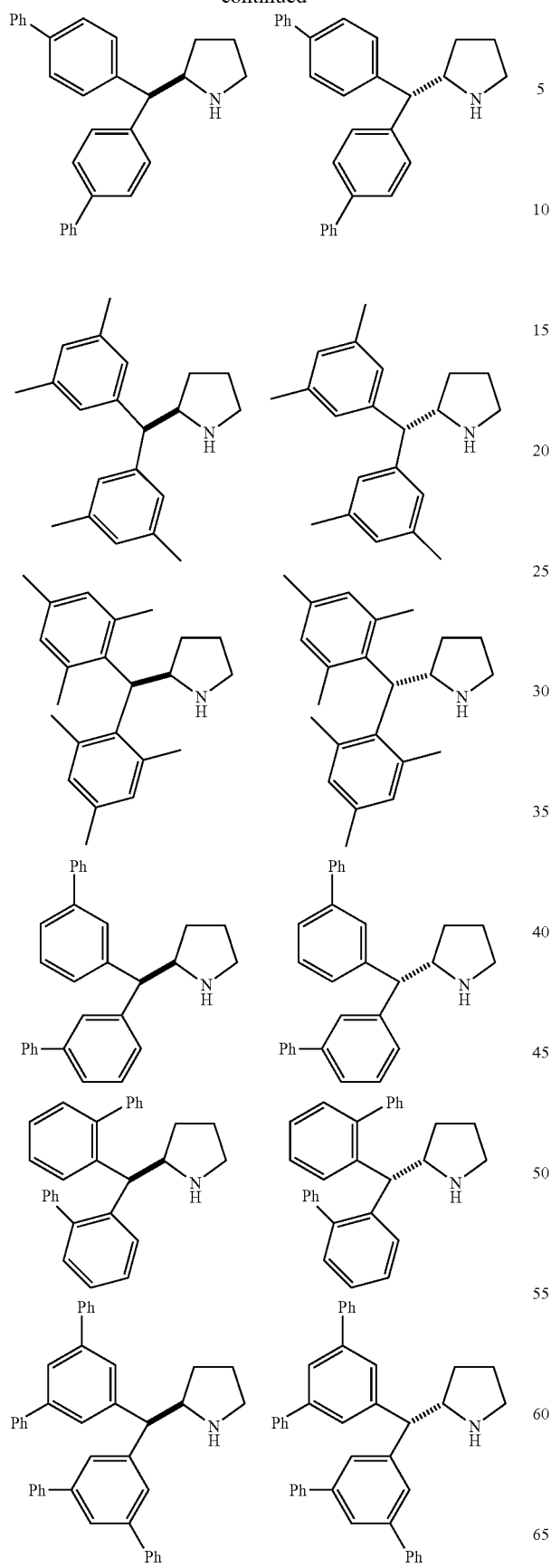
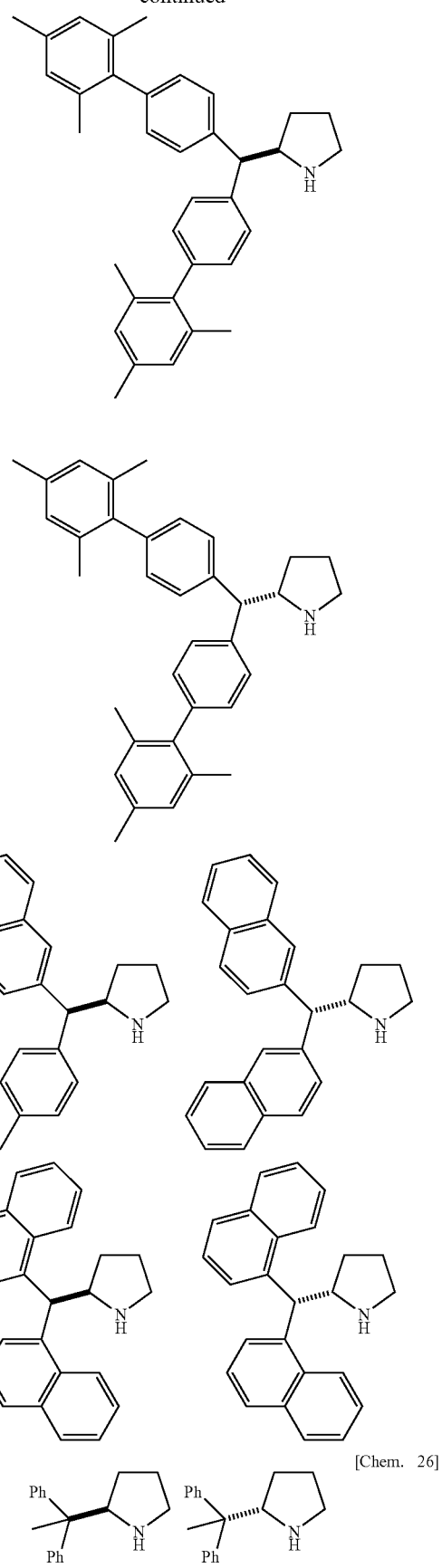
[Chem. 26]

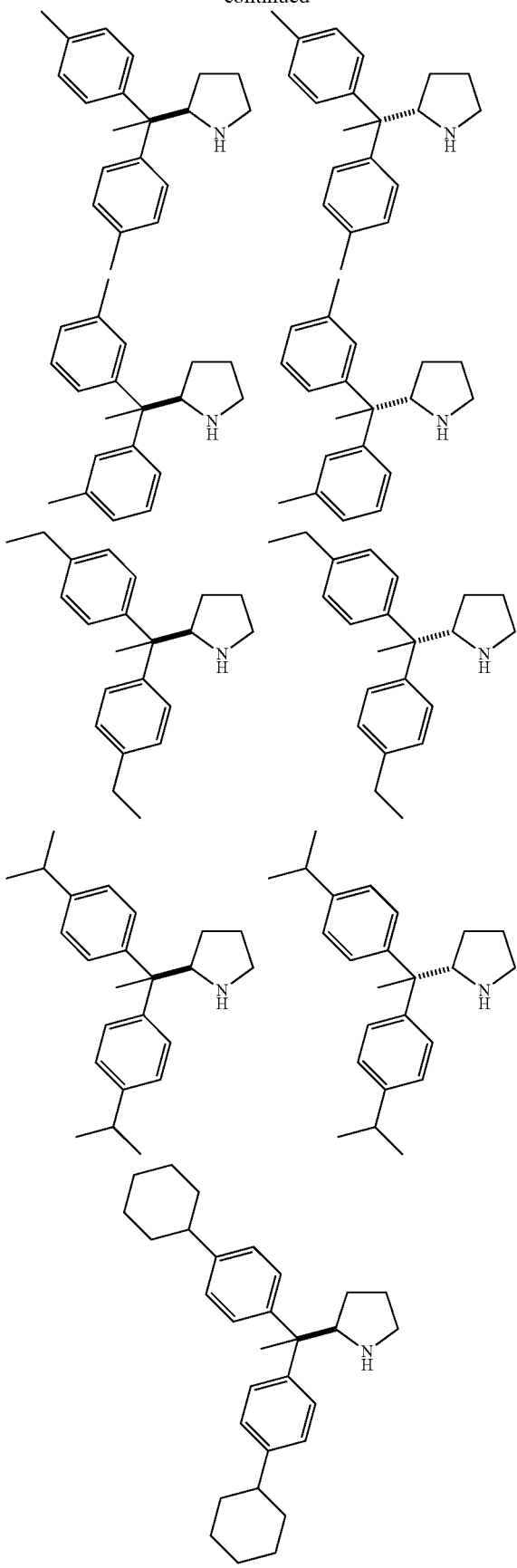
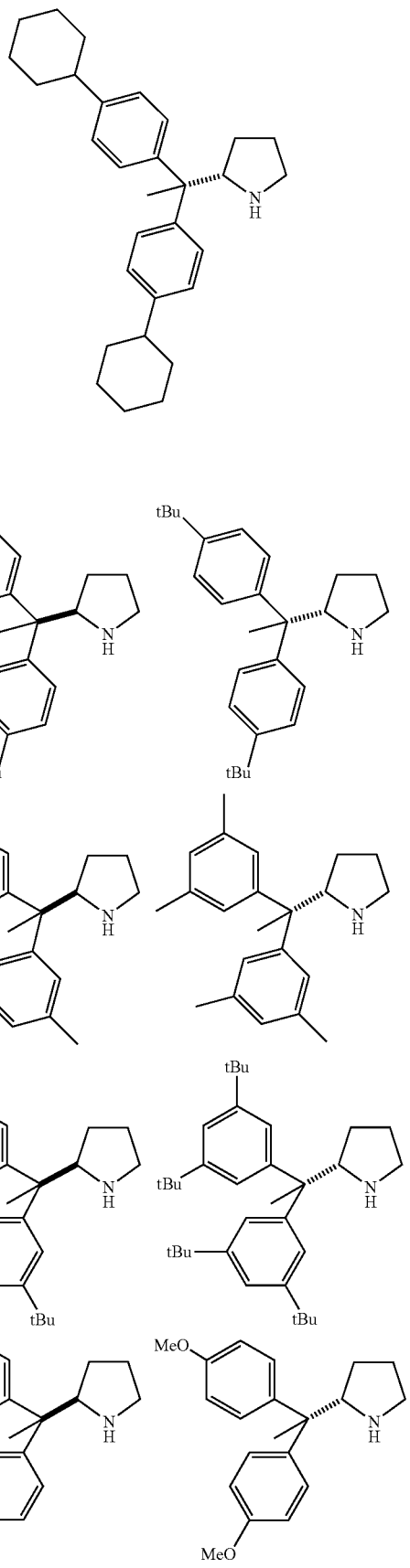

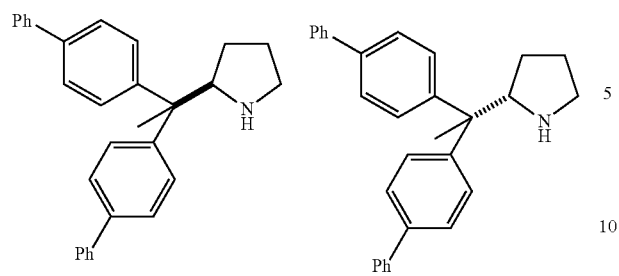
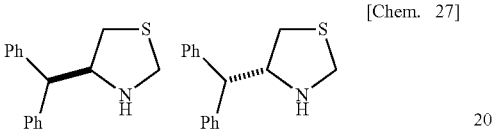
[Chem. 27]
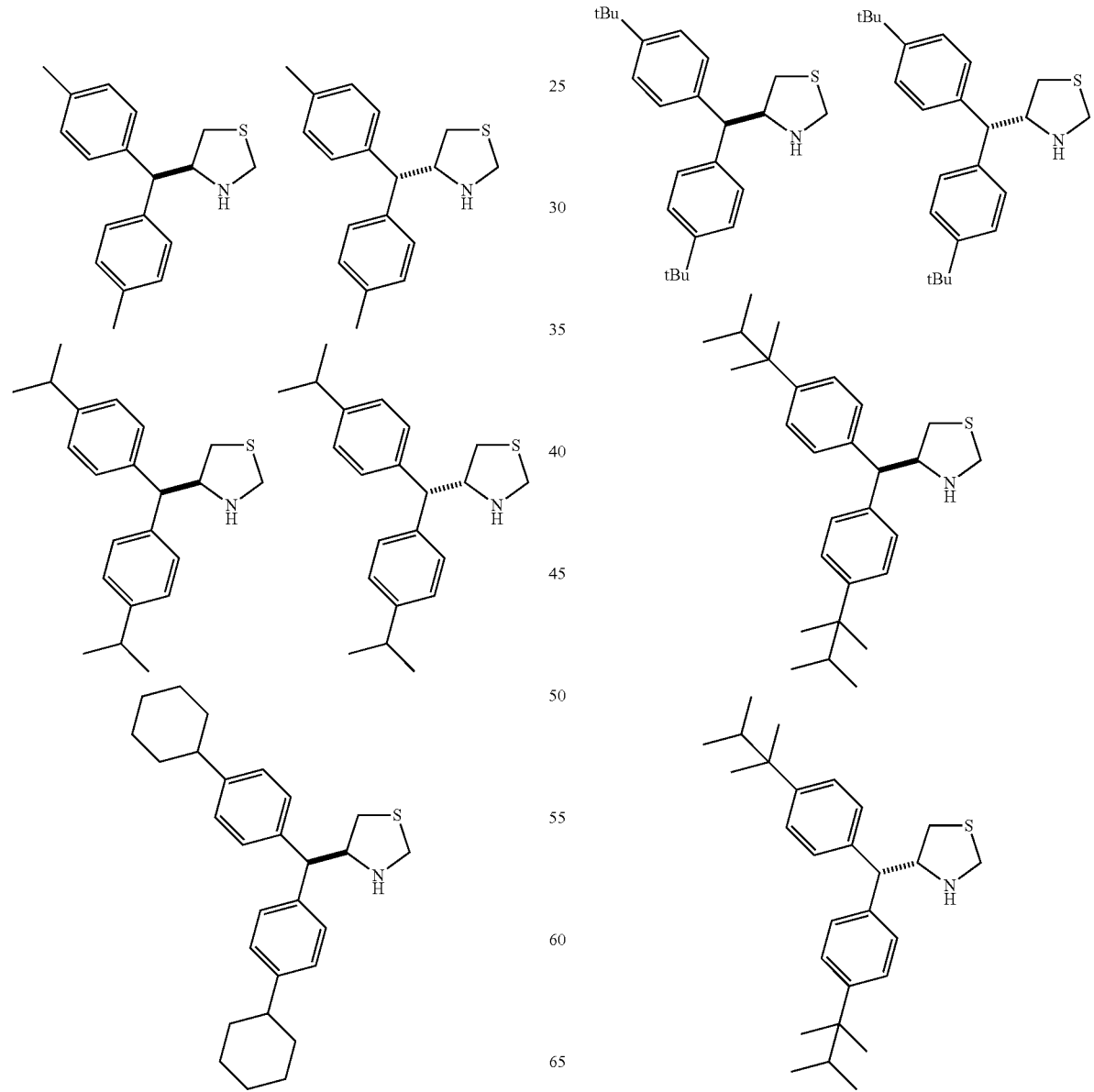

61
-continued
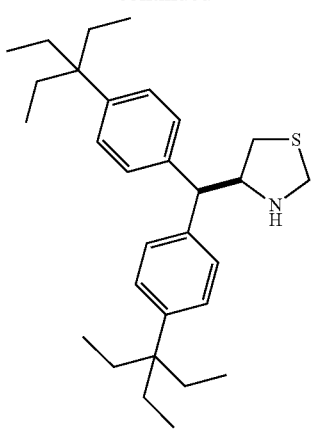
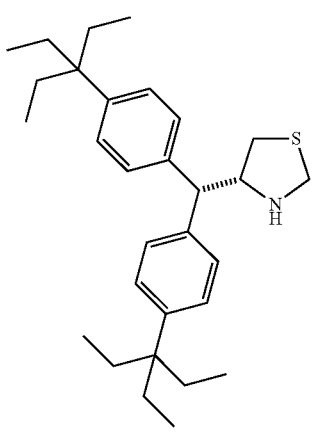
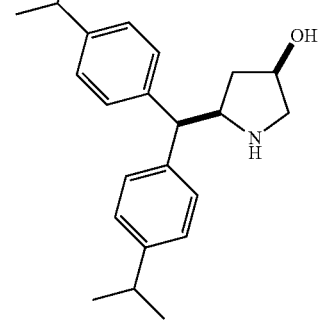
62
-continued
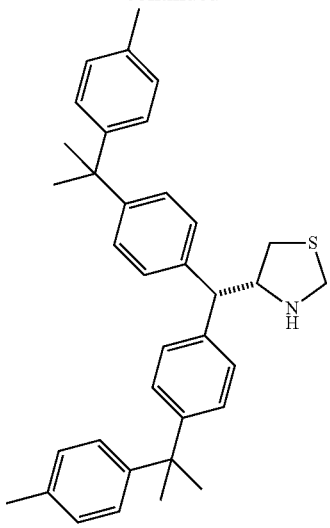
[Chem. 28]
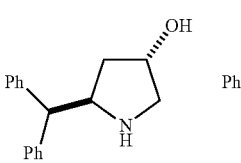 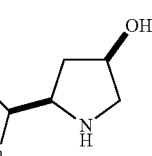
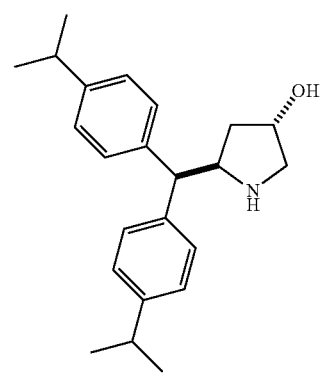

63
-continued
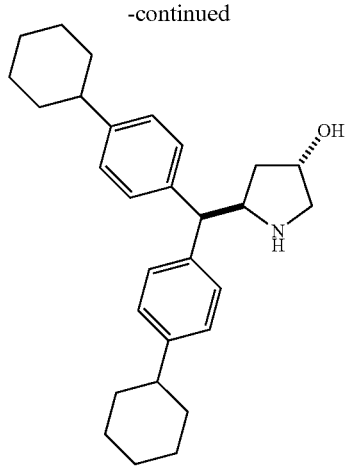
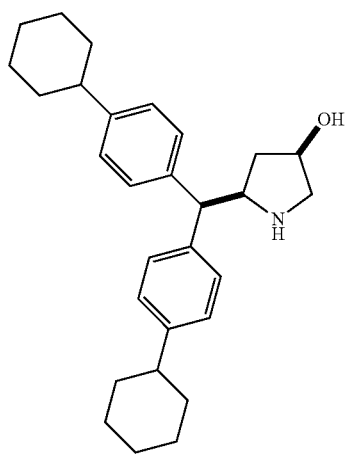
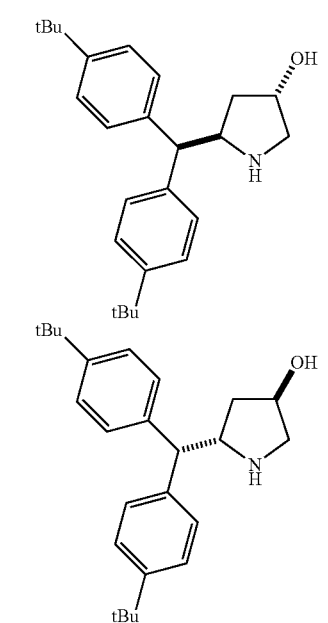
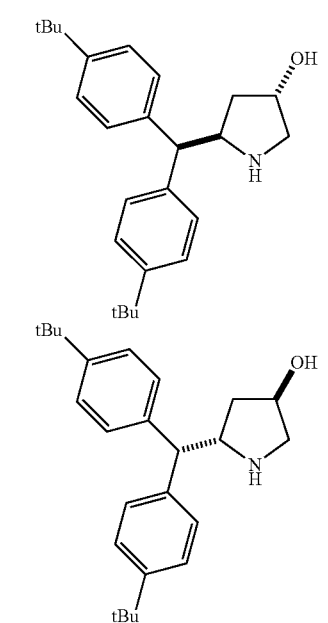
64
-continued
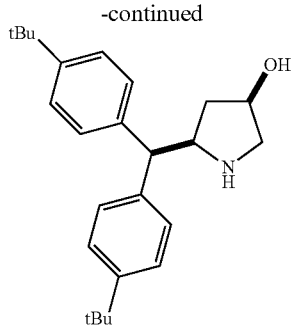
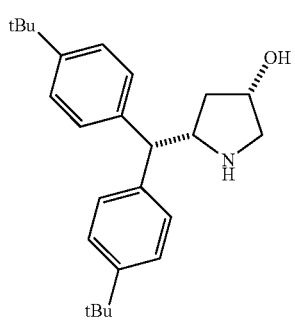
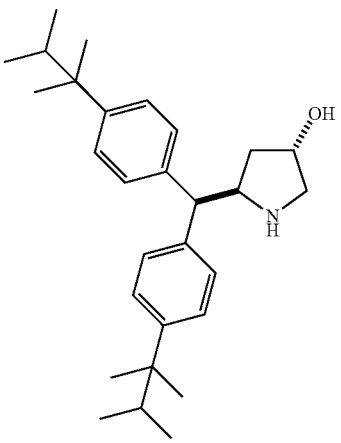
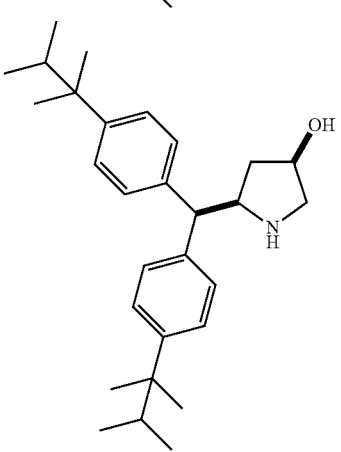

65
-continued
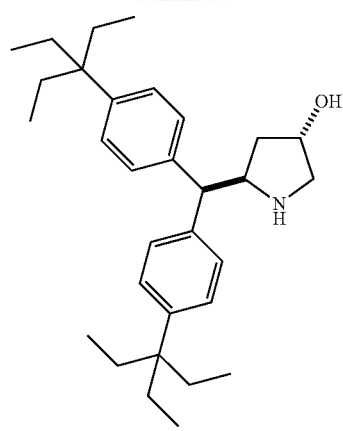
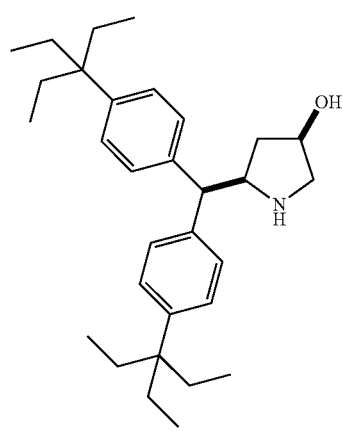
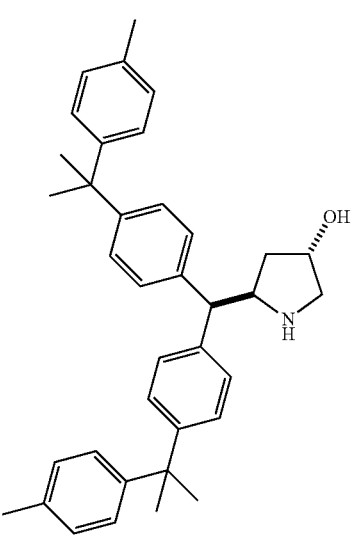
66
-continued
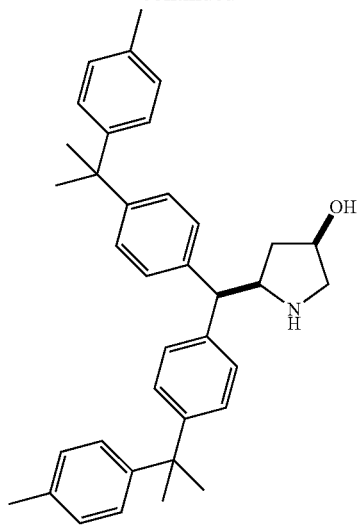
[Chem. 29]
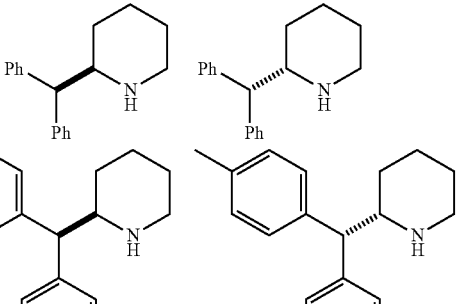
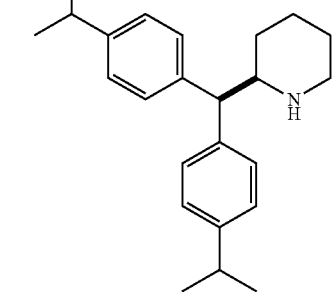
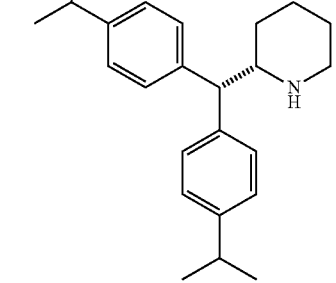

67
-continued
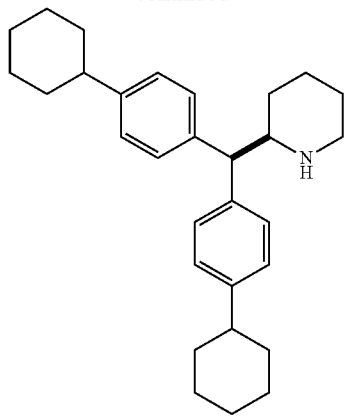
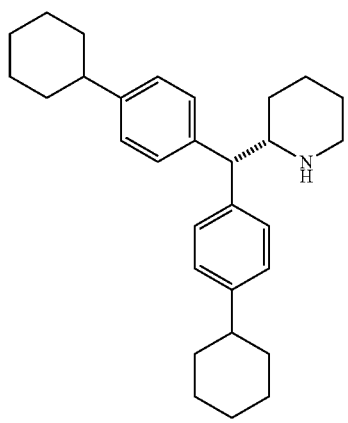
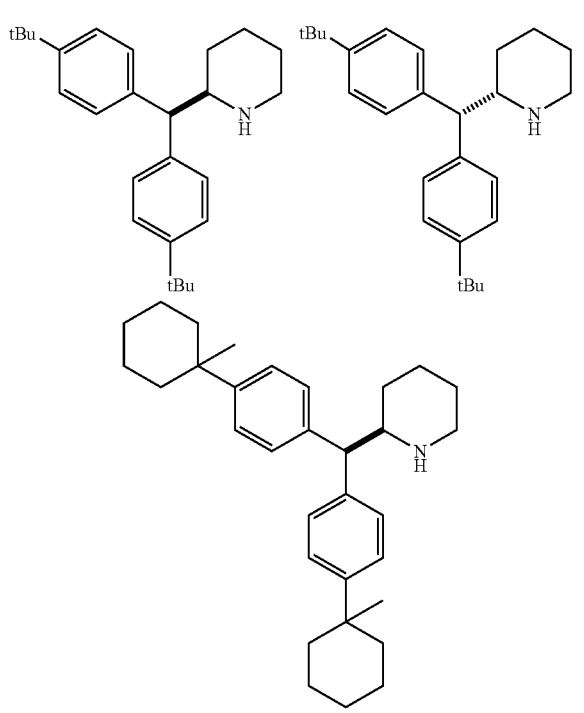
68
-continued
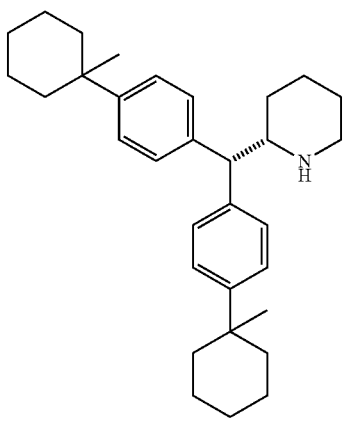
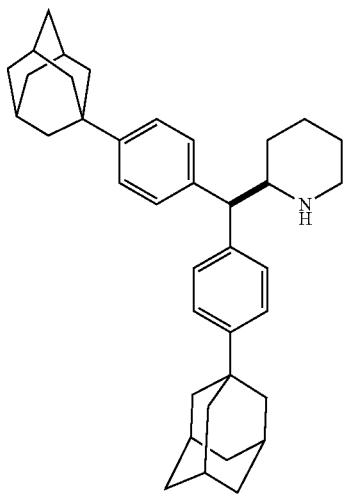
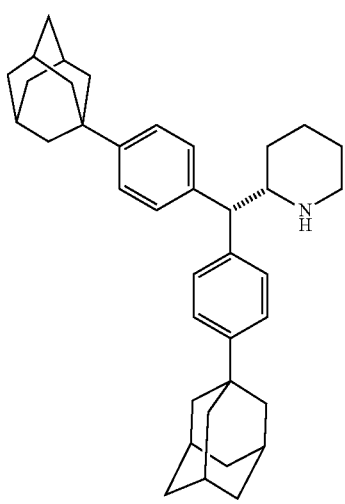

-continued
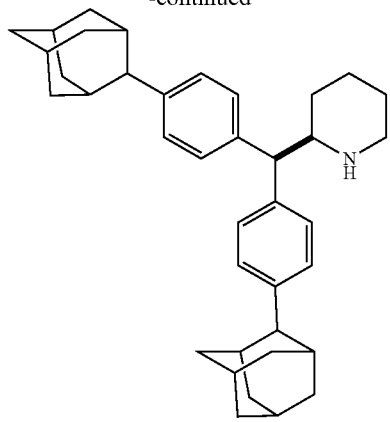
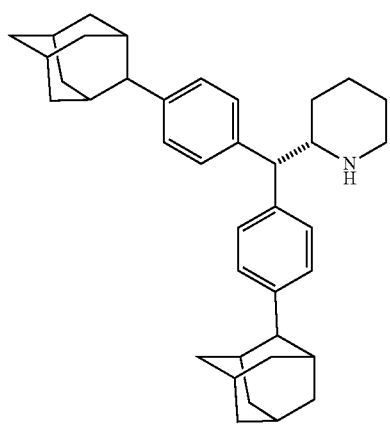
[Chem. 30]
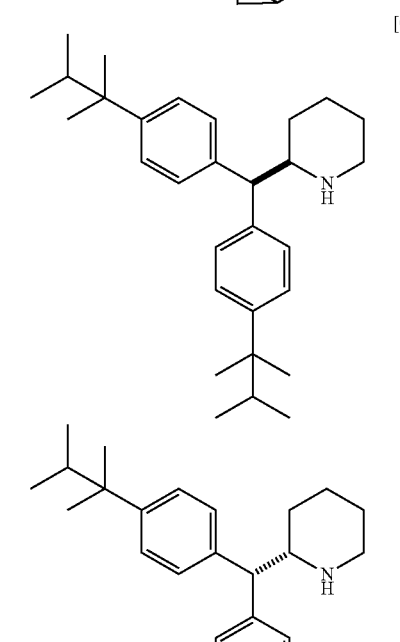
-continued
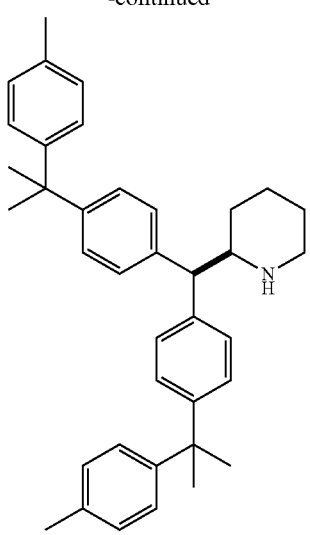
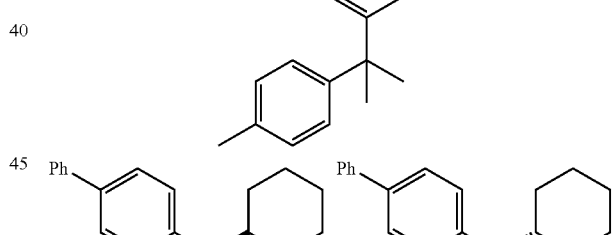
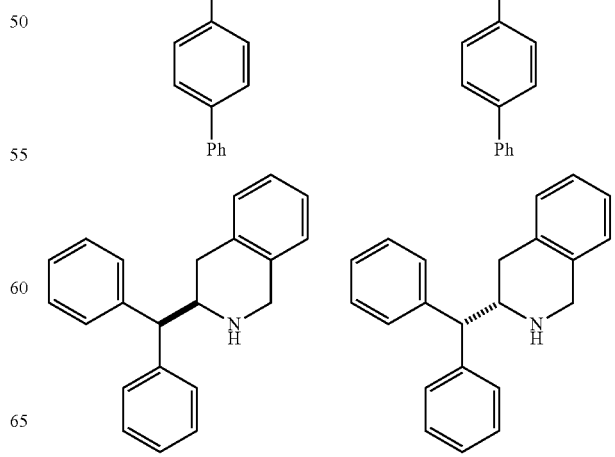

71
-continued
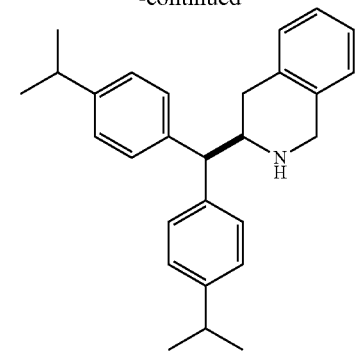
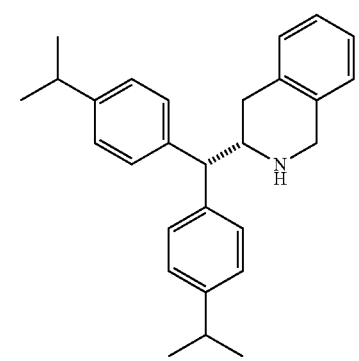
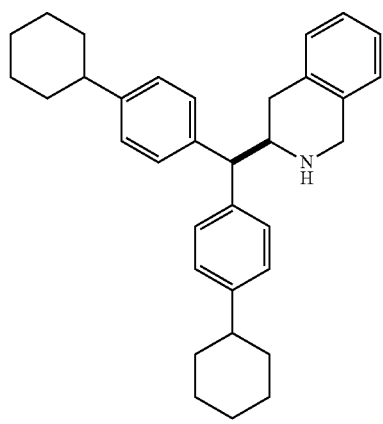
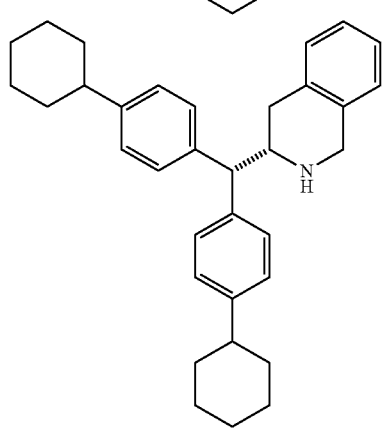
72
-continued
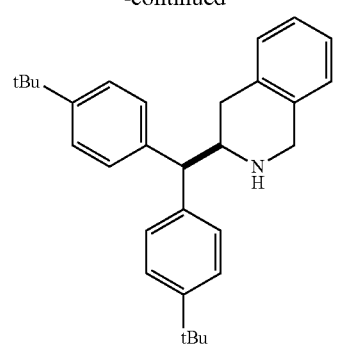
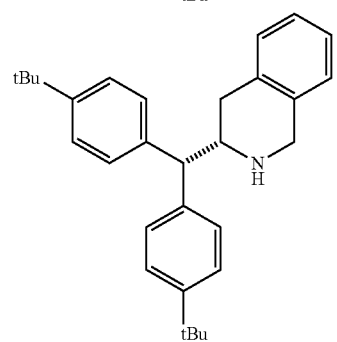
[Chem. 31]
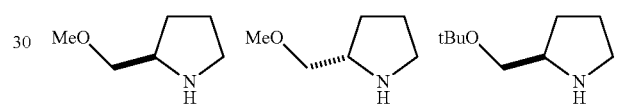
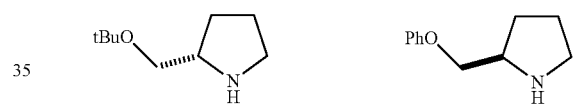
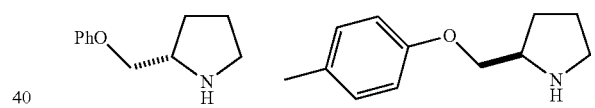
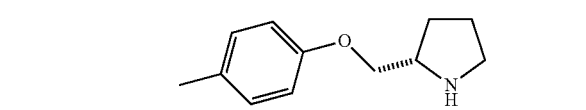
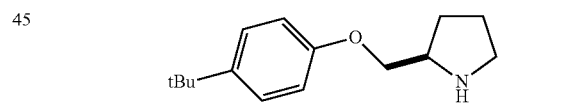
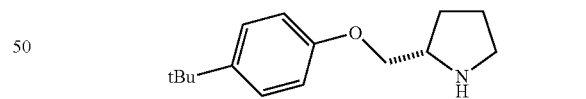
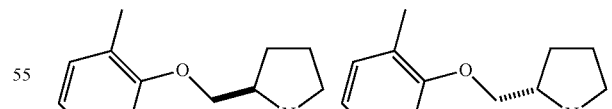
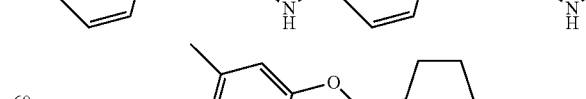
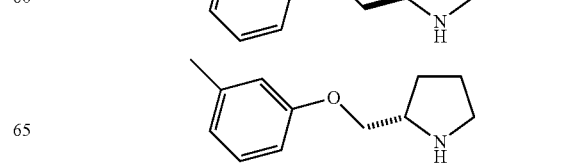

73
-continued
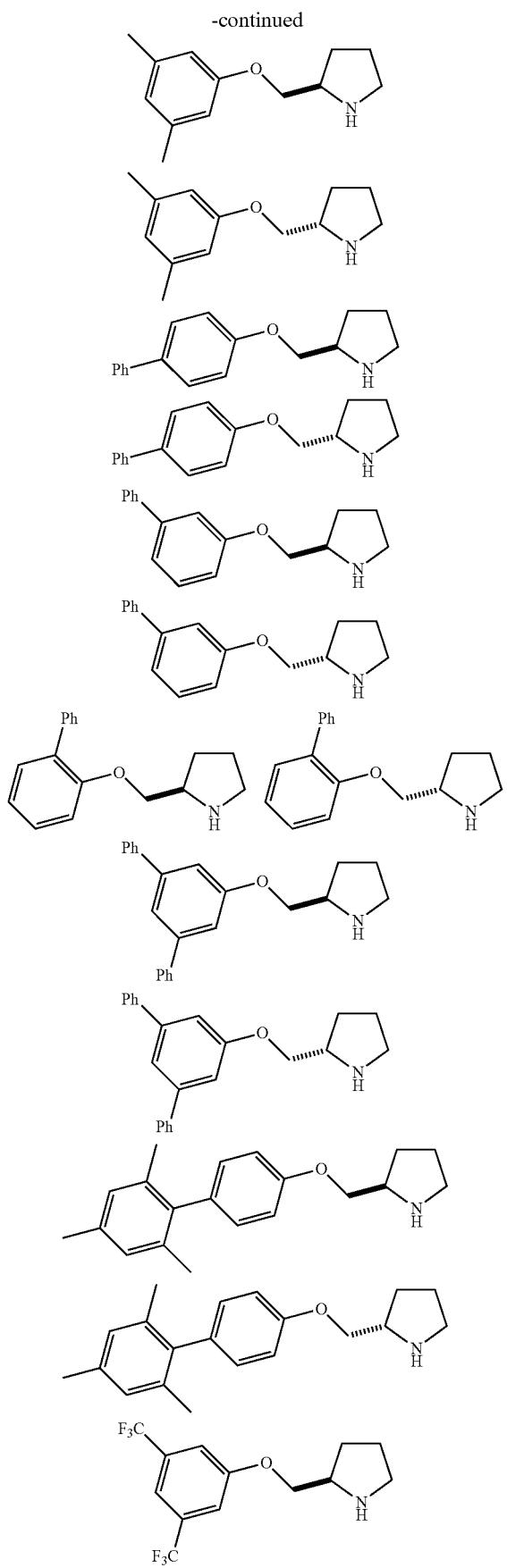
74
-continued
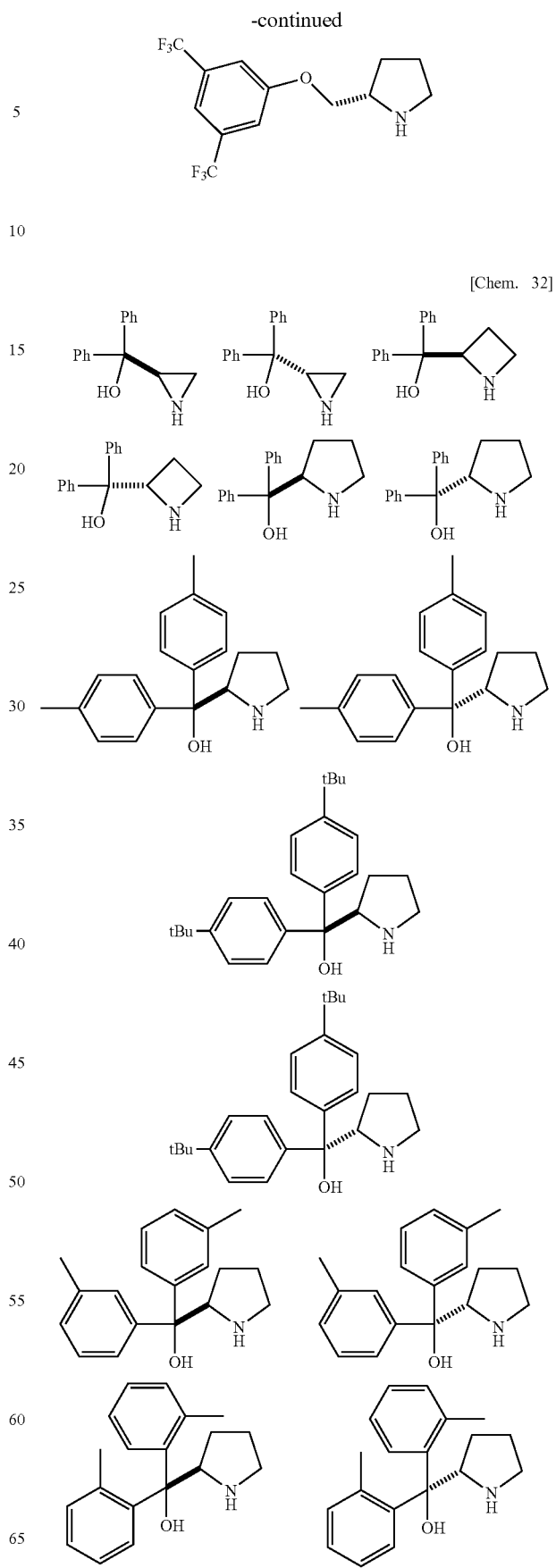
[Chem. 32]

-continued
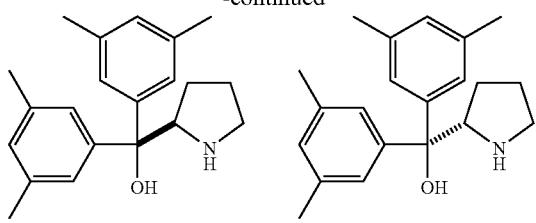
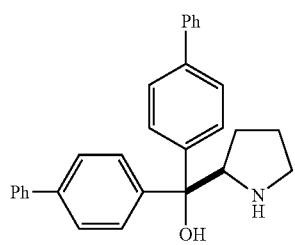
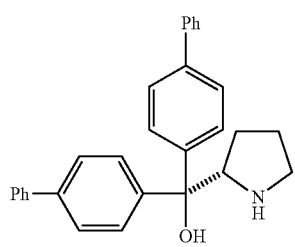
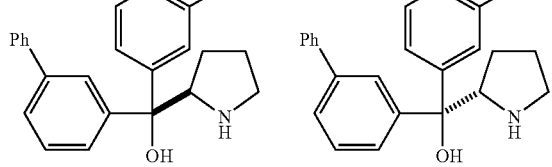
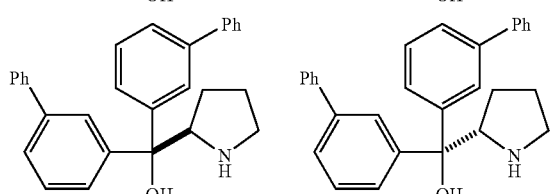
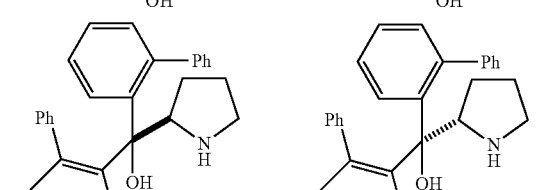
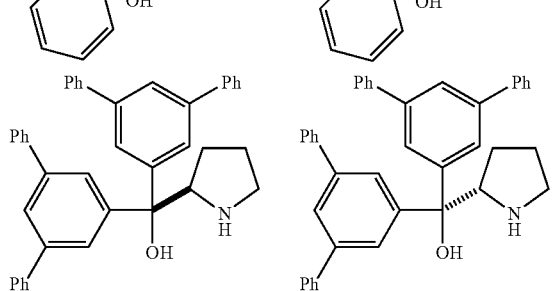
-continued
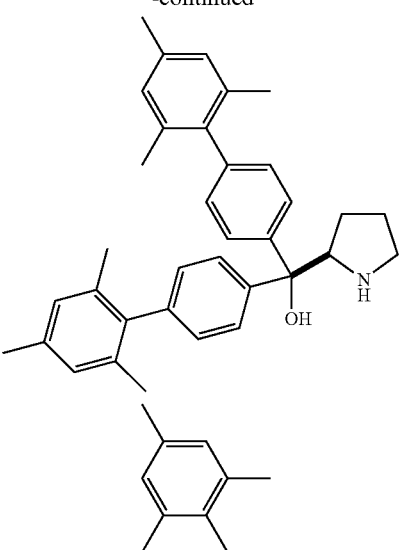
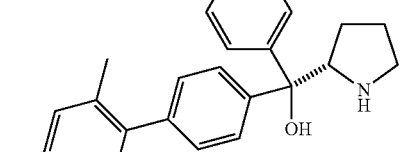
[Chem. 33]
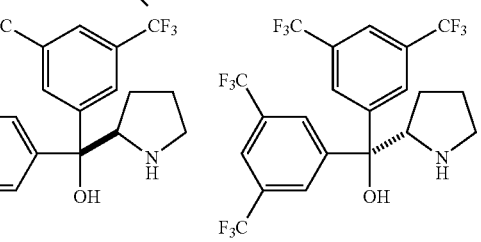
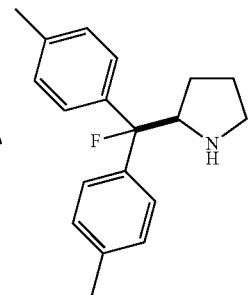
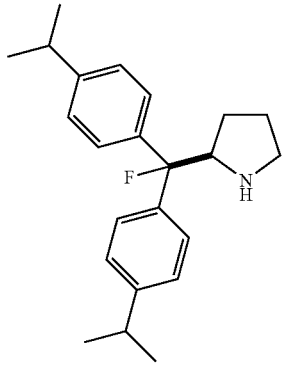

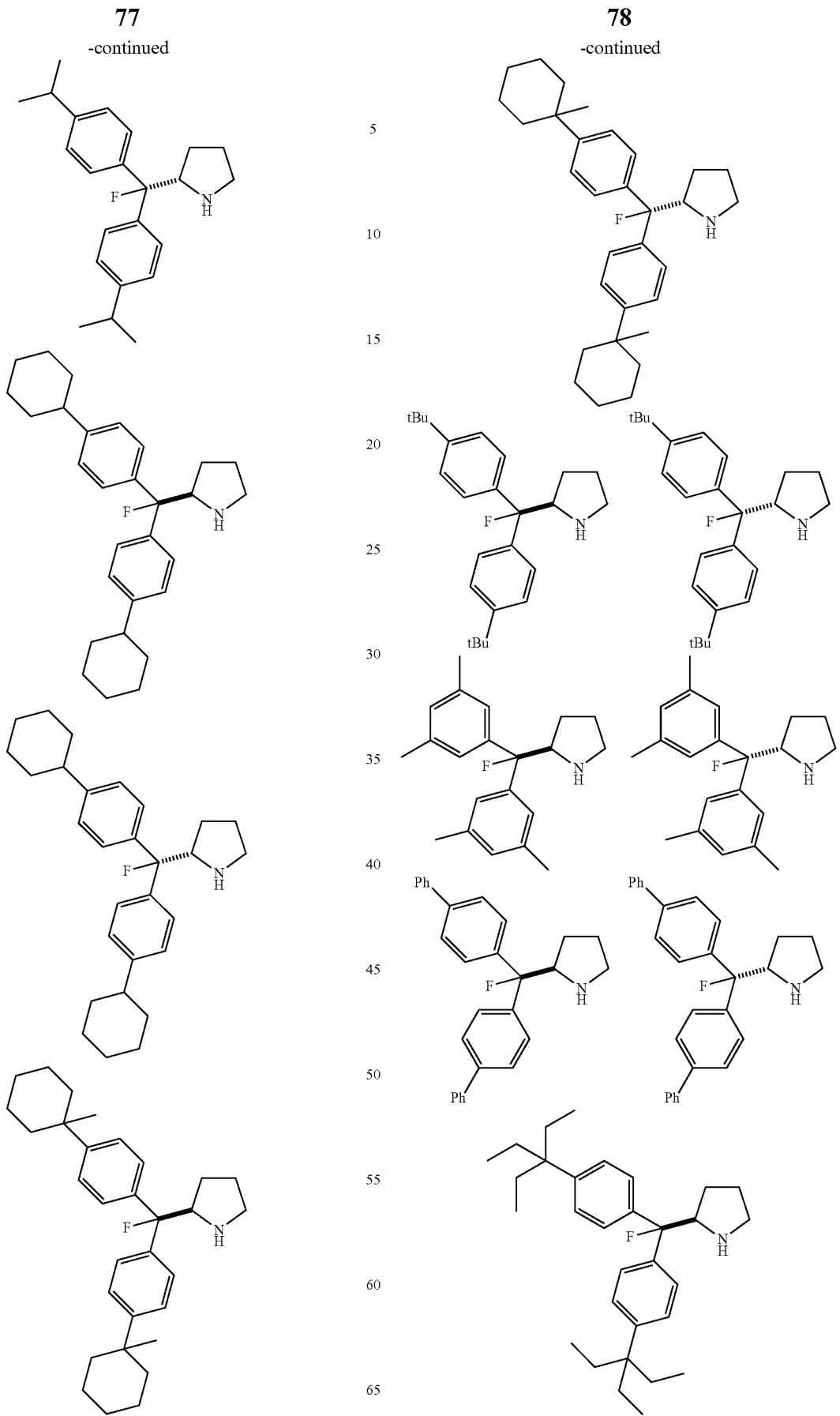

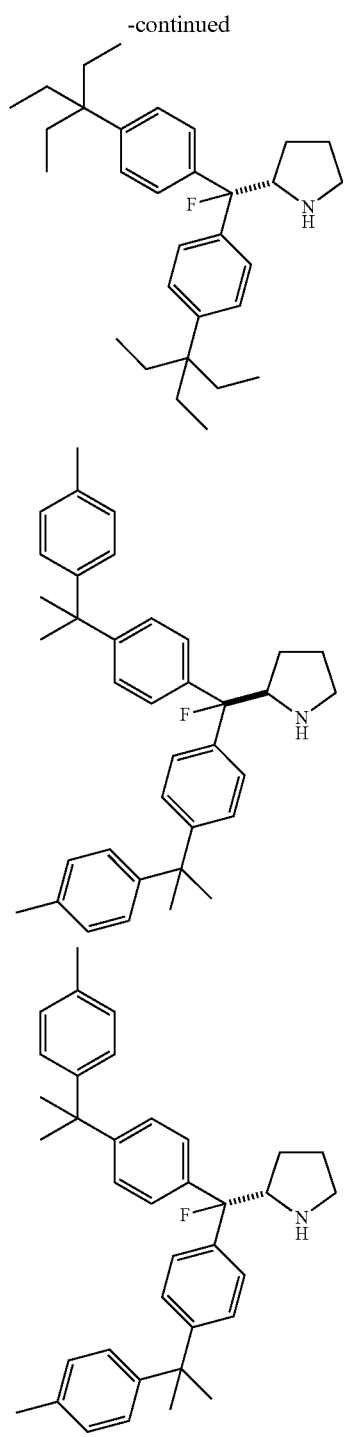
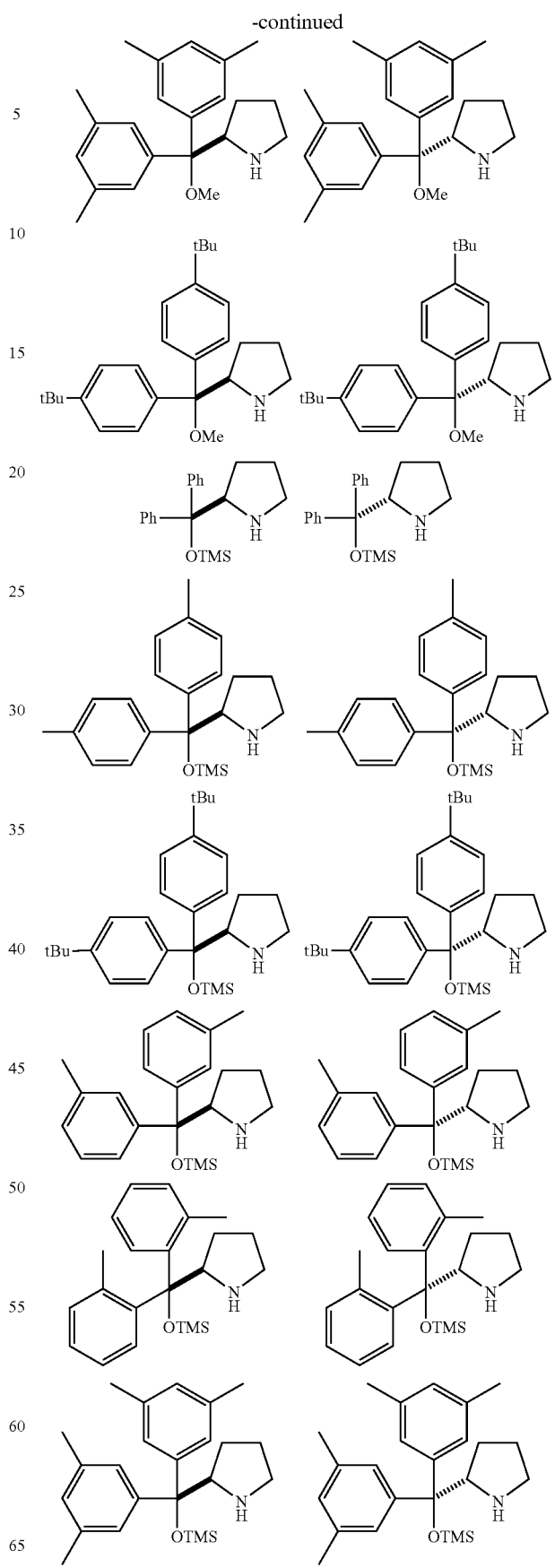
[Chem. 34]
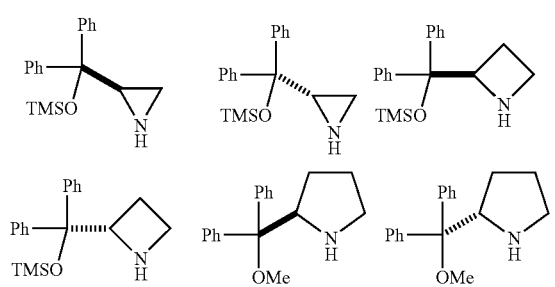

-continued
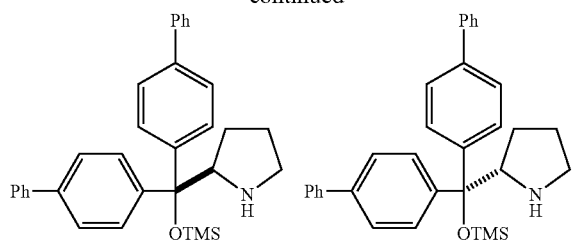
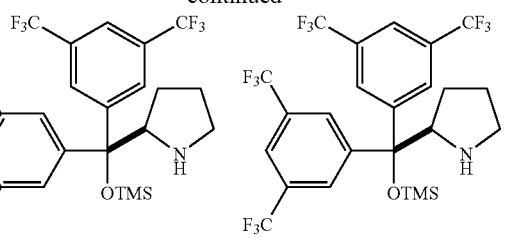
[Chem. 35]
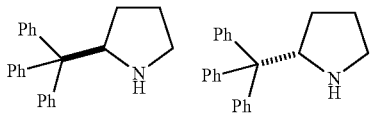
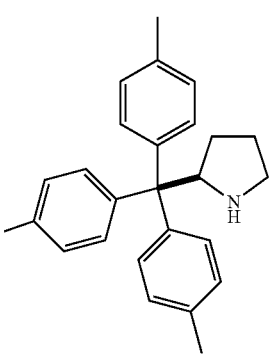
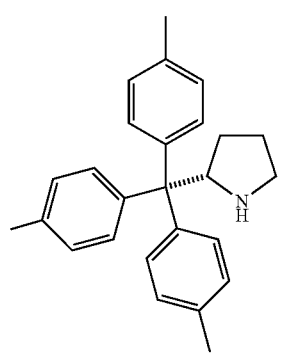
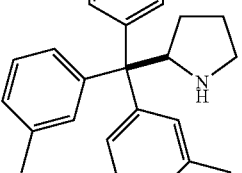
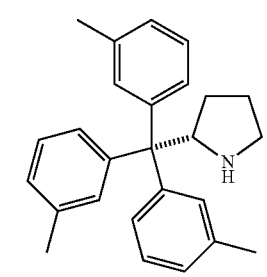
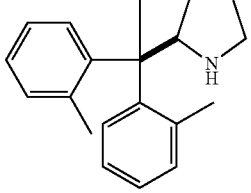
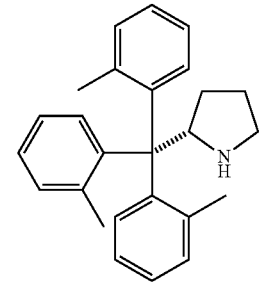
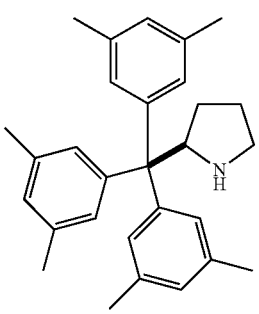
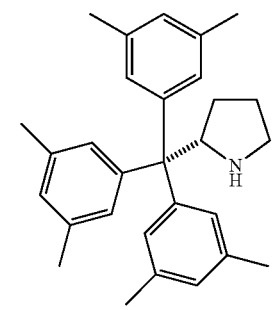

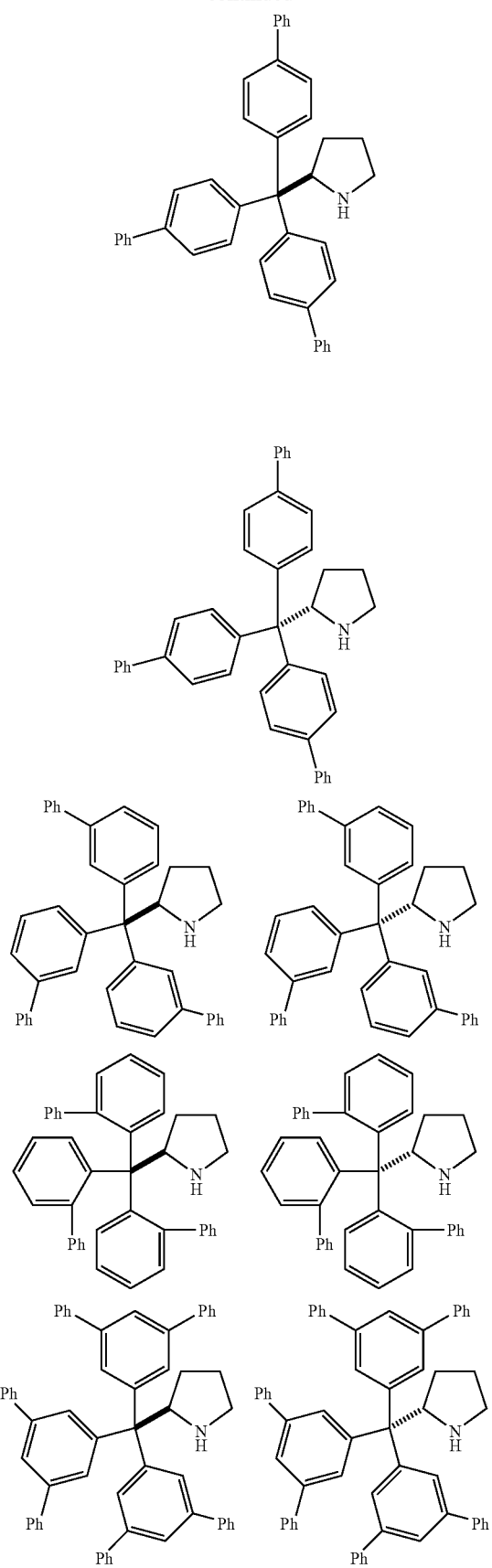
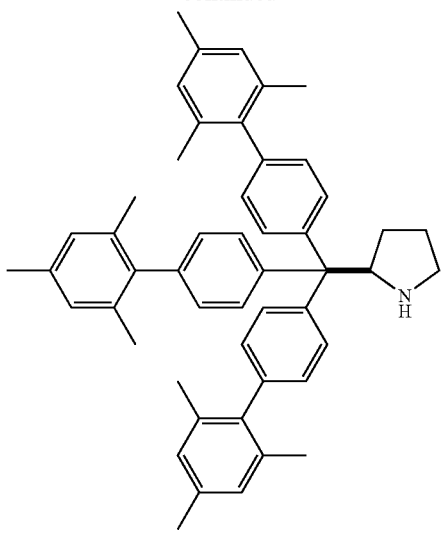
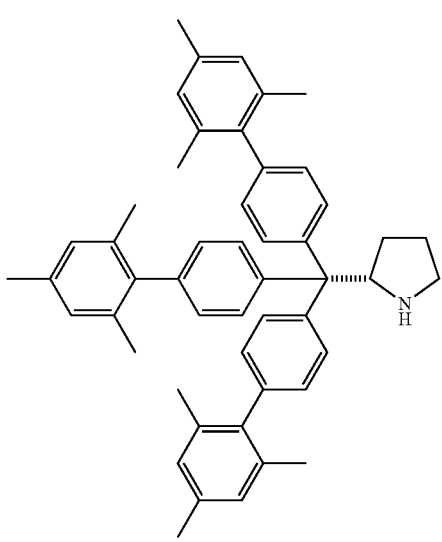
[Chem. 36]
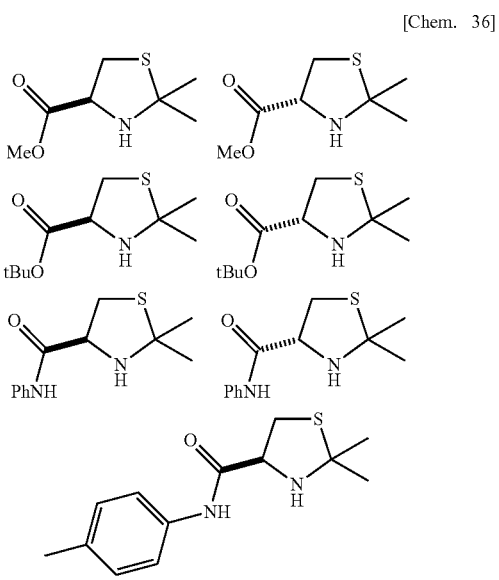

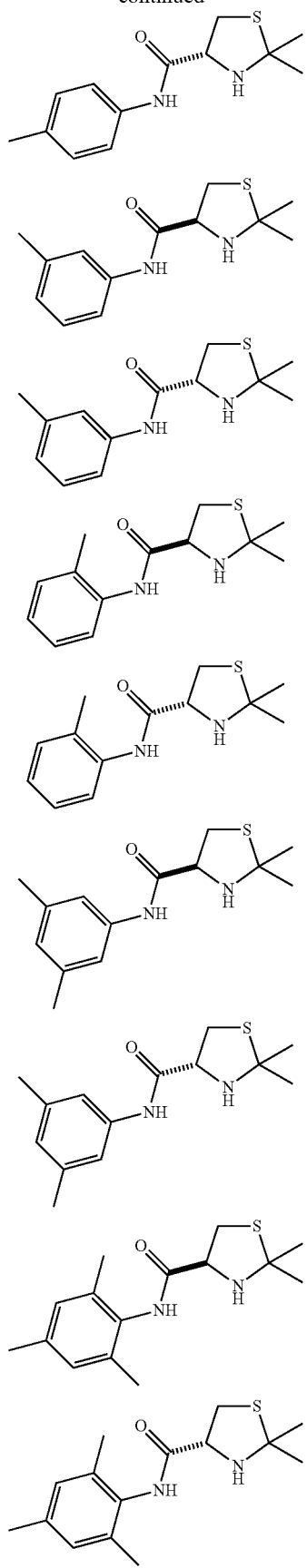
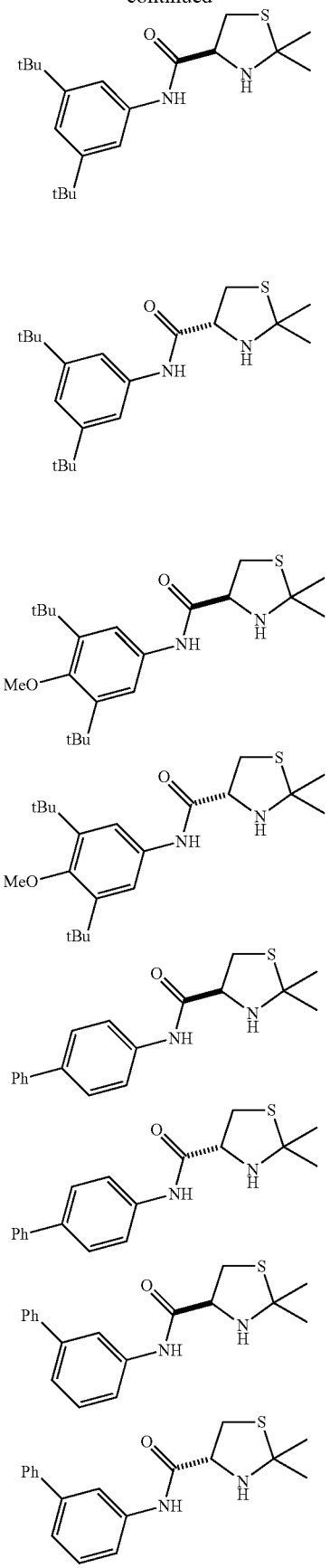

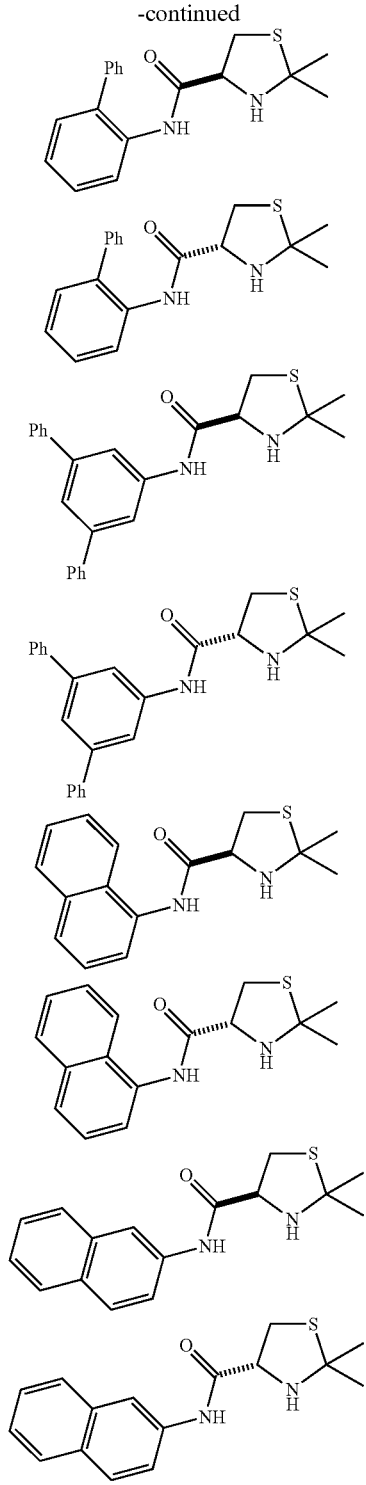

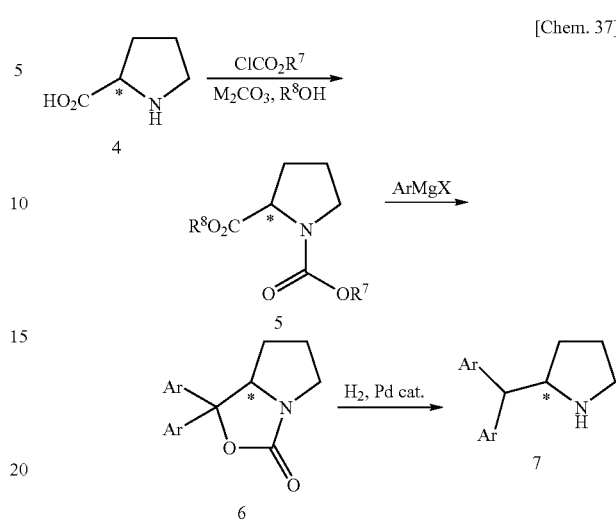

In Scheme 1, the compound 5 can be synthesized in accordance with the method described in Tetrahedron, 1993, 49, 5127-5132.

Synthesis of the compound 5 can be carried out by adding a chlorocarbonic acid ester compound represented by the general formula $ClCO_2R^7$, dropwise at a temperature within the range of from 0 to 30° C., to a solution prepared by dissolving (R)- or (S)-proline (compound 4) and an alkali metal compound represented by the general formula $M_2CO_3$ in an alcohol compound represented by the general formula $R^8OH$. Using amount of the solvent is, for example, from 10 to 30 times volume (ml) [ml/g], preferably from 15 to 25 times volume (ml) [ml/g], based on the weight (g) of (R)- or (S)-proline as the substrate.

The compound 5 obtained as described in the above can be isolated and purified by generally used operations such as extraction, recrystallization, various types of chromatography and the like.

As the group represented by $R^7$ in the chlorocarbonic acid ester compound represented by the general formula $ClCO_2R^7$, there may be mentioned alkyl groups having from 1 to 8 carbon atoms such as methyl group, ethyl group, propyl group, isopropyl group, butyl group, pentyl group, hexyl group, heptyl group and octyl group; cyclic alkyl groups having from 1 to 8 carbon atoms such as cyclopropyl group, cyclobutyl group, cyclopentyl group, cycloheptyl group and cyclooctyl group; aralkyl groups having from 7 to 10 carbon atoms such as benzyl group and p-methylbenzyl group, and the like.

As the metal represented by M in the alkali metal compound represented by the general formula $M_2CO_3$, lithium, sodium, potassium, cesium and the like can be mentioned.

As the group represented by $R^8$ in the alcohol compound represented by the general formula $R^8OH$, there may be mentioned alkyl groups having from 1 to 8 carbon atoms such as methyl group, ethyl group, propyl group, isopropyl group, butyl group, pentyl group, hexyl group, heptyl group and octyl group; cyclic alkyl groups having from 1 to 8 carbon atoms such as cyclopropyl group, cyclobutyl group, cyclopentyl group, cycloheptyl group and cyclooctyl group; aralkyl groups having from 7 to 10 carbon atoms such as benzyl group and p-methylbenzyl group, and the like.

The optically active cyclic nitrogen-containing compounds to be used in the invention are commercially available or can also be synthesized. Among the optically active cyclic nitrogen-containing compounds, production method of optically active diarylmethylpyrrolidine compounds is described.

The optically active diarylmethylpyrrolidine compounds can be synthesized, for example, in accordance with the method described in Tetrahedron, 1993, 49, 5127-5132, and Tetrahedron: Asymmetry, 1997, 8, 149-153. Said method can be shown by the following Scheme 1.

The compound 6 ca be synthesized in accordance with the method described in Tetrahedron: Asymmetry, 1997, 8, 149-153.

Synthesis of the compound 6 is carried out by adding ether solution, such as a THF, of a Grignard compound represented by the general formula ArMgX dropwise to ether solution, such as a THF, of the compound 5, under an atmosphere of an inert gas at a temperature of from −5 to 20° C., and rising the reaction temperature finally to about 70° C. and keeping it for a period of from 3 to 6 hours. Using amount of the solvent is, for example, from 1 to 10 times volume (ml) [ml/g], preferably from 2 to 3 times volume (ml) [ml/g], based on the weight (g) of the compound 5 as the substrate.

The compound 6 obtained as described in the above can be isolated and purified by generally used operations such as extraction, recrystallization, various types of chromatography and the like.

As the aryl group represented by Ar in the Grignard compound represented by the general formula ArMgX, an aryl group having, for example, from 6 to 20 carbon atoms, which may have a substituent group, can be mentioned.

As illustrative examples of the aryl group, the aryl groups enumerated in the description of $R^1$ and $R^2$ of the optically active cyclic nitrogen-containing compounds can be mentioned.

As illustrative examples of the substituent group substituting the aryl group, the groups described in the description on the substituent group of alkyl group enumerated in the description of $R^1$ and $R^2$ of the optically active cyclic nitrogen-containing compounds can be mentioned.

As the aryl group, for example, phenyl group, tolyl group, isopropylphenyl group, xylyl group, t-butylphenyl group, cyclohexyl group, 1-methylcyclohexyl group, adamantylphenyl group, trifluoromethylphenyl group, naphthyl group, anthryl group, phenanthryl group, biphenyl group, 4-(2'-p-tolylpropyl)phenyl group and the like can be mentioned.

As the halogen atom represented by X in the Grignard compound represented by the general formula ArMgX, for example, chlorine, bromine and iodine can be mentioned.

The optically active diarylmethylpyrrolidine compounds represented by the compound 7 can be synthesized in accordance with the method described in Tetrahedron: Asymmetry, 1997, 8, 149-153.

Synthesis of the compound 7 is carried out by debenzylating the compound 6 at a temperature of from 20 to 80° C. for a period of from 1 day to 10 days in a hydrogen atmosphere of approximately from 0.1 MPa to 1 MPa, in the alcohol solvent represented by $R^8OH$, THF or a mixed solvent thereof in the presence of palladium catalyst in an amount of from 0.1 to 40% by weight based on the compound 6. Using amount of the solvent is, for example, from 5 to 50 times volume (ml) [ml/g], preferably from 20 to 40 times volume (ml) [ml/g], based on the weight (g) of the substrate compound 6.

The optically active diarylmethylpyrrolidine compound of compound 7 obtained as described in the above can be isolated and purified by generally used operations such as extraction, recrystallization, various types of chromatography and the like.

The palladium catalyst represented by the general formula Pd cat. is selected from debenzylation catalysts such as Pd/C.

In this connection, the * in Scheme 1 represents asymmetric carbon atom.

In addition, according to the invention, an acid is included as another catalyst component.

As the acid, an organic acid or an inorganic acid can be used, but an organic acid is desirable.

As illustrative examples of the organic acid, there will be mentioned acetic acid, chloroacetic acid, difluoroacetic acid, trifluoroacetic acid, trichloroacetic acid, tribromoacetic acid, benzoic acid, 2,4-dinitrobenzoic acid, p-toluenesulfonic acid, methanesulfonic acid, L-mandelic acid, D-mandelic acid, trifluoromethanesulfonic acid and the like.

As illustrative examples of the inorganic acid, there will be mentioned hydrofluoric acid, hydrochloric acid, hydrobromic acid, hydroiodic acid, sulfuric acid, perchloric acid, phosphoric acid, nitric acid and the like.

<Production Method of Optically Active Carbonyl Compound>

According to the invention, an optically active carbonyl compound such as an optically active aldehyde or an optically active ketone can be obtained by subjecting an α,β-unsaturated carbonyl compound to asymmetric hydrogenation reaction in the presence of the aforementioned catalyst.

Using amounts of the metal powder and metal-supported substance to be used as catalyst components of the invention vary depending on various reaction conditions, but total weight of the metal powder and total weight of the metal-supported substance are, for example, from 0.01 to 10% by weight, preferably from 0.1 to 5% by weight, based on the weight of the α,β-unsaturated carbonyl compound as the substrate.

Using amount of the optically active cyclic nitrogen-containing compound to be used as a catalyst component of the invention vary depending on various reaction conditions, but is, for example, from 0.01 to 20% by weight, preferably from 0.1 to 5% by weight, based on the α,β-unsaturated carbonyl compound as the substrate.

Using amount of the acid to be used as catalyst components of the invention vary depending on various reaction conditions, but is, for example, 0.01 to 10 times by mol, preferably 0.2 to 4 times by mol based on the optically active cyclic nitrogen-containing compound.

When an optically active carbonyl compound is produced by carrying out asymmetric hydrogenation of the α,β-unsaturated carbonyl compound using the catalyst of the invention, it can be carried out in the presence or absence of a solvent, but it is desirable to carry it out in the presence of a solvent.

As the illustrative solvent to be used, aliphatic hydrocarbon-based organic solvents such as hexane, heptane and octane; alicyclic hydrocarbon-based organic solvents such as cyclohexane and methylcyclohexane; aromatic hydrocarbon-based organic solvents such as benzene, toluene and xylene; ether-based organic solvents such as diethyl ether, diisopropyl ether, dimethoxyethane, tetrahydrofuran, dioxane and dioxolan; water; alcohol-based organic solvents such as methanol, ethanol, propanol, isopropanol and tertiary butanol; halogenated hydrocarbon-based organic solvents such as dichloromethane, dichloroethane, chlorobenzene and bromotoluene; dimethylformamide, acetonitrile and the like are desirable, and a mixed solvent of these solvents can also be used in response to the necessity. Among these solvents, heptane, toluene, tetrahydrofuran, t-butanol and hydrous t-butanol are particularly desirable.

Using amount of the solvent can be optionally selected based on the reaction conditions and the like, but is, for example, from 0 to 20 times volume (ml) [(ml/g)], preferably from 0 to 5 times volume (ml) [(ml/g)], based on the weight (g) of the α,β-unsaturated carbonyl compound as the substrate.

The method of the invention is carried out using hydrogen gas as the hydrogen source, and its hydrogen pressure is from 0.01 MPa to 10 MPa, preferably from 0.1 MPa to 1 MPa. The reaction temperature is from −78 to 100° C., preferably from 10 to 70° C. The reaction time varies depending on the reaction conditions, but is generally from 1 to 30 hours.

The optically active carbonyl compound obtained as described in the above can be isolated and purified by generally used operations such as extraction, recrystallization, various types of chromatography and the like. In addition, regarding configuration of the thus obtained optically active carbonyl compound, its d-form or l-form (R-form or S-form) can be produced by optionally selecting configuration of the optically active cyclic nitrogen-containing compound.

EXAMPLES

The following describes the invention further illustratively based on examples and comparative examples, though the invention is not restricted thereby.

Measurement of the products was carried out by a gas chromatographic method (GLC). Its conditions are as described in the following.

The used instrument for analysis: G2010 gas chromatography manufactured by Shimadzu Corp.

Column: DB-WAX (0.25 mm×30 m) manufactured by Agilent for conversion ratio measurement β-DEX-225 (0.25 mm×30 m) manufactured by SUPELCO for optical purity Detector: FID Among the optically active cyclic nitrogen-containing compounds, the compounds used in Examples 48 to 56 and 58 to 61 were synthesized by the following methods. In the other Examples, compounds manufactured by Aldlich Corporation were used.

Synthesis Example 1

Synthesis of (R)-proline-N-ethyl carbamate methyl ester

[Chem. 38]

This was carried out in accordance with the synthesis method of Tetrahedron, Vol. 49, No. 23, 5127-5132.

A 35.54 g (0.3 mol) portion of (R)-proline, 600 ml of anhydrous methanol and 41.46 g of potassium carbonate were put into a 2 liter capacity four neck flask, followed by stirring. Under ice-cooling, 71.62 g (0.66 mmol) of ethyl chlorocarbonate was added dropwise thereto at 25° C. or less, followed by stirring at 0° C. for 12 hours. Thereafter, methanol was evaporated, the residue was mixed with 300 ml of water and extracted with 450 ml of chloroform, and the water layer was further extracted twice with 450 ml of chloroform. The thus obtained organic layer was washed with saturated brine, dried with anhydrous magnesium sulfate and filtered, and then the solvent was evaporated to obtain 52.85 g of the product of interest with a yield of 87.5%.

Synthesis Example 2

Synthesis of (S)-proline-N-ethyl carbamate methyl ester

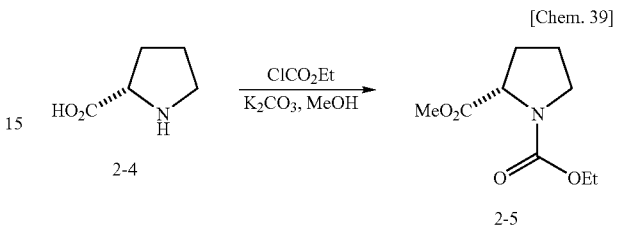

[Chem. 39]

This was carried out in accordance with the synthesis method of Tetrahedron, Vol. 49, No. 23, 5127-5132.

A 23.03 g (0.2 mol) portion of (S)-proline, 400 ml of anhydrous methanol and 27.64 g of potassium carbonate were put into a 1 liter capacity four neck flask, followed by stirring. Under ice-cooling, 47.75 g (0.44 mmol) of ethyl chlorocarbonate was added dropwise thereto at 25° C. or less, followed by stirring at 0° C. for 12 hours. Thereafter, methanol was evaporated, the residue was mixed with 200 ml of water and extracted with 300 ml of chloroform, and the water layer was further extracted twice with 300 ml of chloroform. The thus obtained organic layer was washed with saturated brine, dried with anhydrous magnesium sulfate and filtered, and then the solvent was evaporated to obtain 35.85 g of the product of interest with a yield of 89.1%.

Synthesis Example 3

Synthesis of (R)-2-(bis-(4'-t-butylphenyl)methyl) pyrrolidine (Synthesis of the Optically Active Cyclic Nitrogen-Containing Compound of Examples 48 to 53)

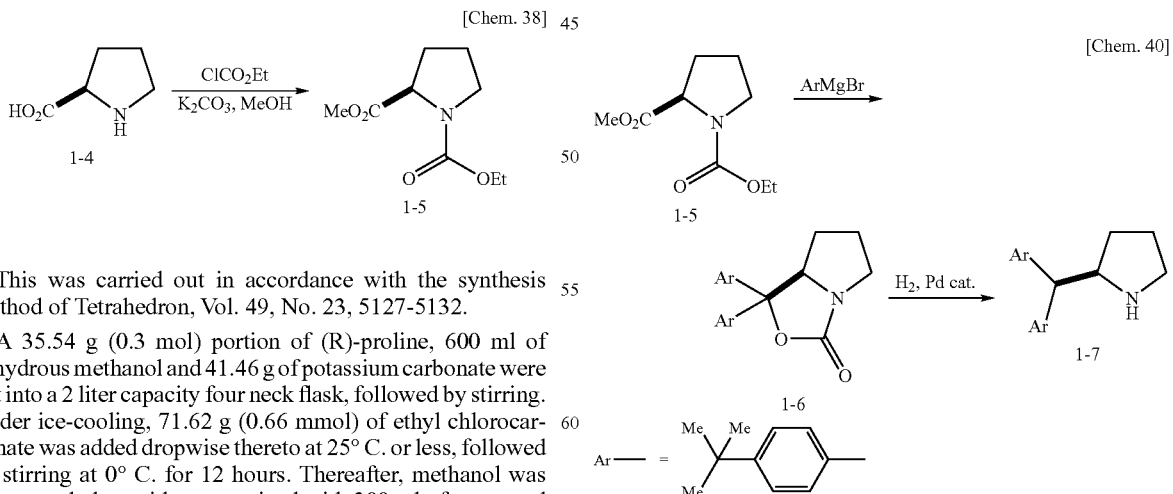

[Chem. 40]

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 12.55 g (469 mmol) of magnesium and 50 ml of anhydrous THF were put into a nitrogen-replaced 1 liter capacity reaction flask, followed by stirring. At room temperature, a 500 ml THF solution of 100 g (469 mmol) of 4-t-butylphenylbromobenzene was added dropwise thereto, followed by stirring at room temperature for 1 hour (synthesis of a Grignard compound).

Next, the above-mentioned solution was cooled to 5° C. or less, and a 200 ml THF solution of 47.2 g (235 mmol) of the (R)-proline-N-ethyl carbamate methyl ester obtained in Synthesis Example 1 was added dropwise thereto at 10° C. or less and allowed to undergo the reaction. Thereafter, this was heated under reflux for 3 hours and then cooled, and the reaction solution was added to 500 ml of saturated ammonium chloride aqueous solution, mixed with 500 ml of toluene for extraction, followed by stirring for 1 hour. This was transferred to a separating funnel, the organic layer was separated and the water layer was extracted twice with 500 ml of toluene, and the organic layers were combined and washed twice with saturated brine. After drying the organic layer with anhydrous sodium sulfate, the solvent was evaporated, and the thus obtained crystals were dissolved with heating in 1,200 ml of toluene. After cooling, the thus obtained crystals were collected by filtration and then dried under a reduced pressure to obtain 65.8 g of (5R)-[3,3,0]-1-aza-2-oxo-3-oxa-4,4-bis-(4'-t-butylphenyl)-bicyclooctane.

A 460 ml portion of methanol, 460 ml of THF and 2.63 g of 10% Pd—C were added to the thus obtained (5R)-[3,3,0]-1-aza-2-oxo-3-oxa-4,4-bis-(4'-t-butylphenyl)-bicyclooctane, followed by stirring to carry out hydrogen replacement. After carrying out the reaction as such at room temperature for 10 days, Pd—C was removed by filtration and the filtrate was concentrated and purified by a silica gel column chromatography, thereby obtaining 43.6 g of the specified substance as colorless crystals with a yield of 74.3%.

$^1$H-NMR (CD$_3$OD): δ=1.10 to 1.50, m, 19H δ=1.60 to 1.85, m, 3H δ=2.65 to 2.80, m, 1H δ=2.80 to 2.95, m, 1H δ=3.65, d, 1H δ=3.70 to 3.85, m, 1H δ=7.10 to 7.35, m, 8H

Synthesis Example 4

Synthesis of (S)-2-(bis-(4'-t-butylphenyl)methyl) pyrrolidine (Synthesis of the Optically Active Cyclic Nitrogen-Containing Compound of Example 54)

[Chem. 41]

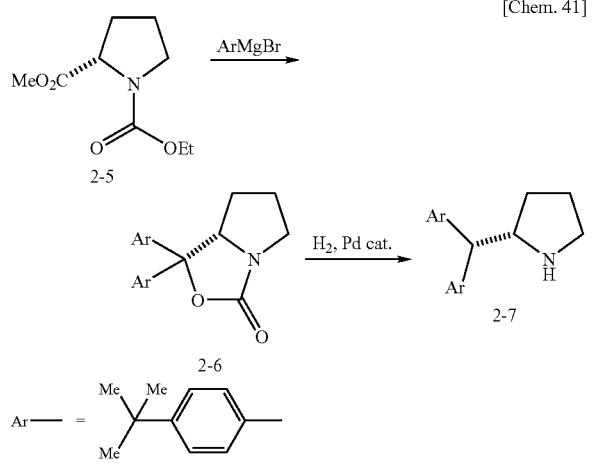

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 2.55 g (105 mmol) of magnesium and 50 ml of anhydrous THF were put into a nitrogen-replaced 300 ml capacity reaction flask, followed by stirring. At room temperature, a 30 ml THF solution of 21.31 g (100 mmol) of 4-t-butylphenylbromobenzene was added dropwise thereto, followed by stirring at room temperature for 1 hour (synthesis of a Grignard compound).

Next, the above-mentioned solution was cooled to 5° C. or less, and 10.05 g (50 mmol) of the (S)-proline-N-ethyl carbamate methyl ester obtained in Synthesis Example 2 was added dropwise thereto at 10° C. or less and allowed to undergo the reaction. Thereafter, this was heated under reflux for 3 hours and then cooled, and the reaction solution was added to 100 ml of saturated ammonium chloride aqueous solution, mixed with 100 ml of toluene for extraction, followed by stirring for 1 hour. This was transferred to a separating funnel, the organic layer was separated and the water layer was extracted twice with 100 ml of toluene, and the organic layers were combined and washed twice with saturated brine. After drying the organic layer with anhydrous sodium sulfate, the solvent was evaporated, and the thus obtained crystals were dissolved with heating in 140 ml of ethyl acetate. After cooling, the thus obtained crystals were collected by filtration and then dried under a reduced pressure to obtain 9.13 g of (5S)-[3,3,0]-1-aza-2-oxo-3-oxa-4,4-bis-(4'-t-butylphenyl)-bicyclooctane.

A 100 ml portion of methanol, 100 ml of THF and 365 mg of 10% Pd—C were added to the thus obtained (5S)-[3,3,0]-1-aza-2-oxo-3-oxa-4,4-bis-(4'-t-butylphenyl)-bicyclooctane, followed by stirring to carry out hydrogen replacement. After carrying out the reaction as such at room temperature for 4 days, Pd—C was removed by filtration and the filtrate was concentrated and purified by a silica gel column chromatography, thereby obtaining 3.48 g of the specified substance as colorless crystals with a yield of 19.93%.

$^1$H-NMR(CD$_3$OD): δ=1.10 to 1.50, m, 19H δ=1.60 to 1.85, m, 3H δ=2.65 to 2.80, m, 1H δ=2.80 to 2.95, m, 1H δ=3.65, d, 1H δ=3.70 to 3.85, m, 1H δ=7.10 to 7.35, m, 8H

Synthesis Example 5

Synthesis of (S)-2-(bis-(4'-i-propylphenyl)methyl) pyrrolidine (Synthesis of the Optically Active Cyclic Nitrogen-Containing Compound of Example 55)

[Chem. 42]

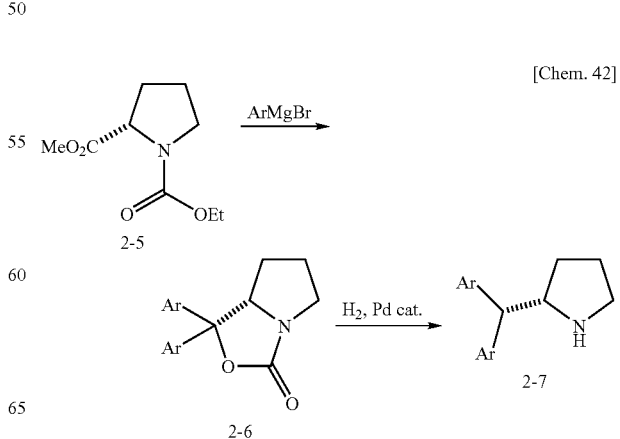

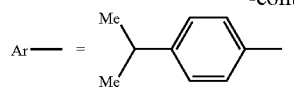

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 2.55 g (105 mmol) of magnesium and 50 ml of anhydrous THF were put into a nitrogen-replaced 300 ml capacity reaction flask, followed by stirring. At room temperature, a 30 ml THF solution of 19.91 g (100 mmol) of 4-t-propylphenylbromobenzene was added dropwise thereto, followed by stirring at room temperature for 1 hour (synthesis of a Grignard compound).

Next, the above-mentioned solution was cooled to 5° C. or less, and 10.05 g (50 mmol) of the (S)-proline-N-ethyl carbamate methyl ester obtained in Synthesis Example 2 was added dropwise thereto at 10° C. or less and allowed to undergo the reaction. Thereafter, this was heated under reflux for 3 hours and then cooled, and the reaction solution was added to 100 ml of saturated ammonium chloride aqueous solution, mixed with 100 ml of toluene for extraction, followed by stirring for 1 hour. This was transferred to a separating funnel, and the organic layer was separated and washed twice with saturated brine. After drying the organic layer with anhydrous sodium sulfate, the solvent was evaporated to obtain 16.22 g of (5S)-[3,3,0]-1-aza-2-oxo-3-oxa-4,4-bis-(4'-i-propylphenyl)-bicyclooctane.

A 100 ml portion of methanol, 50 ml of THF and 650 mg of 10% Pd—C were added to the thus obtained (5S)-[3,3,0]-1-aza-2-oxo-3-oxa-4,4-bis-(4'-i-propylphenyl)-bicyclooctane, followed by stirring to carry out hydrogen replacement. After carrying out the reaction as such at room temperature for 4 days, Pd—C was removed by filtration and the filtrate was concentrated and purified by a silica gel column chromatography, thereby obtaining 2.71 g of the specified substance as colorless crystals with a yield of 16.86%.

$^1$H-NMR (CD$_3$OD): δ=1.05 to 1.20, m, 12H δ=1.20 to 1.35, m, 1H δ=1.60 to 1.80, m, 3H δ=2.65 to 2.95, m, 4H δ=3.60, d, 1H δ=3.70 to 3.85, m, 1H δ=7.00 to 7.30, m, 8H

Synthesis Example 6

Synthesis of (R)-2-(bis-(4'-(1"-methylcyclohexyl)phenyl)methyl)pyrrolidine (Synthesis of the Optically Active Cyclic Nitrogen-Containing Compound of Example 56)

[Chem. 43]

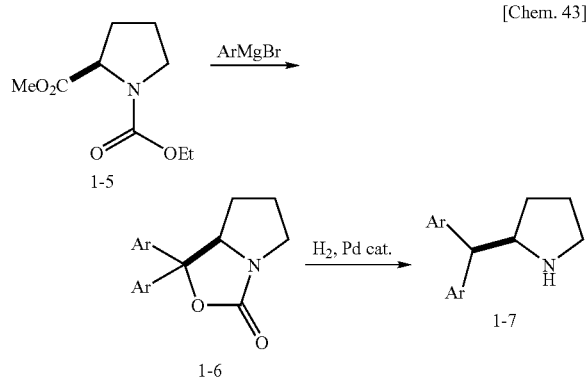

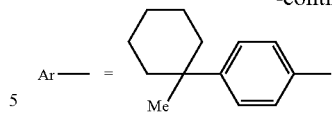

(1) Synthesis of 1-methylcyclohexylbenzene

A mixed solution of 75.0 ml (632 mmol) of 1-methyl-1-cyclohexene and 56.4 ml (632 mmol) of benzene was added at 0° C. dropwise to 225.6 ml (2.53 mol) benzene solution of 231 g (2.36 mol) of sulfuric acid spending 1.5 hours, followed by stirring at 0° C. for 1.5 hours. The reaction solution was quenched by adding 300 ml of water, and the water layer was separated. The thus obtained organic layer was washed with 100 ml of saturated sodium hydrogen carbonate aqueous solution, 100 ml of water and 100 ml of saturated brine and dried with anhydrous sodium sulfate. After filtering the desiccant, the filtrate was concentrated to obtain crude 1-methylcyclohexylbenzene. By purifying the thus obtained crude 1-methylcyclohexylbenzene by distillation under a reduced pressure (from 110 to 113° C./10 mmHg), 40.2 g of the specified substance was obtained with a yield of 36.5%.

$^1$H-NMR (CDCl$_3$): δ=1.20, s, 3H δ=1.30 to 1.70, m, 8H δ=1.90 to 2.10, m, 2H δ=7.10 to 7.40, m, 5H (2) Synthesis of 4-(1'-methylcyclohexyl)bromobenzene To 20.0 g (115 mmol) of the 1-methylcyclohexylbenzene obtained in the above-mentioned (1) were added 279 mg (5.00 mmol) of iron and 198 mg (0.78 mmol) of iodine, and 17.8 g (111 mmol) of bromine was slowly added dropwise at 0° C. spending 1.5 hours, followed by stirring at the same temperature for 1.5 hours and then at room temperature for 20 hours. The reaction solution was cooled and then quenched with 30 ml of saturated sodium sulfite aqueous solution and extracted three times with 50 ml of hexane. The combined organic layers were washed with 30 ml of sodium sulfite aqueous solution and 30 ml of water and dried with anhydrous sodium sulfate. After filtration of the desiccant, the solvent was recovered under a reduced pressure to obtain 27.9 g of crude bromide. By purifying the thus obtained crude bromide by distillation under a reduced pressure (from 117 to 120° C./2 mmHg), the specified substance was obtained with a yield of 80.3%.

$^1$H-NMR(CDCl$_3$): δ=1.15, s, 3H δ=1.30 to 1.70, m, 8H δ=1.90 to 2.10, m, 2H 2H δ=7.15 to 7.50, m, 4H (3) Synthesis of (R)-2-(bis-(4'-(1"-methylcyclohexyl)phenyl)methyl)pyrrolidine This was synthesized in accordance with the synthesis method of (S)-2-(diphenylmethyl)pyrrolidine described in Tetrahedron: Asymmetry, Vol. 8, No. 1, 149-153.

Under a stream of nitrogen, 535 mg (22.0 mmol) of magnesium and 4 ml of anhydrous THF were put into a nitrogen-replaced 100 ml capacity reaction flask, followed by stirring. A 25 ml portion of THF solution of 5.06 g (20 mmol) of the 4-(1'-methylcyclohexyl)bromobenzene obtained in the above-mentioned (2) was added dropwise thereto at room temperature, followed by stirring at room temperature for 1 hour (synthesis of a Grignard compound).

Next, the above-mentioned solution was cooled to 5° C. or less, and 16 ml THF solution of 2.01 g (10 mmol) of the (R)-proline-N-ethyl carbamate methyl ester obtained in Synthesis Example 1 was added dropwise thereto at 10° C. or less and allowed to undergo the reaction. Thereafter, this was heated under reflux for 3 hours and then cooled, and the reaction solution was put into 25 ml of saturated ammonium chloride aqueous solution, mixed with 50 ml of chloroform for extraction, followed by stirring for 1 hour. This was transferred into a separating funnel, and the organic layer was separated and washed twice with saturated brine. After drying the organic layer with anhydrous sodium sulfate, the solvent was evaporated to obtain 4.76 g of a concentrate. By recrystallizing it from ethyl acetate, 2.37 g of (5R)-[3,3,0]-1-aza-2-oxo-3-oxa-4,4-bis-(4'-(1"-methylcyclohexyl)phenyl)-bicyclooctane was obtained.

A 35 ml portion of methanol, 35 ml of THF and 1.10 g of 10% Pd—C were added to the thus obtained (5R)-[3,3,0]-1-aza-2-oxo-3-oxa-4,4-bis-(4'-(1"-methylcyclohexyl)phenye-bicyclooctane, followed by stirring to carry out hydrogen replacement. After carrying out 7.5 hours of the reaction at 50° C., Pd—C was removed by filtration and the filtrate was concentrated and purified by a silica gel column chromatography to obtain 1.50 g of colorless crystals of the specified substance with a yield of 35.0%.

$^1$H-NMR (CDCl$_3$): δ=1.10 to 1.20, s, 6H δ=1.25 to 2.20, m, 24H δ=2.70 to 3.00, m, 2H δ=3.70 to 3.95, m, 2H δ=7.10 to 7.40, m, 8H

Synthesis Example 7

Synthesis of (R)-2-(bis-(p-1'-adamantylphenyl)methyl)pyrrolidine (Synthesis of the Optically Active Cyclic Nitrogen-Containing Compound of Example 58)

Next, the above-mentioned solution was cooled to 5° C. or less, and 2.04 g (10.1 mmol) of the (R)-proline-N-ethyl carbamate methyl ester obtained in Synthesis Example 1 was added dropwise thereto at 10° C. or less and allowed to undergo the reaction. Thereafter, this was heated under reflux for 3 hours and then cooled, and the reaction solution was put into 100 ml of saturated ammonium chloride aqueous solution, mixed with 300 ml of THF for extraction, followed by stirring for 1 hour. This was transferred into a separating funnel, and the organic layer was separated and washed once with saturated brine. After drying the organic layer with anhydrous sodium sulfate, the solvent was evaporated to obtain 2.37 g of (5R)-[3,3,0]-1-aza-2-oxo-3-oxa-4,4-bis-(p-1'-adamantylphenyl)-bicyclooctane.

A 36 ml portion of methanol, 36 ml of THF and 1.18 g of 10% Pd—C were added to the thus obtained (5R)-[3,3,0]-1-aza-2-oxo-3-oxa-4,4-bis-(p-1'-adamantylphenyl)-bicyclooctane, followed by stirring to carry out hydrogen replacement. After carrying out 70 hours of the reaction at from 50 to 60° C., Pd—C was removed by filtration and the filtrate was concentrated and purified by an alumina column chromatography to obtain 1.45 g of colorless crystals of the specified substance with a yield of 31.6%.

$^1$H-NMR (CDCl$_3$): δ=1.40 to 2.20, m, 30H δ=2.60 to 2.80, br, 1H δ=3.05 to 3.90, m, 2H δ=4.10 to 4.90, m, 2H δ=7.00 to 7.50, m, 8H

Synthesis Example 8

Synthesis of (R)-2-(bis-(4'-(2"-p-tolylpropyl)phenyl)methyl)pyrrolidine (Synthesis of the Optically Active Cyclic Nitrogen-Containing Compound of Example 59)

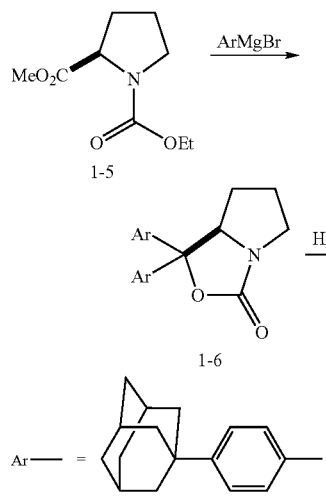

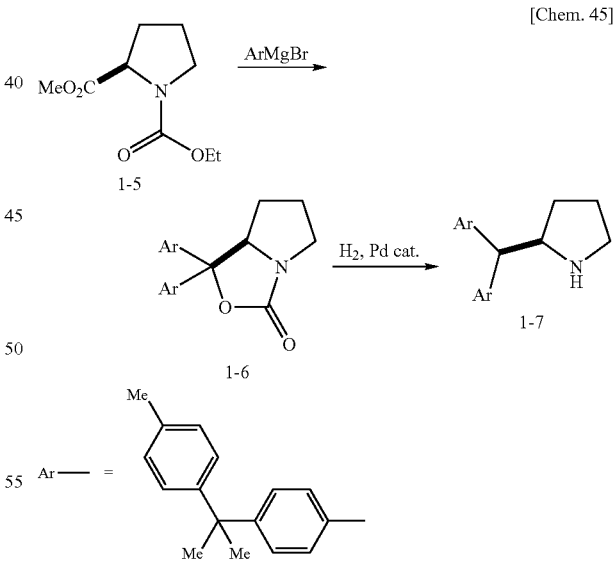

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 0.591 g (24.3 mmol) of magnesium and 10 ml of anhydrous THF were put into a nitrogen-replaced 200 ml capacity reaction flask, followed by stirring. A 30 ml portion of THF solution of 5.00 g (20.3 mmol) of p-1-adamantylphenylchlorobenzene was added thereto at room temperature, followed by stirring at room temperature for 1 hour (synthesis of a Grignard compound).

(1) Synthesis of 4-(2'-p-tolylpropyl)chlorobenzene

A mixed solution of 21.5 ml (150 mmol) of p-chloromethylstyrene and 20 ml (280 mmol) of toluene was added dropwise at 0° C. and spending 1 hour to 59.9 ml (470 mmol) toluene solution of 44.1 g (450 mmol) of sulfuric acid, followed by stirring at 0° C. for 2.0 hours. The reaction solution was quenched by adding 100 ml of water, and the water layer was separated. The thus obtained organic layer was washed with 50 ml of saturated sodium hydrogen carbonate aqueous solution and 50 ml of water and dried with anhydrous sodium sulfate. After filtering the desiccant, the filtrate was concentrated to obtain a crude chloride. By purifying the thus obtained crude chloride by distillation under a reduced pressure (from 120 to 130° C./1 mmHg), 31.8 g of the specified substance was obtained with a yield of 86.7%.

$^1$H-NMR (CDCl$_3$): δ=1.80, s, 6H δ=2.45, s, 3H δ=7.20 to 7.45, m, 8H (2) Synthesis of (R)-2-(bis-(4'-(2''-p-tolylpropyl)phenyl)methyl)pyrrolidine This was synthesized in accordance with the synthesis method of (S)-2-(diphenylmethyl)pyrrolidine described in Tetrahedron: Asymmetry, Vol. 8, No. 1, 149-153.

Under a stream of nitrogen, 535 mg (22.0 mmol) of magnesium and 4 ml of anhydrous THF were put into a nitrogen-replaced 100 ml capacity reaction flask, followed by stirring. A 20 ml portion of THF solution of 4.90 g (20 mmol) of the 4-(2'-p-tolylpropyl)chlorobenzene obtained in the above-mentioned (1) was slowly added dropwise thereto under a reflux condition, followed by stirring under a reflux condition for 6 hours (synthesis of a Grignard compound).

Next, the above-mentioned solution was cooled to 5° C. or less, and 16 ml THF solution of 2.01 g (10 mmol) of the (R)-proline-N-ethyl carbamate methyl ester obtained in Synthesis Example 1 was added dropwise thereto at 10° C. or less and allowed to undergo the reaction. Thereafter, this was heated under reflux for 3 hours and then cooled, and the reaction solution was put into 25 ml of saturated ammonium chloride aqueous solution, mixed with 50 ml of chloroform for extraction, followed by stirring for 1 hour. This was transferred into a separating funnel, and the organic layer was separated and washed twice with saturated brine. After drying the organic layer with anhydrous sodium sulfate, the solvent was evaporated to obtain a concentrate containing the specified substance. By recrystallizing it from a hexane/ethyl acetate mixed solvent, 2.90 g of (5R)-[3,3,0]-1-aza-2-oxo-3-oxa-4,4-bis-(4'-(2''-p-tolylpropyl)phenyl)-bicyclooctane was obtained.

A 29 ml portion of methanol, 29 ml of THF and 1.45 g of 10% Pd—C were added to the thus obtained (5R)-[3,3,0]-1-aza-2-oxo-3-oxa-4,4-bis-(4'-(2''-p-tolylpropyl)phenyl)-bicyclooctane, followed by stirring to carry out hydrogen replacement. After carrying out 15 hours of the reaction at 50° C., Pd—C was removed by filtration and the filtrate was concentrated and purified by a silica gel column chromatography to obtain 1.86 g of colorless crystals of the specified substance with a yield of 24.7%.

$^1$H-NMR (CDCl$_3$): δ=1.30 to 2.00, m, 4H δ=1.60, s, 12H δ=2.30, s, 6H δ=2.70 to 3.00, m, 2H δ=3.75 to 3.90, m, 2H δ=7.00 to 7.30, m, 16H

Synthesis Example 9

Synthesis of (S)-2-(bis-(4'-trifluoromethylphenyl)methyl)pyrrolidine (Synthesis of the Optically Active Cyclic Nitrogen-Containing Compound of Example 60)

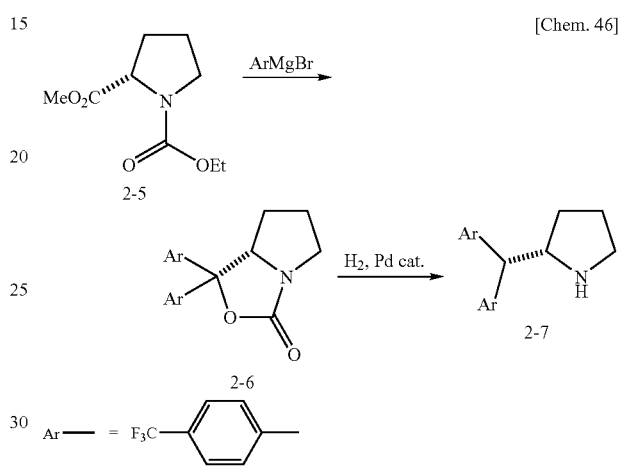

[Chem. 46]

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 2.55 g (105 mmol) of magnesium and 50 ml of anhydrous THF were put into a nitrogen-replaced 300 ml capacity reaction flask, followed by stirring. A 30 ml portion of THF solution of 22.5 g (100 mmol) of 4-trifluoromethylphenylbromobenzene was added dropwise thereto at room temperature, followed by stirring at room temperature for 1 hour (synthesis of a Grignard compound).

Next, the above-mentioned solution was cooled to 5° C. or less, and 10.05 g (50 mmol) of the (S)-proline-N-ethyl carbamate methyl ester obtained in Synthesis Example 2 was added dropwise thereto at 10° C. or less and allowed to undergo the reaction. Thereafter, this was heated under reflux for 3 hours and then cooled, and the reaction solution was put into 100 ml of saturated ammonium chloride aqueous solution, mixed with 100 ml of toluene for extraction, followed by stirring for 1 hour. This was transferred into a separating funnel, and the organic layer was separated and washed twice with saturated brine. After drying the organic layer with anhydrous sodium sulfate, the solvent was evaporated to obtain 12.87 g of (5S)-[3,3,0]-1-aza-2-oxo-3-oxa-4,4-bis-(4'-trifluoromethylphenyl)-bicyclooctane.

A 130 ml portion of methanol and 514 mg of 10% Pd—C were added to the thus obtained (5S)-[3,3,0]-1-aza-2-oxo-3-oxa-4,4-bis-(4'-trifluoromethylphenyl)-bicyclooctane, followed by stirring to carry out hydrogen replacement. After carrying out 4 days of the reaction as such at room temperature, Pd—C was removed by filtration and the filtrate was concentrated and purified by a silica gel column chromatography to obtain 6.74 g of the pale yellow oily specified substance with a yield of 36.11%.

¹H-NMR (CD₃OD): δ=1.25 to 1.50, m, 1H δ=1.70 to 1.95, m, 3H δ=2.80 to 2.90, m, 1H δ=2.90 to 3.05, m, 1H δ=3.90 to 4.05, m, 1H δ=7.45 to 7.65, m, 8H

Synthesis Example 10

Synthesis of (S)-2-(bis-(p-biphenyl)methyl)pyrrolidine (Synthesis of the Optically Active Cyclic Nitrogen-Containing Compound of Example 61)

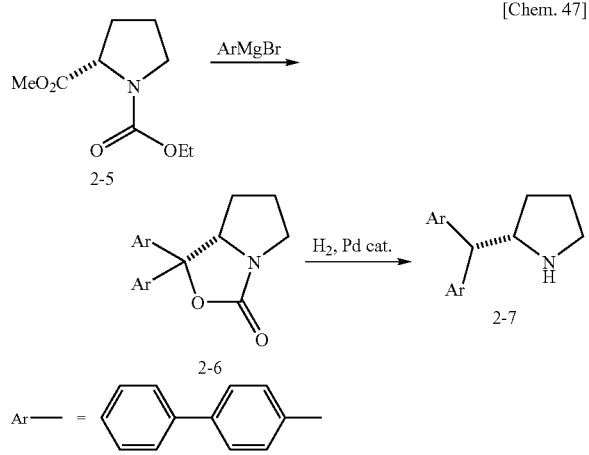

[Chem. 47]

This was synthesized in accordance with the synthesis method of (S)-2-(diphenylmethyl)pyrrolidine described in Tetrahedron: Asymmetry, Vol. 8, No. 1, 149-153.

Under a stream of nitrogen, 2.13 g (87.5 mmol) of magnesium and 10 ml of anhydrous THF were put into a nitrogen-replaced 300 ml capacity reaction flask, followed by stirring. A 54 ml portion of THF solution of 19.1 g (81.9 mmol) of p-bromobiphenyl was added dropwise thereto at room temperature, followed by stirring at room temperature for 1 hour (synthesis of a Grignard compound).

Next, the above-mentioned solution was cooled to 5° C. or less, and 8.00 g (39.8 mmol) of the (S)-proline-N-ethyl carbamate methyl ester obtained in Synthesis Example 2 was added dropwise thereto at 10° C. or less and allowed to undergo the reaction. Thereafter, this was heated under reflux for 3 hours and then cooled, and the reaction solution was put into 100 ml of saturated ammonium chloride aqueous solution, mixed with 100 ml of toluene for extraction, followed by stirring for 1 hour. This was transferred into a separating funnel, and the organic layer was separated and washed twice with saturated brine. After drying the organic layer with anhydrous sodium sulfate, the solvent was evaporated to obtain 6.71 g of (5S)-[3,3,0]-1-aza-2-oxo-3-oxa-4,4-bis-(p-biphenyl)-bicyclooctane.

A 130 ml portion of methanol and 335 mg of 10% Pd—C were added to the thus obtained (5S)-[3,3,0]-1-aza-2-oxo-3-oxa-4,4-bis-(p-biphenyl)-bicyclooctane and stirred to carry out hydrogen replacement. After carrying out 4 days of the reaction as such at room temperature, Pd—C was removed by filtration and the filtrate was concentrated and purified by a silica gel column chromatography to obtain 1.52 g of colorless crystals of the specified substance with a yield of 25.1%.

¹H-NMR (CDCl₃): δ=1.43 to 1.89, m, 5H δ=2.86 to 3.12, m, 2H δ=3.85 to 3.89, m, 2H δ=7.25 to 7.56, m, 18H

Example 1

1 gram (6.57 mmol) of geranial, 25 mg of 5% by weight Pd—C (2.5% by weight based on geranial), 25 mg (0.11 mmol, 2.5% by weight based on geranial) of (R)-2-(diphenylmethyl)pyrrolidine, 12 mg (0.11 mmol) of trifluoroacetic acid and 2 ml of toluene were put into a 10 ml capacity reaction flask, followed by stirring under an atmosphere of hydrogen (0.1 MPa (atmospheric pressure)). After stirring at room temperature for 21 hours and subsequent removal of the catalyst by filtration, the resulting filtrate was analyzed by a gas chromatography to find that conversion ratio of geranial into citronellal was 91%, the thus obtained citronellal was d-form and its optical purity was 67.65% e.e.

Examples 2 to 12

Reactions were carried out in the same manner as in Example 1, except that the optically active cyclic nitrogen-containing compound and acid were changed. In this connection, 25 mg of each optically active cyclic nitrogen-containing compound and the same mol of each acid based on the optically active cyclic nitrogen-containing compound were used. The results are shown in Table 1 and Table 2.

In the tables, TFA represents trifluoroacetic acid, and TCA represents trichloroacetic acid. The same shall apply hereinafter.

TABLE 1

| Example | Optically active cyclic nitrogen-containing compound | Acid | Conversion ratio (%) | Configuration of citronellal | Optical purity (% e.e.) |
|---|---|---|---|---|---|
| 1 | Ph, Ph — pyrrolidine | TFA | 91.98 | d | 67.65 |
| 2 | Ph, Ph — pyrrolidine | TCA | 58.43 | d | 47.24 |
| 3 | Ph, Ph — pyrrolidine | TFA | 60.30 | l | 60.03 |

TABLE 1-continued

| Example | Optically active cyclic nitrogen-containing compound | Acid | Conversion ratio (%) | Configuration of citronellal | Optical purity (% e.e.) |
|---|---|---|---|---|---|
| 4 | (3,5-dimethylphenyl)(3,5-dimethylphenyl)methyl-pyrrolidine | TFA | 71.05 | d | 18.08 |
| 5 | 2-(methoxymethyl)pyrrolidine | TFA | 97.45 | l | 14.02 |
| 6 | tBuO₂C-pyrrolidine | HCl | 17.42 | d | 2.77 |

TABLE 2

| Example | Optically active cyclic nitrogen-containing compound | Acid | Conversion ratio (%) | Configuration of citronellal | Optical purity (% e.e.) |
|---|---|---|---|---|---|
| 7 | H₂N-C(O)-pyrrolidine | TFA | 63.99 | l | 11.10 |
| 8 | MeN-imidazolidinone (tBu) | TFA | 61.35 | l | 24.23 |
| 9 | MeN-imidazolidinone (tBu) | TFA | 41.46 | d | 10.54 |
| 10 | MeN-imidazolidinone (dimethyl, Bn) | HCl | 17.64 | l | 5.89 |
| 11 | MeN-imidazolidinone (tBu, Bn) | TFA | 53.01 | d | 2.78 |

TABLE 2-continued

| Example | Optically active cyclic nitrogen-containing compound | Acid | Conversion ratio (%) | Configuration of citronellal | Optical purity (% e.e.) |
|---|---|---|---|---|---|
| 12 | (2-(5-methylfuran-2-yl)-3-methyl-5-benzyl-imidazolidin-4-one) | TFA | 88.29 | d | 25.95 |

Examples 13 to 25

Reactions were carried out in the same manner as in Example 1, except that neral was used as the reaction substrate and the optically active cyclic nitrogen-containing compound and acid were changed. In this connection, 25 mg of each optically active cyclic nitrogen-containing compound and the same mol of each acid based on the optically active cyclic nitrogen-containing compound were used. The results are shown in Table 3 and Table 4.

TABLE 3

| Example | Optically active cyclic nitrogen-containing compound | Acid | Conversion ratio (%) | Configuration of citronellal | Optical purity (% e.e.) |
|---|---|---|---|---|---|
| 13 | (2-(diphenylmethyl)pyrrolidine) | TFA | 95.41 | d | 61.10 |
| 14 | (2-(diphenylmethyl)pyrrolidine, opposite config) | TFA | 89.71 | l | 56.22 |
| 15 | (2-(bis(3,5-dimethylphenyl)methyl)pyrrolidine) | TFA | 85.06 | d | 5.90 |
| 16 | (2-(bis(3,5-dimethylphenyl)(methoxy)methyl)pyrrolidine) | HCl | 39.34 | l | 4.99 |
| 17 | (2-(methoxymethyl)pyrrolidine) | TFA | 99.83 | l | 12.27 |
| 18 | (2-(diphenyl(trimethylsilyloxy)methyl)pyrrolidine) | TFA | 100 | l | 6.41 |

TABLE 3-continued

| Example | Optically active cyclic nitrogen-containing compound | Acid | Conversion ratio (%) | Configuration of citronellal | Optical purity (% e.e.) |
|---|---|---|---|---|---|
| 19 | H₂N-C(=O)-[pyrrolidine] | TFA | 51.30 | l | 11.10 |

TABLE 4

| Example | Optically active cyclic nitrogen-containing compound | Acid | Conversion ratio (%) | Configuration of citronellal | Optical purity (% e.e.) |
|---|---|---|---|---|---|
| 20 | tBuO₂C-[pyrrolidine] | HCl | 33.56 | d | 3.34 |
| 21 | MeO₂C-[pyrrolidine] | HCl | 60.87 | d | 3.91 |
| 22 | MeN-[imidazolidinone with tBu and CH₂Ph] | TFA | 68.57 | l | 0.15 |
| 23 | MeN-[imidazolidinone with tBu] | TFA | 99.53 | l | 28.20 |
| 24 | MeN-[imidazolidinone with tBu] | TFA | 53.76 | d | 9.21 |
| 25 | MeN-[imidazolidinone with methylfuryl and CH₂Ph] | TFA | 68.01 | d | 25.42 |

Comparative Example 1

The reaction was carried out in the same manner as in Example 1, except that neral was used as the reaction substrate, the optically active cyclic nitrogen-containing compound was changed and the acid was not added. The results are shown in Table 5.

TABLE 5

| Comparative Example | Optically cyclic nitrogen-containing compound | Acid | Conversion ratio (%) | Configuration of citronellal | Optical purity (% e.e.) |
|---|---|---|---|---|---|
| 1 | Ph-CH(Ph)-pyrrolidine | None | 100 | d | 5.64 |

Examples 26 to 29

Reactions were carried out in the same manner as in Example 1, except that citral was used as the reaction substrate and the optically active cyclic nitrogen-containing compound and acid were changed. In this connection, 25 mg of each optically active cyclic nitrogen-containing compound and the same mol of each acid based on the optically active cyclic nitrogen-containing compound were used. The results are shown in Table 6.

TABLE 6

| Example | Optically active cyclic nitrogen-containing compound | Acid | Conversion ratio (%) | Configuration of citronellal | Optical purity (% e.e.) |
|---|---|---|---|---|---|
| 26 | Ph-CH(Ph)-pyrrolidine | TFA | 80.41 | d | 58.46 |
| 27 | Ph-CH(Ph)-pyrrolidine (stereoisomer) | TFA | 89.21 | l | 69.20 |
| 28 | MeN-imidazolidinone (t-Bu) | TFA | 44.67 | l | 13.08 |
| 29 | MeN-imidazolidinone (t-Bu, other stereoisomer) | TFA | 66.93 | d | 12.87 |

Example 30

1 gram (6.57 mmol) of geranial, 12.5 mg of 5% by weight Pd-silica (1.25% by weight based on geranial), 25 mg (0.11 mmol, 2.5% by weight based on geranial) of (R)-2-(diphenylmethyl)pyrrolidine, 12 mg (0.11 mmol) of trifluoroacetic acid and 2 ml of toluene were put into a 10 ml capacity reaction flask, followed by stirring under an atmosphere of hydrogen (0.1 MPa (atmospheric pressure)). After stirring at room temperature for 21 hours and subsequent removal of the catalyst by filtration, the resulting filtrate was analyzed by a gas chromatography to find that conversion ratio of geranial into citronellal was 42.28%, the thus obtained citronellal was d-form and its optical purity was 70.79% e.e.

Examples 31 to 41

Reactions were carried out in the same manner as in Example 30, except that the metal powder or metal-supported substance was changed. The results are shown in Table 7.

TABLE 7

| Example | Metal powder or metal-supported substance | Conversion ratio (%) | Configuration of citronellal | Optical purity (% e.e.) |
|---|---|---|---|---|
| 30 | 5% by weight Pd-silica | 42.28 | d | 70.79 |
| 31 | 5% by weight Pd-silica-alumina | 81.06 | d | 71.63 |
| 32 | Pd-black | 97.23 | d | 65.12 |
| 33 | 5% by weight Pd-alumina | 69.69 | d | 37.01 |
| 34 | 5% by weight Pd-zirconia | 100 | d | 40.51 |
| 35 | 5% by weight Pd-zeolite | 72.03 | d | 73.13 |
| 36 | 5% by weight Pd-barium sulfate | 82.20 | d | 73.95 |
| 37 | 5% by weight Rh-carbon | 39.04 | d | 55.69 |
| 38 | 5% by weight Rh-alumina | 82.12 | d | 47.67 |
| 39 | 5% by weight Ru-carbon | 11.00 | d | 42.01 |
| 40 | 5% by weight Pt-carbon | 21.88 | d | 4.13 |
| 41 | 5% by weight Pt-alumina | 42.44 | d | 0.47 |

Examples 42 to 44

Reactions were carried out in the same manner as in Example 30, except that citral was used as the substrate and the metal-supported substance was changed. The results are shown in Table 8.

TABLE 8

| Example | Metal-supported substance | Conversion ratio (%) | Configuration of citronellal | Optical purity (% e.e.) |
|---|---|---|---|---|
| 42 | 5% by weight Pd-silica-alumina | 44.04 | d | 75.08 |
| 43 | 5% by weight Pd-zeolite | 74.51 | d | 71.31 |
| 44 | 5% by weight Pd-barium sulfate | 60.21 | d | 72.76 |

Examples 45 to 47

Reactions were carried out in the same manner as in Example 30, except that neral was used as the substrate and the metal-supported substance was changed. The results are shown in Table 9.

TABLE 9

| Example | Metal-supported substance | Conversion ratio (%) | Configuration of citronellal | Optical purity (% e.e.) |
|---|---|---|---|---|
| 45 | 5% by weight Pd-silica-alumina | 73.29 | d | 68.17 |
| 46 | 5% by weight Pd-zeolite | 70.24 | d | 70.02 |
| 47 | 5% by weight Pd-barium sulfate | 63.59 | d | 74.46 |

Example 48

2 grams (13.14 mmol) of citral, 25 mg of 5% by weight Pd-barium sulfate (1.25% by weight based on citral), 80 mg (0.23 mmol, 4.0% by weight based on citral) of (R)-2-(bis-(4'-t-butylphenyl)methyl)pyrrolidine, 26.1 mg (0.23 mmol) of trifluoroacetic acid and 4 ml of 10% by weight aqueous t-BuOH were put into a 10 ml capacity reaction flask, followed by stirring under an atmosphere of hydrogen (0.1 MPa (atmospheric pressure)). After stirring at 40° C. for 21 hours and subsequent removal of the catalyst by filtration, the resulting filtrate was analyzed by a gas chromatography to find that conversion ratio from citral into citronellal was 51%, the thus obtained citronellal was d-form and its optical purity was 84.91% e.e.

Examples 49 to 64

Reactions were carried out in the same manner as in Example 48, except that the reaction was carried out at 25° C. in Example 49, at 50° C. in Example 50, at 60° C. in Example 51 and at 25° C. in toluene in Examples 61 and 62, and the optically active cyclic nitrogen-containing compound and acid were changed as other conditions. In this connection, 80 mg of each optically active cyclic nitrogen-containing compound and the same mol of each acid based on the optically active cyclic nitrogen-containing compound were used. The results are shown in Tables 10 to 12.

TABLE 10

| Example | Optically active cyclic nitrogen-containing compound | Acid | Conversion ratio (%) | Configuration of citronellal | Optical purity (% e.e.) |
|---------|------------------------------------------------------|------|----------------------|------------------------------|-------------------------|
| 48 | 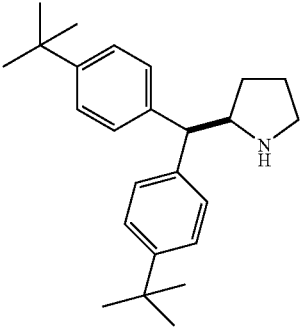 | TFA | 51.36 | d | 84.91 |
| 49 | 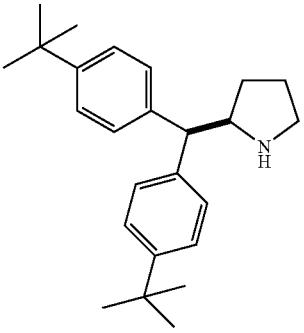 | TFA | 25.90 | d | 73.04 |
| 50 | 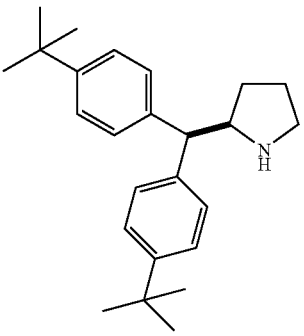 | TFA | 98.66 | d | 80.37 |

TABLE 10-continued

| Example | Optically active cyclic nitrogen-containing compound | Acid | Conversion ratio (%) | Configuration of citronellal | Optical purity (% e.e.) |
|---|---|---|---|---|---|
| 51 | | TFA | 99.71 | d | 83.82 |
| 52 | | L-Mandelic acid | 100 | d | 69.31 |
| 53 | | D-Mandelic acid | 100 | d | 71.45 |

TABLE 11

| Example | Optically active cyclic nitrogen-containing compound | Acid | Conversion ratio (%) | Configuration of citronellal | Optical purity (% e.e.) |
|---|---|---|---|---|---|
| 54 | | TFA | 39.85 | l | 83.67 |
| 55 | | TFA | 35.90 | l | 83.65 |
| 56 | | TFA | 91.77 | d | 83.18 |
| 57 | | TFA | 66.72 | l | 76.91 |

TABLE 11-continued

| Example | Optically active cyclic nitrogen-containing compound | Acid | Conversion ratio (%) | Configuration of citronellal | Optical purity (% e.e.) |
|---|---|---|---|---|---|
| 58 | [structure: bis(4-(1-adamantyl)phenyl)methyl pyrrolidine] | TFA | 11.44 | d | 73.43 |

TABLE 12

| Example | Optically active cyclic nitrogen-containing compound | Acid | Conversion ratio (%) | Configuration of citronellal | Optical purity (% e.e.) |
|---|---|---|---|---|---|
| 59 | [structure: bis(4-(2-(p-tolyl)propan-2-yl)phenyl)methyl pyrrolidine] | TFA | 22.41 | d | 82.81 |
| 60 | [structure: bis(4-(trifluoromethyl)phenyl)methyl pyrrolidine] | TFA | 71.49 | l | 76.16 |

TABLE 12-continued

| Example | Optically active cyclic nitrogen-containing compound | Acid | Conversion ratio (%) | Configuration of citronellal | Optical purity (% e.e.) |
|---|---|---|---|---|---|
| 61 | (structure: bis-biphenylmethyl pyrrolidine) | TFA | 28.24 | l | 68.75 |
| 62 | (structure: triphenylmethyl pyrrolidine, Ph₃C-pyrrolidine) | TFA | 49.61 | d | 51.86 |
| 63 | (structure: 3-benzyl-3,4-dihydroquinoxalin-2(1H)-one) | TFA | 32.43 | l | 7.97 |
| 64 | (structure: 3-isopropyl-3,4-dihydroquinoxalin-2(1H)-one) | TFA | 91.36 | d | 7.09 |

Example 65

1 gram (6.84 mmol) of β-methylcinnamaldehyde, 50 mg of 5% by weight Pd—C (5% by weight based on β-methylcinnamaldehyde), 25 mg (0.11 mmol, 2.5% by weight based on β-methylcinnamaldehyde) of (R)-2-(diphenylmethyl)pyrrolidine, 12 mg (0.11 mmol) of trifluoroacetic acid and 2 ml of toluene were put into a 10 ml capacity reaction flask, followed by stirring under an atmosphere of hydrogen (0.1 MPa (atmospheric pressure)). After stirring at room temperature for 21 hours and subsequent removal of the catalyst by filtration, the resulting filtrate was analyzed by a gas chromatography to find that the conversion ratio was 89% and optical purity of the thus obtained (S)-3-phenylbutylaldehyde was 34.88% e.e.

Example 66

The reaction was carried out in the same manner as in Example 65, except that (R)-2-(tert-butyl)-3-methyl-4-imidazolidinone was used as the optically active cyclic nitrogen-containing compound. The conversion ratio was 82% and optical purity of the thus obtained (S)-3-phenylbutylaldehyde was 26.81% e.e.

Example 67

Synthesis of l-menthol

A 500.0 g (3.28 mol) portion of citral, 6.25 g of 5% by weight Pd-silica-alumina (1.25% by weight based on citral), 12.5 g (52.7 mmol, 2.5% by weight based on citral) of (R)-2-(diphenylmethyl)pyrrolidine, 6 g (52.7 mmol) of trifluoroacetic acid and 1 liter of toluene were put into a 3 liter capacity reaction flask, followed by stirring under an atmosphere of hydrogen (0.1 MPa (atmospheric pressure)). After stirring at room temperature for 21 hours and subsequent removal of the catalyst by filtration, the resulting filtrate was analyzed by a gas chromatography to find that conversion ratio from citral into citronellal was 80.4% and its optical purity 70.66% e.e. The thus obtained crude d-citronellal was distilled to obtain 320 g (2.07 mol, yield 63.1%) of d-citronellal having a purity of 98%.

A 15.26 g (20 mmol) portion of the tris(2,6-diphenylphenoxy)aluminum catalyst described in JP-A-2002-212121 and 300 ml of toluene were added to 308.5 g (2.0 mol) of the d-citronellal, followed by stirring at 5° C. for 5 hours, and the reaction solution was distilled to obtain 283.8 g (1.84 mol, yield 92%) of l-isopulegol (99.5% n-form, 70.85% e.e.)

By adding 0.45 g of Raney nickel to 283.8 g of the thus obtained l-isopulegol, 10 hours of hydrogenation was carried out at 70° C. under a hydrogen pressure of 2.5 MPa. By carrying out filtration and distillation of the reaction solution, 273.5 g (1.75 mol, 71.24% e.e.) of 1-menthol was obtained.

While the invention has been described in detail and with reference to specific embodiments thereof, it will be apparent to one skilled in the art that various changes and modifications can be made therein without departing from the spirit and scope of the invention.

The catalyst for asymmetric hydrogenation to be used in the invention, which is prepared by simply mixing a metal powder or metal-supported substance, an optically active cyclic nitrogen-containing compound and an acid, can produce an optically active α,β-carbonyl compound by conveniently carrying out asymmetric hydrogenation of its substrate, an α,β-unsaturated carbonyl compound.

That is, optically active citronellal can be obtained by conducting selective asymmetric hydrogenation of α,β-carbon-carbon double bond of citral (a mixture of geranial and neral), geranial or neral. The optically active citronellal is not only useful by itself as a flavor or fragrance but is also an important raw material of optically active citronellol, optically active isopulegol and optically active menthol.

In addition, since the catalyst of the invention is not soluble in the reaction solution, the metal or metal-supported substance and optically active cyclic nitrogen-containing compound can be easily recovered and recycled, which is industrially advantageous.

What is claimed is:

1. A catalyst for asymmetric hydrogenation of an α, β-unsaturated carbonyl compound, which comprises:
   a powder of at least one metal selected from metals belonging to Group 8 to Group 10 of the Periodic Table, or a metal-supported substance in which at least one metal selected from metals belonging to Group 8 to Group 10 of the Periodic Table is supported on a support;
   an optically active cyclic nitrogen-containing compound; and
   an acid,
   wherein the optically active cyclic nitrogen-containing compound is a compound represented by the following general formula (1):

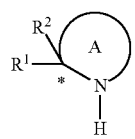

(1)

wherein ring A is a three- to seven-membered ring which may have a substituent, comprises at least one kind of atom selected from the group consisting of a carbon atom, a nitrogen atom, a sulfur atom, an oxygen atom and a phosphorous atom, and may be a fused ring structure; $R^1$ and $R^2$ each independently represent an hydrogen atom, an alkyl group which may have a substituent, a cycloalkyl group which may have a substituent, an alkenyl group which may have a substituent, an aryl group which may have a substituent, an aralkyl group which may have a substituent, an alkoxy group which may have a substituent, a carboxyl group which may have a substituent, alkoxycarbonyl group which may have a substituent, an amide group which may have a substituent, a siloxy group which may have a substituent, an aromatic heterocyclic ring which may have a substituent or an aliphatic heterocyclic ring which may have a substituent, wherein $R^1$ and $R^2$ do not represent a same substituent, and either $R^1$ or $R^2$ may be bonded to the ring A to further form a ring; and * represents an asymmetric carbon atom, and
the optically active cyclic nitrogen-containing compound does not include amino acids.

2. The catalyst for asymmetric hydrogenation according to claim 1, wherein the metal is selected from the group consisting of nickel, ruthenium, rhodium, iridium, palladium and platinum.

3. A method for manufacturing an optically active carbonyl compound represented by the following general formula (3):

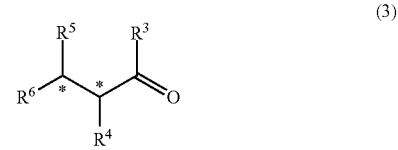

(3)

wherein $R^3$, $R^4$, $R^5$ and $R^6$ are the same as defined in the following formula (2), and two * mean that at least one * represents an asymmetric carbon atom,
wherein the method comprises conducting asymmetric hydrogenation of an α, β-unsaturated carbonyl compound represented by the following general formula (2) by using the catalyst for asymmetric hydrogenation according to claim 1 or 2:

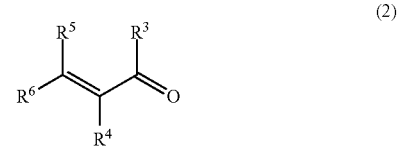

(2)

wherein $R^3$, $R^4$, $R^5$ and $R^6$ each independently represent an hydrogen atom, an alkyl group which may have a substituent, a cycloalkyl group which may have a substituent, an alkenyl group which may have a substituent, an aryl group which may have a substituent, or an aralkyl group which may have a substituent, and a ring may be formed by $R^3$ and $R^4$, $R^3$ and $R^5$, $R^3$ and $R^6$, $R^4$ and $R^6$, or $R^5$ and $R^6$; and when a ring is not formed by $R^3$ and $R^4$, or $R^3$ and $R^5$, and $R^4$ does not represent a hydrogen atom, $R^5$ and $R^6$ may be the same or different from each other; and when a ring is not formed by $R^3$ and $R^4$, or $R^3$ and $R^5$, and $R^4$ represents a hydrogen atom, $R^5$ and $R^6$ do not represent a hydrogen atom and are different from each other.

4. The method according to claim 3, wherein the α, β-unsaturated carbonyl compound is geranial, neral or citral.

5. The method according to claim 3, wherein the α, β-unsaturated carbonyl compound is ketones having a five- to sixteen-membered ring.

6. The catalyst for asymmetric hydrogenation according to claim 1, wherein the carboxyl group in $R^1$ and $R^2$ is selected from the group consisting of an acetoxy group, a n-propanoyloxy group, an isopropanoyloxy group, a n-butanoyloxy group, a 2-butanoyloxy group, an isobutanoyloxy group, a tert-butanoyloxy group, a n-pentanoyloxy group, a 2-methylbutanoyloxy group, a 3-methylbutanoyloxy group, a 2,2-dimethylpropanoyloxy group, a n-hexanoyloxy group, a 2-methylpentanoyloxy group, a 3-methylpentanoyloxy group, a 4-methylpentanoyloxy group, a 5-methylpentanoyloxy group, a cyclopentanoyloxy group, a cyclohexanoyloxy group, a dicyclopentylacetoxy group, a dicyclohexylacetoxy group, a tricyclopentylacetoxy group, a tricyclohexylacetoxy group, a phenylacetoxy group, a diphenylacetoxy group, a triphenylacetoxy group, a benzoyloxy group, and a naphthoyloxy group.

* * * * *